(12) United States Patent
Ott

(10) Patent No.: US 12,378,510 B2
(45) Date of Patent: Aug. 5, 2025

(54) LUNG BIOREACTOR

(71) Applicant: The General Hospital Corporation, Boston, MA (US)

(72) Inventor: Harald C. Ott, Wenham, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 18/391,115

(22) Filed: Dec. 20, 2023

(65) Prior Publication Data

US 2024/0124813 A1 Apr. 18, 2024

Related U.S. Application Data

(62) Division of application No. 17/897,560, filed on Aug. 29, 2022, now Pat. No. 11,891,593, which is a
(Continued)

(51) Int. Cl.
*C12M 3/00* (2006.01)
*A01N 1/00* (2006.01)
(Continued)

(52) U.S. Cl.
CPC ............. *C12M 21/08* (2013.01); *A01N 1/143* (2025.01); *A61K 35/28* (2013.01); *A61K 35/36* (2013.01); *A61K 35/42* (2013.01); *A61K 35/44* (2013.01); *C12M 25/14* (2013.01); *C12M 29/10* (2013.01); *C12M 41/40* (2013.01); *C12M 41/44* (2013.01); *C12M 41/48* (2013.01)

(58) Field of Classification Search
CPC ............................. C12M 21/08; A01N 1/0247
See application file for complete search history.

(56) References Cited

U.S. PATENT DOCUMENTS

| 6,087,552 A | 7/2000 | Gregory |
| 6,953,655 B1 | 10/2005 | Hassanein et al. |

(Continued)

FOREIGN PATENT DOCUMENTS

| CN | 1320014 A | 10/2001 |
| CN | 2689225 | 3/2005 |

(Continued)

OTHER PUBLICATIONS

Aigner et al., "Clinical Ex Vivo Lung Perfusion—Pushing the Limits," American Journal of Transplantation, 2012, 12:1839-1847.
(Continued)

*Primary Examiner* — Nathan A Bowers
(74) *Attorney, Agent, or Firm* — Fish & Richardson P.C.

(57) ABSTRACT

Presented is an airway organ bioreactor apparatus, and methods of use thereof, as well as bioartificial airway organs produced using the methods, and methods of treating subjects using the bioartificial airway organs. The bioreactor comprises: an organ chamber: an ingres line connecting the organ chamber and a reservoir system and comprising an arterial line, a venous line and a tracheal line; an egress line connecting the chamber and the reservoir system, pumps in ingress and egress lines; a controller to control fluid exchange; a chamber pressure sensor connected to the organ chamber.

20 Claims, 22 Drawing Sheets

Related U.S. Application Data division of application No. 15/125,891, filed as application No. PCT/US2015/020605 on Mar. 13, 2015, now Pat. No. 11,427,797.

(60) Provisional application No. 61/953,191, filed on Mar. 14, 2014.

(51) Int. Cl.

| | |
|---|---|
| *A01N 1/143* | (2025.01) |
| *A61K 35/28* | (2015.01) |
| *A61K 35/36* | (2015.01) |
| *A61K 35/42* | (2015.01) |
| *A61K 35/44* | (2015.01) |
| *C12M 1/00* | (2006.01) |
| *C12M 1/12* | (2006.01) |
| *C12M 1/34* | (2006.01) |
| *C12M 1/36* | (2006.01) |

(56) References Cited

U.S. PATENT DOCUMENTS

| | | |
|---|---|---|
| 7,662,409 B2 | 2/2010 | Masters |
| 2002/0172705 A1 | 11/2002 | Murphy et al. |
| 2002/0182241 A1 | 12/2002 | Borenstein et al. |
| 2002/0182261 A1 | 12/2002 | Dai et al. |
| 2003/0073227 A1 | 4/2003 | Hull et al. |
| 2003/0087428 A1 | 5/2003 | Wolfinbarger et al. |
| 2003/0129751 A1 | 7/2003 | Grikscheit et al. |
| 2003/0166274 A1 | 9/2003 | Hewitt et al. |
| 2005/0147958 A1 | 7/2005 | Hassanein et al. |
| 2005/0196423 A1 | 9/2005 | Batich et al. |
| 2005/0256588 A1 | 11/2005 | Sawa et al. |
| 2006/0148062 A1* | 7/2006 | Hassanein .............. A01N 1/126 435/284.1 |
| 2007/0059293 A1 | 3/2007 | Atala |
| 2007/0244568 A1 | 10/2007 | Matsuda et al. |
| 2008/0017194 A1 | 1/2008 | Hassanein et al. |
| 2008/0131473 A1 | 6/2008 | Brown et al. |
| 2008/0292677 A1 | 11/2008 | Cortiella et al. |
| 2009/0035855 A1 | 2/2009 | Ying et al. |
| 2009/0075282 A1 | 3/2009 | Mahmood et al. |
| 2009/0142836 A1 | 6/2009 | Wang et al. |
| 2009/0197325 A1* | 8/2009 | Fishman .............. A01N 1/0247 435/284.1 |
| 2009/0292677 A1 | 8/2009 | Ott et al. |
| 2010/0034791 A1 | 2/2010 | Lelkes et al. |
| 2012/0141439 A1 | 6/2012 | Ott |
| 2012/0183944 A1 | 7/2012 | Taylor et al. |
| 2014/0017770 A1 | 1/2014 | Steinman et al. |
| 2014/0315175 A1* | 10/2014 | Nguyen ................. G09B 23/30 434/272 |
| 2015/0017710 A1 | 1/2015 | Freed et al. |

FOREIGN PATENT DOCUMENTS

| | | |
|---|---|---|
| JP | 2001-516768 | 10/2001 |
| JP | 2004-350557 | 12/2004 |
| JP | 2006-000105 | 1/2006 |
| JP | 2012-516699 | 7/2012 |
| WO | WO 1999/015011 | 4/1999 |
| WO | WO 2000/018226 | 4/2000 |
| WO | WO 2010/091188 | 8/2010 |
| WO | WO 2013/071096 | 5/2013 |
| WO | WO 2014/110135 | 7/2014 |

OTHER PUBLICATIONS

Albelda et al., "Effects of increased ventilation on lung lymph flow in unanesthetized sheep," J Appl Physiol, Jun. 1986, 60(6):2063-70.
Andrade et al., "Cell-based tissue engineering for lung regeneration," Am J Physiol Lung Cell Mol Physiol, Feb. 2007, 292(2):L510-8.
Bhattacharya et al., "Lung expansion and the perialveolar interstitial pressure gradient," J Appl Physiol, Jun. 1989, 66: 2600-5.
Boasquevisque et al., "Surgical Techniques: Lung Transplant and Lung Volume Reduction," Proceedings of the American Thoracic Society, Jan. 2009, 6:66-78.
Bribriesco et al., "Experimental models of lung Transplantation," Front Biosci (Elite Ed), Jan. 2013, 5:266-72.
Brudno et al. "Enhancing microvascular formation and vessel maturation through temporal control over multiple pro-angiogenic and pro-maturation factors," Biomaterials, Dec. 2013, 34: 9201-9209.
Camargo et al., "Surgical maneuvers for the management of bronchial complications in lung transplantation," Eur J Cardiothorac Surg, Dec. 2008, 34:1206-1209.
Chen et al., "Formation of lung alveolar-like structures in collagen-glycosaminoglycan scaffolds in vitro," Tissue Eng., Sep.-Oct. 2005, 11(9-10):1436-48.
Desai and Cardoso, "Growth factors in lung development and disease: friends or foe?," Respire. Res., 2002, 3:2, 4 pages.
Erasmus et al., "Normothermic ex vivo lung perfusion of non-heart-beating donor lungs in pigs: from pretransplant function analysis towards a 6-h machine preservation," Transpl Int, Jul. 2006, 19:589-593.
Gaissert and Patterson, "Surgical Techniques of Single and Bilateral Lung Transplantation in the Transplantation and Replacement of Thoracic Organs," 2nd ed., 1996, 7 pages.
Gilbert et al., "Decellularization of tissues and organs," Biomaterials, 2006, 27(9):3675-83.
Gilpin et al., "Perfusion decellularization of human and porcine lungs: Bringing the matrix to clinical scale," Journal of Heart and Lung Transplantation, Mar. 2014, 33:298-308.
Granger et al., "Dynamics and control of transmicrovascular fluid exchange," Edema, 1984, 8:189-228.
Groβ et al., "Improved generation of patient-specific induced pluripotent stem cells using a chemically-defined and matrigel-based approach," Curr Mol Med., Jun. 2013,13:765-76.
Hoganson et al., "Tissue Engineering and Organ Structure: A Vascularized Approach to Liver and Lung," Pediatric Research, May 2008, 63(5):520-526.
Hou et al., "Pluripotent Stem Cells Induced from Mouse Somatic Cells by Small-Molecule Compounds," Science, Jul. 2013, 341:651:654.
Ingenito et al., "Design and testing of biological scaffolds for delivering reparative cells to target sites in the lung," J Tissue Eng Regen Med., 2010, 4: 259-272.
International Preliminary Report on Patentability in International Application No. PCT/US2015/020605, mailed Sep. 14, 2016, 9 pages.
International Search Report and Written Opinion in International Application No. PCT/US2015/020605, mailed May 26, 2015, 13 pages.
Li et al., "Generation of iPSCs from mouse fibroblasts with a single gene, Oct4, and small molecules," Cell Res., Jan. 2011, 21:196-204.
Liao et al., "Effects of Decellularization on the Mechanical and Structural Properties of the Porcine Aortic Valve Leaflet," Biomaterials, Mar. 2008, 29(8): 1065-74.
Lin and Ying, "Mechanism and method for generating tumor-free iPS cells using intronic microRNA miR-302 induction," Methods Mol Biol., 2013, 936:295-312.
Maghsoudlou et al., "Preservation of micro-architecture and angiogenic potential in a pulmonary acellular matrix obtained using intermittent intra-tracheal flow of detergent enzymatic treatment," Biomaterials, Sep. 2013, 34(28):6638-48.
Malik and Rao, "A Review of the Methods for Human iPSC Derivation," Methods Mol Biol., 2013, 997:23-33.
Nichols et al., "Production and assessment of decellularized pig and human lung scaffolds," Tissue Eng Part A, Sep. 2013, 19(17-18):2045-62.
Office Action in Chinese Application No. 201580026004.X, dated Mar. 11, 2019, 18 pages (with English translation).
Office Action in Chinese Appln. No. 201580026004.X, dated May 23, 2023, 8 pages (with English translation).
Office Action in Japanese Application No. 2016-575640, dated Feb. 19, 2019, 22 pages (with English translation).

(56) References Cited

OTHER PUBLICATIONS

Okano et al., "Steps toward safe cell therapy using induced pluripotent stem cells," Circ Res., Feb. 2013, 112(3):523-33.
O'Neill et al., "Decellularization of human and porcine lung tissues for pulmonary tissue engineering," Ann Thorac Surg., Sep. 2013, 96(3): 1046-55.
Ott et al., "Regeneration and orthotopic transplantation of a bioartificial lung," Nat Med., Aug. 2010, 16(8):927-33.
Park et al., "Reprogramming of human somatic cells to pluripotency with defined factors," Nature, Jan. 2008, 451:141-146.
Pasque et al., "Standardizing thoracic organ procurement for transplantation," J Thorac Cardiovasc Surg., Jan. 2010, 139(1):13-7.
Petersen et al., "Bioreactor for the Long-Term Culture of Lung Tissue," Cell Transplantation, 2011, 20:1117-1126.
Reed et al., "Stem cell-derived endothelial cells for cardiovascular disease: a therapeutic perspective," Br J Clin Pharmacol, Apr. 2013, 75(4):897-906.
Song et al., "Bioartificial lung engineering," Am J Transplant., Feb. 2012, 12(2):283-8.
Song et al., "Enhanced in vivo function of bioartificial lungs in rats," Ann Thorac Surg, Sep. 2011, 92(3):998-1005.
Takahashi et al., "Induction of Pluripotent Stem Cells from Adult Human Fibroblasts by Defined Factors," Cell, Nov. 2007, 131:861-72.
Teebken et al., "Tissue Engineering of Vascular Grafts: Human Cell Seeding of Decellularised Porcine Matrix," Eur. J. Vasc. Endovasc. Surg., Apr. 2000, 19:381-86.
Venkateswaran et al., "Measurement of extravascular lung water following human brain death: implications for lung donor assessment and transplantation," Eur J Cardiothorac Surg., Jun. 2013, 43(6):1227-32.
Venkateswaran et al., "The proinflammatory environment in potential heart and lung donors: prevalence and impact of donor management and hormonal therapy," Transplantation, Aug. 2009, 88(4):582-8.
Venuta et al., "Evolving Techniques and Perspectives in Lung Transplantation," Transplantation Proceedings, Jul.-Aug. 2005, 37(6):2682-2683.
Yang and Conte, "Finer techniques in lung transplantation," Transplantation Proceedings, Nov. 2000, 32(7): 1521-1522.
Yoshida et al., "Surgical Technique of Experimental Lung Transplantation in Rabbits," Ann Thorac Cardiovasc Surg., Jan. 2005, 11(1):7-11.
Yu et al., "Induced pluripotent stem cell lines derived from human somatic cells," Science, Nov. 2007, 318: 1917-20.
Zhu et al., "Reprogramming of Human Primary Somatic Cells by OCT4 and Chemical Compounds," Cell Stem Cell., Dec. 2010, 7:651-5.

\* cited by examiner

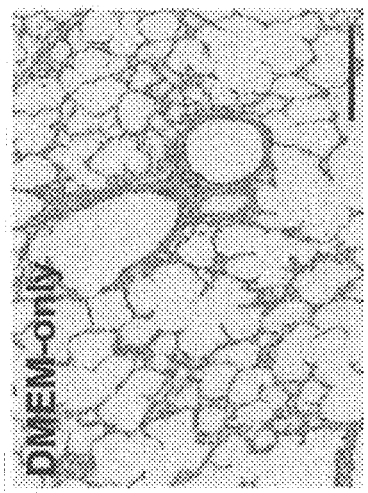
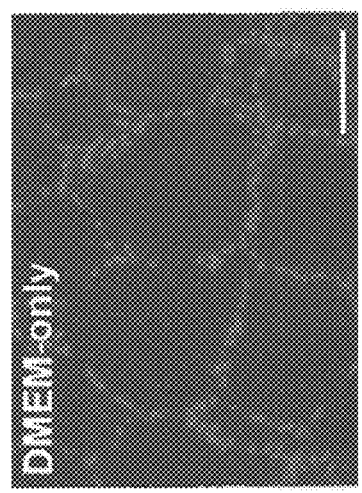
FIG. 11C
FIG. 11D
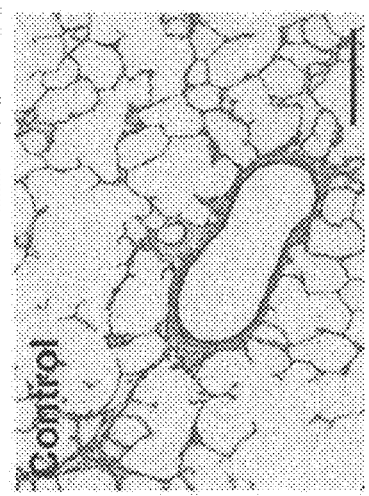
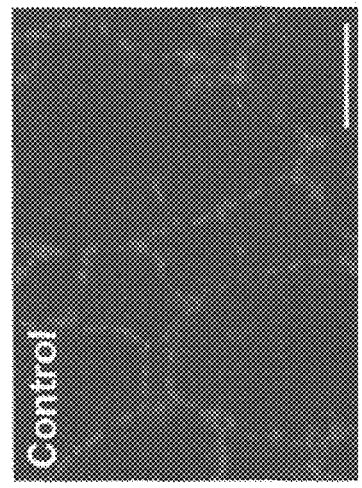

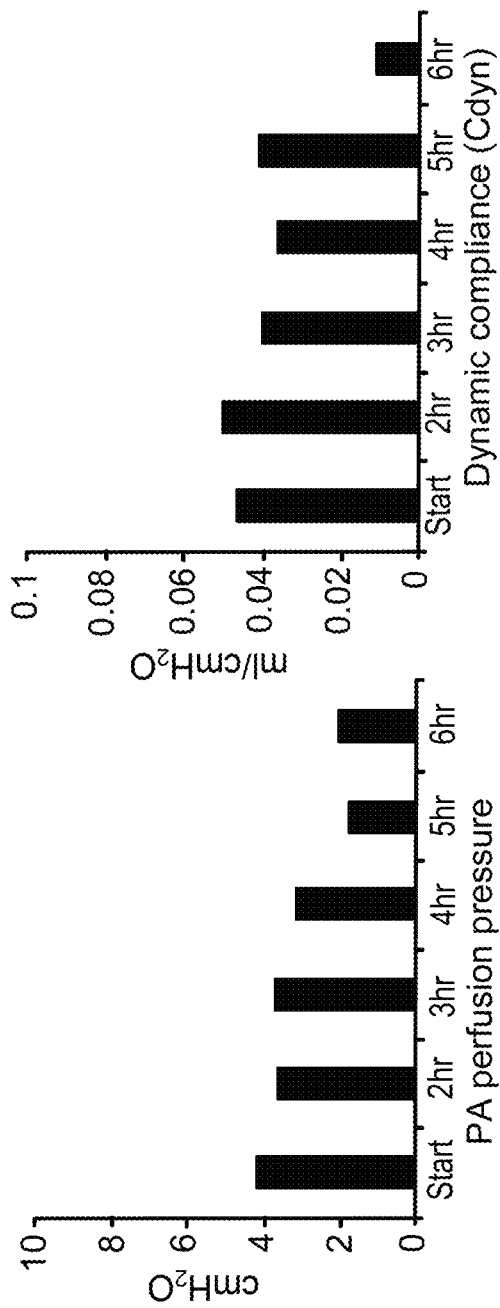
FIG. 15A
FIG. 15B
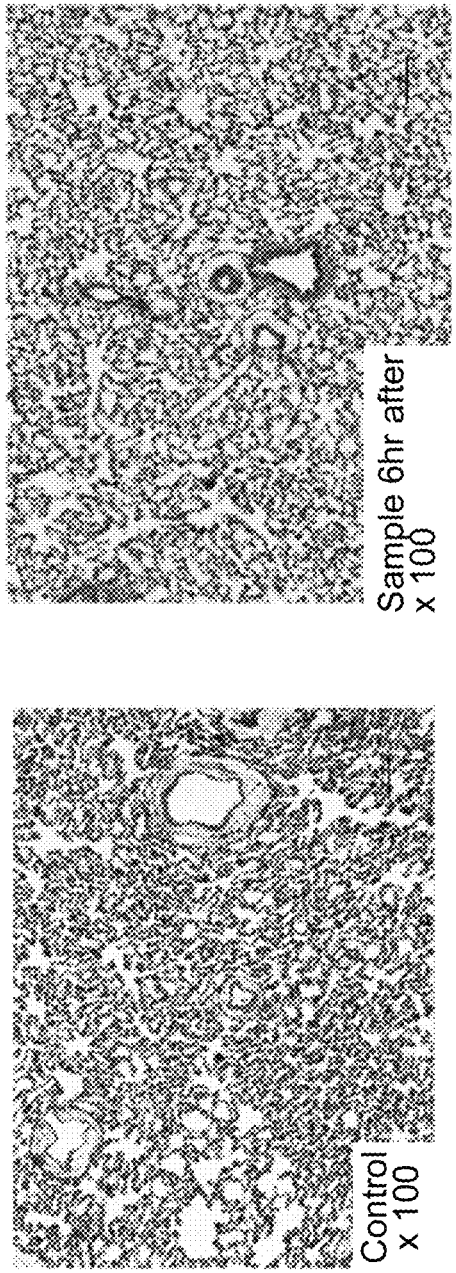
FIG. 15C

LUNG BIOREACTOR

CLAIM OF PRIORITY

The present application is a divisional of U.S. application Ser. No. 17/897,560, filed Aug. 29, 2022, which is a divisional of U.S. application Ser. No. 15/125,891, filed Sep. 13, 2016, now U.S. Pat. No. 11,427,797, which is a § 371 National Stage Application of PCT/US2015/020605, filed Mar. 13, 2015, which claims priority to U.S. provisional application No. 61/953,191 filed Mar. 14, 2014, each of which is incorporated herein by reference in its entirety.

TECHNICAL FIELD

This invention relates to lung bioreactor assemblies and methods.

BACKGROUND

Lung transplants represent a final hope for many patients experiencing conditions typified by lung failure, e.g., chronic obstructive pulmonary disease (COPD), cystic fibrosis, pulmonary hypertension, lung cancers, and congenital lung diseases. Typical wait time for a lung transplant can be two years or more, resulting in a 30% mortality rate for those on the waiting list.

SUMMARY

In one aspect, an airway organ bioreactor apparatus includes an organ chamber configured to hold an organ matrix scaffold or organ into which a fluid is perfused, an ingress line connecting the organ chamber and a reservoir system, in which the ingress line includes any of the following: a fluid line, an arterial line, a venous line, a tracheal line, or an ingress pump, an egress line connecting the organ chamber and the reservoir system, in which the egress line includes an egress pump, a controller configured to control fluid exchange between the organ chamber and the reservoir system through the ingress line and the egress line, and a chamber pressure sensor connected to the organ chamber, wherein the chamber pressure sensor is configured to record and transmit the chamber pressure to the controller.

In another aspect, a method of providing a wet-matured lung organ includes providing an organ chamber configured to connect to an arterial line, to a venous line, and to a tracheal line, providing a lung tissue matrix including an airway and substantial vasculature, connecting the airway to the tracheal line, connecting the lung tissue matrix to the arterial line and to the venous line, seeding the lung tissue matrix with cells over at least one of the following: the arterial line, the venous line, or the tracheal line, providing the lung tissue matrix with wet ventilation for a time sufficient for a first desired degree of organ maturation to occur to produce a wet-matured organ, and optionally maintaining a substantially constant fluid level in the organ chamber during wet ventilation.

In a further aspect, a method of preserving, repairing, and/or modifying a lung organ includes providing an organ chamber configured to connect to an arterial line, to a venous line, and to a tracheal line, providing a wet-matured lung or a harvested lung, including an airway and substantial vasculature, connecting the airway to the tracheal line, connecting the wet-matured lung or the harvested lung to an arterial line and a venous line, perfusing media over the vasculature of the wet-matured lung or the harvested lung through at least the arterial line or the venous line, providing the wet-matured lung or the harvested lung with dry ventilation for a time sufficient to produce or maintain a functional lung organ, and minimizing tracheal pressure fluctuation.

Implementations can include one or more of the following features.

In some implementations, the ingress pump, the egress pump, or both is a bi-directional pump.

In certain implementations, the controller is configured to control fluid exchange between the organ chamber and the reservoir system through the ingress line and the egress line by any of the following: controlling a direction of the bi-directional pump, or controlling the duration of a pump cycle of the bi-directional pump.

In some implementations, the controller is configured to control fluid exchange between the organ chamber and the reservoir system through the ingress line and the egress line in response to data transmitted from the chamber pressure sensor.

In certain implementations, the ingress line comprises the arterial line, the venous line, and the tracheal line.

In some implementations, the tracheal line is connected to the organ chamber and to a positive pressure manifold including: a gas source, a pressure reservoir connected to the gas source, and a pressure release valve connected to the pressure reservoir, in which the positive pressure manifold is controlled by the controller.

In certain implementations, the positive pressure manifold is configured to apply continuous positive pressure along the tracheal line.

In some implementations, one or both of the arterial line and venous line includes a pressure sensor, a fluid pump, or both a pressure sensor and a fluid pump.

In certain implementations, the arterial line includes a first pressure sensor and a first pump, each controlled by the controller, the venous line includes a second pressure sensor controlled by the controller, and the tracheal line includes a third pressure sensor and a third pump, each controlled by the controller.

In some implementations, the third pump is bi-directional.

In certain implementations, the arterial line and the venous line are connected to the reservoir system and the tracheal line is connected to a ventilator.

In some implementations a pneumatic pressure control module is connected to the organ chamber, in which the pneumatic pressure control module includes: a gas inlet line including an inlet pressure valve, an inlet pressure reservoir, and an inlet compressor, and a gas outlet line including an outlet pressure valve, an outlet pressure reservoir, and an outlet compressor, in which the controller controls any of the following: the inlet pressure valve, the inlet compressor, the outlet pressure valve, or the outlet compressor.

In certain implementations, the organ chamber includes a chamber pressure sensor and a bi-directional drainage chamber pump each controlled by a control module that controls the bi-directional drainage pump in response to data transmitted by the chamber pressure sensor.

In some implementations, preventing a transpulmonary pressure gradient is accomplished by equilibrating a pressure level in the venous line with a pressure level in a media reservoir.

In certain implementations, the organ chamber further includes a pneumatic pressure control module connected to the organ chamber, in which the pneumatic pressure control module: generates negative pressure in the organ chamber during an inspiration phase, maintains the organ chamber pressure for a plateau phase, and generates positive pressure in the organ chamber during an expiration phase.

In some implementations, wet ventilation includes: connecting the tracheal line to a media reservoir, in which the tracheal line includes a bi-directional tracheal pump connected to the controller, inflating the lung tissue matrix with media using the bi-directional tracheal pump, and deflating the lung tissue matrix using the bi-directional tracheal pump to withdraw media from the lung tissue matrix. The media is continuously refreshed during wet ventilation.

In certain implementations, the wet ventilation includes: connecting the tracheal line to a media reservoir, in which the tracheal line includes a first pump and a second pump each connected to the controller, inflating the lung tissue matrix with media using the first pump, and deflating the lung tissue matrix using the second pump to withdraw media from the lung tissue matrix. The media is continuously refreshed during wet ventilation.

In some implementations, the controller controls the bi-directional tracheal pump in response to data transmitted by a tracheal pressure sensor connected to the tracheal line.

In certain implementations, minimizing tracheal pressure fluctuation includes: connecting the tracheal line to a media reservoir, in which the tracheal line includes a ventilator and a tracheal pressure sensor each connected to the controller, inflating the wet-matured lung or the harvested lung with gas using the ventilator, and deflating the wet-matured lung or the harvested lung using the ventilator. The controller causes the ventilator to inflate or to deflate the wet-matured lung or the harvested lung to minimize the tracheal pressure fluctuation sensed by the tracheal pressure sensor.

In some implementations, minimizing any tracheal pressure fluctuation includes: providing a positive pressure manifold connected to the tracheal line and to a controller and providing a tracheal pressure sensor connected to the tracheal line and to the controller. The positive pressure manifold includes: a pressure reservoir, a gas source connected to the pressure reservoir, and a pressure release valve. The controller controls the compressor or the pressure release valve in response to data transmitted from the tracheal pressure sensor.

In certain implementations, the pressure reservoir is appropriately sized to minimize pressure fluctuation during inspiration and expiration.

In some implementations, the organ chamber further comprises a pneumatic pressure control module connected to the organ chamber. The pneumatic pressure control module: generates negative pressure in the organ chamber during an inspiration phase, maintains the organ chamber pressure for a plateau phase, and generates positive pressure in the organ chamber during an expiration phase.

In certain implementations, minimizing tracheal pressure fluctuation includes: providing a positive pressure manifold connected to the tracheal line and to a controller and providing a tracheal pressure sensor connected to the tracheal line and to the controller. The positive pressure manifold includes: a pressure reservoir, a gas source connected to the pressure reservoir, and a pressure release valve. The controller controls the compressor or the pressure release valve in response to data transmitted from the tracheal pressure sensor, and the organ chamber includes a pneumatic pressure control module connected to the organ chamber. The pneumatic pressure control module: generates negative pressure in the organ chamber during an inspiration phase, maintains the organ chamber pressure for a plateau phase, and generates positive pressure in the organ chamber during an expiration phase.

In some implementations, a functional lung is produced.

In certain implementations, the organ is a full lung or a vascularized portion thereof.

In some implementations, a subject having impaired or reduced lung capacity is treated by transplanting a lung described herein into the subject.

In certain implementations, cell media is perfused.

In certain implementations, fluid (e.g., cell media, liquid, or air) is perfused onto and/or into the organ matrix.

In some implementations, the decellularized lung tissue matrix, lung organ or harvested lung is (or is from, or is the size of) a human lung, or a lung from a pig, sheep, cow, horse, dog, cat, or other large mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, aspects, and advantages of the invention will be apparent from the description and drawings, and from the claims.

DESCRIPTION OF DRAWINGS

FIG. 11C are images an image showing the results of hematoxylin and eosin staining of porcine lung tissue after short-term ILC (scale bar, 250 µm).

FIG. 11D are images showing the results of a TUNEL assay of porcine lung tissue after short-term ILC. Nuclei and TUNEL positive cells are blue and green respectively (scale bar, 150 µm).

FIGS. 15A-B are graphs of physiological data associated with rat lung preservation under physiothermal conditions, perfused with 0.6 ml/min KHB. 15A is a bar graph showing the time course of PA perfusion pressure, demonstrating that the pressure decreased gradually. 15B is a bar graph showing that the dynamic compliance (Cdyn) also decreased over time. In this experiment, the isolated lung became edematous by 4 hours perfusion.

FIG. 15C is an image showing the results of staining a lung specimen after perfusion with hematoxylin and eosin. The left panel shows the control at 100×, while the right panel shows the sample after 6 hours of perfusion at 100×. This image shows maintenance of normal lung architecture and cellular integrity after 6 h of perfusion and ventilation of a cadaveric lung in the bioreactor.

DETAILED DESCRIPTION

Figure 1:
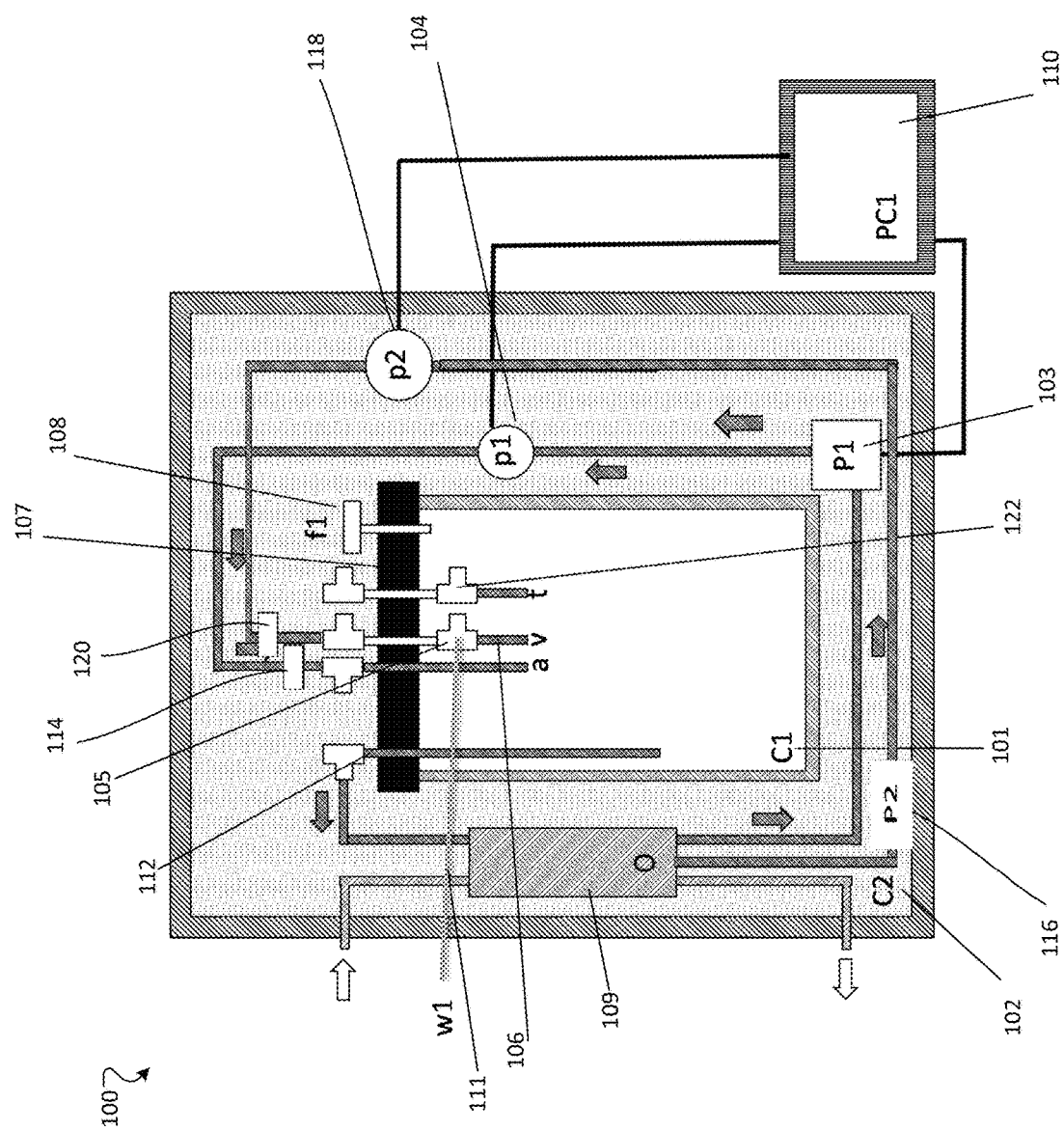
FIG. 1 is a schematic diagram of an exemplary perfusion lung bioreactor.

This document relates to methods and materials involved in airway organ generation and preservation. The present invention is based, at least in part, on the discovery of bioreactors configured to generate functional lung tissue that can be used to provide a more realistic environment for growth of functional airway organs ready for transplantation into humans and other animals. The lung tissue is generated over a given matrix, e.g., an artificial or decellularized lung tissue matrix. The present invention is further based on the use of this realistic environment for the preservation, repair, and modification of donor organs over prolonged periods of time in order to provide more, improved, and individualized grafts for transplantation.

As used herein, a "functional" lung tissue performs most or all of the functions of a normal healthy lung, e.g., allows for transportation of oxygen from the air into the bloodstream, and the release of carbon dioxide from the bloodstream into the air. It can humidify inhaled air, produce surfactant to decrease surface tension in the alveoli, and/or produce and transport mucus to remove inhaled particulate matter from the distal to the proximal airway.

As used herein, the terms "decellularized" and "acellular" are used or defined as the complete or near complete absence of detectable intracellular matter, endothelial cells, epithelial cells, and nuclei in histologic sections using standard histological staining procedures. Preferably, but not necessarily, residual cell debris also has been removed from the decellularized organ or tissue.

Decellularized Tissue/Organ Matrices

In some embodiments of the present methods, lung tissue is generated over a decellularized matrix. Methods and materials for a preparing a decellularized lung tissue matrix are known in the art, as discussed below. Any appropriate materials can be used to prepare such a matrix. In a preferred embodiment, a tissue matrix can be an acellular tissue scaffold developed from decellularized lung tissue. For example, tissue such as a human lung, e.g., one or a pair of human lungs or portions thereof, e.g., human, porcine, bovine, primate, or ovine cadaveric lungs or portions thereof, can be decellularized by an appropriate method to remove native cells from the tissue while maintaining morphological integrity and vasculature of the tissue or tissue portion and preserving extracellular matrix (ECM) proteins. Methods for decellularizing mammalian lung tissues are described, e.g., in O'Neill J D et al., Decellularization of human and porcine lung tissues for pulmonary tissue engineering. *Ann Thorac Surg.* 2013 September; 96(3):1046-55; Nichols J E et al., Production and assessment of decellularized pig and human lung scaffolds, *Tissue Eng Part A.* 2013 September; 19 (17-18):2045-62; Gilpin S E et al., Perfusion decellularization of human and porcine lungs: Bringing the matrix to clinical scale. *Journal of Heart and Lung Transplantation.* In press; Song J J et al., Bioartificial lung engineering. *Am J Transplant.* 2012 February; 12(2):283-8; and Ott H C et al., Regeneration and orthotopic transplantation of a bioartificial lung. *Nat Med.* 2010 August; 16(8):927-33 Exemplary decellularization methods can include subjecting tissue (e.g., lung tissue) to repeated freeze-thaw cycles, for example using liquid nitrogen. In other cases, a tissue can be subjected to an anionic or ionic cellular disruption medium such as sodium dodecyl sulfate (SDS), polyethylene glycol (PEG), or TritonX. The tissue can also be treated with a nuclease solution (e.g., ribonuclease, deoxyribonuclease) and washed in sterile phosphate buffered saline with mild agitation. Exemplary methods are known in the art e.g., O'Neill J D et al., Decellularization of human and porcine lung tissues for pulmonary tissue engineering. *Ann Thorac Surg.* 2013 September; 96(3):1046-55. In some cases, decellularization can be performed by flushing the vessels, ducts, and/or cavities of the organ or tissue using methods and materials known in the art. For example, as described in Maghsoudlou P et al., Preservation of micro-architecture and angiogenic potential in a pulmonary acellular matrix obtained using intermittent intra-tracheal flow of detergent enzymatic treatment. *Biomaterials.* 2013 September; 34(28):6638-48. Following the flushing step, the organ or tissue can be perfused via the line with a cellular disruption medium as described above for example 1% SDS in deionized water. Perfusion through the tissue can be anterograde or retrograde, and directionality can be alternated to improve perfusion efficiency. Depending upon the size and weight of an organ or tissue and the particular anionic or ionic detergent(s) and concentration of anionic or ionic detergent(s) in the cellular disruption medium, a tissue generally is perfused from about 2 to about 12 hours per gram of tissue with cellular disruption medium. Including washes, an organ may be perfused for up to about 12 to about 72 hours per gram of tissue. Perfusion generally is adjusted to physiologic conditions including flow rate and pressure, e.g., pressure between 5-100 mmHg, and flow rate between 0.1-10 times the physiologic cardiac output of the source organism or individual.

In another exemplary method, a decellularization method includes perfusing a detergent, e.g., (1) 0.1% SDS (2) 2%, sodium deoxycholate (SDC), or (3) 8 mmol/liter (3)3-[(3-cholamidopropyl)dimethylammonio]-1-propanesulfonate (CHAPS) (pH12) detergent, through the pulmonary artery at a constant pressure of 30 cm $H_2O$. The protocol for all 3 detergents includes:
1. a 10-minute initial antegrade wash with phosphate-buffered saline (PBS),
2. detergent perfusion for the time required to visualize an opaque translucent matrix (indicative of decellularization) plus an additional 20% of that initial time (e.g., 70 minutes+14 minutes),
3. 15-minute deionized $H_2O$ wash, and
4. an additional 172-hour PBS wash with added antibiotics and antimycotics. This decellularization method, e.g., can include an additional wash of 1% Triton-X following the deionized $H_2O$. The SDC protocol can include a 0.1% Triton-X perfusion before SDC and a 1 mol/liter NaCl wash after SDC.

Similarly, porcine and human lung decellularization methods can include perfusion of a detergent or other decellularization agent though the pulmonary artery at constant pressure, followed by sequential washing with $H_2O$, 1% Triton-X solution, and PBS. Similar to rat lungs, decellularization can be deemed complete upon visual inspection and the appearance of an opaque translucent matrix. Variability in the starting organ, mainly due to extensiveness of pre-flushing during harvest and any resulting clots can contribute to the required length of perfusion. In general, the time of decellularization perfusion can vary e.g., from 4 to 7 days.

Decellularized tissue can consist essentially (e.g., at least: 85% pure, 90% pure, 92% pure, 95% pure, 96% pure, 97% pure, 98% pure, and 99% pure by weight) of the extracellular matrix (ECM) component of all or most regions of the tissue, including ECM components of the vascular tree. ECM components can include any or all of the following: fibronectin, fibrillin, laminin, elastin, members of the collagen family (e.g., collagen I, III, and IV), glycosaminoglycans, ground substance, reticular fibers and thrombospondin, which can remain organized as defined structures such as the basal lamina. In a preferred embodiment, decellularized lung tissue matrix retains an intact vasculature. Preserving a substantially intact vasculature enables connection of the tissue matrix to a subject's vascular system upon transplantation. In addition, a decellularized tissue matrix can be further treated with, for example, irradiation (e.g., UV, gamma) to reduce or eliminate the presence of any type of microorganism remaining on or in a decellularized tissue matrix.

Methods for obtaining decellularized tissue matrices using physical, chemical, and enzymatic means are known in the art, see, e.g., Liao et al, *Biomaterials* 29(8):1065-74 (2008); Gilbert et al., *Biomaterials* 27(9):3675-83 (2006); Teebken et al., *Eur. J. Vasc. Endovasc. Surg.* 19:381-86 (2000). See also U.S. Pat. Publication Nos. 2009/0142836; 2005/0256588; 2007/0244568; and 2003/0087428.

Artificial Organ Matrices

In some embodiments of the present methods, lung tissue is generated over an artificial organ matrix. Methods and materials for a preparing an artificial organ matrix are known in the art. Any appropriate materials can be used to prepare such a matrix. In a preferred embodiment, an artificial organ matrix can be a scaffold developed from porous materials such as, for example, polyglycolic acid, Pluronic F-127 (PF-127), Gelfoam sponge, collagen-glycosaminoglycan (GAG), fibrinogen-fibronectin-vitronectin hydrogel (FFVH), and elastin. See, e.g., Ingenito et al., *J Tissue Eng Regen Med.* 2009 Dec. 17; Hoganson et al., *Pediatric*

Research, May 2008, 63(5):520-526; Chen et al., *Tissue Eng.* 2005 September-October; 11(9-10):1436-48. In some cases, an artificial organ matrix can have porous structures similar to alveolar units. See Andrade et al., *Am J Physiol Lung Cell Mol Physiol.* 2007 February; 292(2):L510-8. In some cases, an implanted artificial organ matrix can express organ-specific markers (e.g., lung-specific markers for Clara cells, pneumocytes, and respiratory epithelium). In some cases, an implanted artificial organ matrix can organize into identifiable structures (e.g., structures similar to alveoli and terminal bronchi in an artificial lung matrix). For example, an implanted artificial lung maxtrix made using FFVH can promote cell attachment, spreading and extracellular matrix expression in vitro and apparent engraftment in vivo, with evidence of trophic effects on the surrounding tissue. See Ingenito et al., supra. See also U.S. Pat. Nos. 7,662,409 and 6,087,552; United States Patent Publication Nos. 2010/0034791; 2009/0075282; 2009/0035855; 2008/0292677; 2008/0131473; 2007/0059293; 2005/0196423; 2003/0166274; 2003/0129751; 2002/0182261; 2002/0182241; and 2002/0172705.

Cadaveric Organs

The methods and devices described herein are also useful in maintaining and preparing cadaveric lungs for use in transplantation.

Methods and materials to isolate donor organs (e.g., lungs) from human and animal donors are known in the art. For example, described in Pasque M K et al. Standardizing thoracic organ procurement for transplantation. *J Thorac Cardiovasc Surg.* 2010 January; 139(1):13-7. and Bribriesco A C et al Experimental models of lung transplantation. *Front Biosci* (Elite Ed). 2013 Jan. 1; 5:266-72. Any appropriate method to isolate these can be used. These donor organs can be maintained using the bioreactors described herein for a time sufficient to prepare a recipient for transplant, for a time sufficient to transport the organ to the recipient, or for a time sufficient to maintain the organ under conditions that facilitate the repair of the entire organ or portion thereof so that it is suitable for implantation.

In some embodiments, donor organs from human organ donors can be modified to remove endothelial lining and subsequently reseeded with recipient-derived endothelial cells to minimize immunogenicity. For example, this can be accomplished by osmotic challenge via perfusion with deionized water, perfusion with low detergent concentrations such as 0.05% Polidocanol, or perfusion with enzyme solutions such as DNAse, or collagenase. Donor organs found unsuitable for immediate transplantation due to infection, physical damage such as trauma, or ischemic damage due to prolonged hypoperfusion, or damage due to donor conditions such as brain death can be repaired using the devices and methods described herein (e.g., by mounting, perfusing, and repairing using antibiotics, cells, growth factor stimulation, and anti-inflammatory treatment). Animal-derived organs can be rendered less immunogenic by genetic and cellular modification.

In some cases, donor lungs may exhibit radiographic or bronchoscopic evidence of infection. In order to control bioburden and other sources of potential infections, lungs can be mounted, e.g., on devices described herein, and flushed with antibiotic and aseptic solutions through both the vasculature and the trachea. The solution can then be suctioned from the donor lung, e.g., using bronchoscopy. This flushing procedure can be performed both before and during culture. In certain cases, a pulmonary embolism before death or blood clotting after cardiac arrest may occur, resulting in a risk of clot formation. Isolated donor organs can be mounted and retrogradely flushed via pulmonary veins to remove the clot and/or can be perfused with a thrombolytic substances to lyse any possible clot. In some cases, the donor organ may contain high levels of inflammatory cytokines and/or an inflammatory state in the alveolar macrophages in the donor lungs often related to brain death in the donor (Venkateswaran R V et al., The proinflammatory environment in potential heart and lung donors: prevalence and impact of donor management and hormonal therapy. *Transplantation.* 2009 Aug. 27; 88(4):582-8). These lungs can be treated with (e.g., perfused with) anti-inflammatory drugs before and/or during organ culture. In certain cases, drugs specifically targeted at the inflammatory-cell type may be perfused. This inflammatory state can also lead to capillary leakage and increased tissue water in the donor organ as described in, for example, Venkateswaran R V et al., Measurement of extravascular lung water following human brain death: implications for lung donor assessment and transplantation. *Eur J Cardiothorac Surg.* 2013 June; 43(6):1227-32. During the preservation period the organ can be perfused with hyperosmolar solutions to draw tissue water back into the vascular space and thereby restore a healthier fluid balance, and normal lung compliance.

In some cases, preservation solutions may also be administered to the lung via the devices described herein to reduce the risk of graft failure. In some examples, the preservation fluid may include low-potassium extracellular-type solutions such as Perfadex® or a composition as shown in Table 1. Amino acids, antibiotics, or agents (e.g., those shown in Table 2) may also be added to the preservation solution.

TABLE 1

| Perfusate Composition |
| --- |
| Krebs-Henseleit Buffer (118 mM NaCl, 4.7 mM KCl, 1.2 mM KH2PO4, 1.2 mM MgSO4, 4.2 mM NaHCO3) |
| 0.2%-5% D-Glucose |
| 1-15% human Albumin (optional) |
| 1-20% Hetastarch (optional) |
| 1-10% Dextan 40 |
| Varying concentrations of Glutamine, Antibiotics, and amino acids |

TABLE 2

| Perfusate Composition |
| --- |
| ROS scavenger (Glutathione/N-acetylcysteine) |
| $2^{nd}$ messenger (dibutryl cAMP (cAMP analogue)) |
| Glucose metabolism (Insulin) |
| Membrane stabilizer (Hydrocortisone) |
| Growth factors (VEGF, FGF) |
| Oxygen carrier (red blood cells, perfluorocarbon, hemoglobin binding oxygen carrier) |

In some cases, donor lungs may exhibit evidence of damage resulting from a varieties of factors, e.g., quality of the donor lung, the type of preservation solution, length of time between harvest and culture, and so forth. In order to reduce and/or eliminate the degree of damage the donor lungs and/or portions thereof can be mounted, e.g., on devices described herein, and ventilated liquid and/or dry ventilation. In an example, air is perfused over the tracheal line, while the ventricular and/or arterial lines are perfused with a solution that mimics physiologic parameters, e.g., physiologic saline solution, blood containing solution, and/or a preservation solution. The donor lungs may remain mounted until the donor lungs are needed for transplant and/or until the damaged donor lungs exhibit re-epithelialization and exhibit improved endothelial barrier function. These perfusion methods can be combined with the cellular seeding methods, as described below.

Cell Seeding

In some of the methods described herein, a lung tissue matrix, e.g., decellularized lung tissue matrix or artificial lung matrix, is seeded with cells, e.g., differentiated or regenerative cells.

Any appropriate regenerative cell type, such as naïve or undifferentiated cell types, can be used to seed the lung tissue matrix. The cells may be seeded at a variety of stages including, but not limited to, stem cell stage (e.g., after induction), progenitor cell stage, hemangioblast stage, or differentiated stage (e.g., CD 31+, vWF+). As used herein, regenerative cells can include, without limitation, progenitor cells, precursor cells, and "adult"-derived stem cells including umbilical cord cells (e.g., human umbilical vein endothelial cells) and fetal stem cells. Regenerative cells also can include differentiated or committed cell types. Stem cells appropriate for the methods and materials provided herein can include human induced pluripotent stem cells (iPSC) (e.g., undifferentiated, differentiated endoderm, anteriolized endoderm, TTF-1 positive lung progenitors), human mesenchymal stem cells, human umbilical vein endothelial cells, multipotent adult progenitor cells (MAPC), iPS derived mesenchymal cells, or embryonic stem cells. In some cases, regenerative cells derived from other tissues also can be used. For example, regenerative cells derived from skin, bone, muscle, bone marrow, synovium, or adipose tissue can be used to develop stem cell-seeded tissue matrices.

In some cases, a lung tissue matrix provided herein can be alternatively or further seeded with differentiated cell types such as (preferably human) epithelial cells and endothelial cells. For example, a lung matrix can be seeded with endothelial cells via the vasculature (e.g. through the arterial line or the venous line), and seeded with epithelial cells via the airway (e.g., through the tracheal line). The lung matrix can also be seeded with one or more cell types (e.g., one or more of types of epithelial and mesenchymal cells, adult peripheral blood derived epithelial cells, cord blood-derived epithelial cells, iPS derived epithelial cells, progenitor stage cells (e.g., smooth muscle), adult lung derived cell mixture (e.g., rat human), commercially available small airway epithelial cells or alveolar epithelial cells, Embryonic Stem (ES) cell-derived epithelial cells, and/or human umbilical vein endothelial cells (HUVEC).

Any type of appropriate commercially available media and/or media kits may be used for the seeding and culture of cells. For example, SAGM media may be used for small airway cells (e.g., SAGM BulletKit by Lonza) and EGM-2 kits may be used for endothelial cells (e.g., EGM-2 BulletKit by Lonza). Media customized to the seeded endothelial cell type may be used (e.g., by increasing or decreasing growth factors such as VEGF) as described in, for example, Brudno Y et al. Enhancing microvascular formation and vessel maturation through temporal control over multiple pro-angiogenic and pro-maturation factors. *Biomaterials* 34 (2013) 9201-9209. In the case of endothelial cells, a sequence of different media compositions may be used to induce different phases of seeding, expansion, engraftment, and maturation of cells. For example, in a first phase, a cell seeded constructs may be perfused with an 'angiogenic media' for 2-30 days to increase endothelial cell expansion, migration, and metabolism. This media is characterized by high concentration of cytokines, e.g., VEGF at 5-100 ng/ml and bFGF at 5-100 ng/ml, and the presence of phorbol myristate acetate (PMA), e.g., 5-100 ng/ml PMA, which activates the angiogenic pathway through activation of protein kinase C, and Ang-1, which stimulates endothelial cell sprouting. In a second phase, a cell seeded construct can then be perfused with 'tightening media' that supports endothelial maturation and the formation of tight junctions. Tightening media has lower levels of cytokines, with the same basic composition as the angiogenic media but with decreased levels of VEGF, bFGF and PMA (0.1-5 ng/ml VEGF, FGF, and PMA). Hydrocortisone, which promotes tight junction formation and has been shown to reduce pulmonary edema, can be further added to the tightening media to promote vascular maturation. Further promaturation factors such as PDGF and Ang-2 may be added to the tightening media to enhance vessel formation. Concentrations of these factors may be titrated to support different vessel sizes. Media changes can be performed gradually to avoid detrimental effects of sudden cytokine changes. Similar to endothelial cell supporting media, sequential media changes can be used to guide epithelial cell fate. Initial media may contain, for example, Activin A at 10-200 ng/ml and Pi3K inhibitors such as ZSTK 474 at 0.01-1 uM to induce definite endoderm, subsequently TGF-beta inhibitors such as A-8301 at 01-10 uM and BMP4 antagonists such as DMH-1 at 0.05-1 uM to induce anteriorized endoderm, and finally BMP4 at 1-100 ug/ml, FGF2 at 10-500 ng/ml, GSK-3beta inhibitor such as CHIR 99021 at 10-500 nM, a PI3K inhibitor such as PIK-75 at 1-100 nM and methotrexate at 1-100 nM to induce the generation of lung progenitor cells.

Any appropriate method for isolating and collecting cells for seeding can be used. For example, induced pluripotent stem cells generally can be obtained from somatic cells "reprogrammed" to a pluripotent state by the ectopic expression of transcription factors such as Oct4, Sox2, Klf4, c-MYC, Nanog, and Lin28. See Takahashi et al., *Cell* 131:861-72 (2007); Park et al., *Nature* 451:141-146 (2008); Yu et al., *Science* 318:1917-20 (2007); Zhu et al., *Cell Stem Cell.* 7:651-5 2010; and Li et al., *Cell Res.* 21:196-204 (2011); Malik and Rao, Methods Mol Biol. 2013; 997:23-33; Okano et al., Circ Res. 2013 Feb. 1; 112(3):523-33; Lin and Ying, Methods Mol Biol. 2013; 936:295-312. Peripheral blood-derived mononuclear cells can be isolated from patient blood samples and used to generate induced pluripotent stem cells. In other examples, induced pluripotent stem cells can be obtained by reprograming with constructs optimized for high co-expression of Oct4, Sox2, Klf4, c-MYC in conjunction with small molecule such as transforming growth factor β (SB431542), MEK/ERK (PD0325901) and Rho-kinase signaling (Thiazovivin). See GroB et al., *Curr Mol Med.* 13:765-76 (2013) and Hou et al., *Science* 341:651:654 (2013). Methods for generating endothelial cells from stem cells are reviewed in Reed et al., Br J Clin Pharmacol. 2013 April; 75(4):897-906. Cord blood stem cells can be isolated from fresh or frozen umbilical cord blood. Mesenchymal stem cells can be isolated from, for example, raw unpurified bone marrow or ficoll-purified bone marrow. Epithelial and endothelial cells can be isolated and collected from living or cadaveric donors, e.g., from the subject who will be receiving the bioartificial lung, according to methods known in the art. For example, epithelial cells can be obtained from a skin tissue sample (e.g., a punch biopsy), and endothelial cells can be obtained from a vascular tissue sample. In some embodiments, proteolytic enzymes are perfused into the tissue sample through a catheter placed in the vasculature. Portions of the enzymatically treated tissue can be subjected to further enzymatic and mechanical disruption. The mixture of cells obtained in this manner can be separated to purify epithelial and endothelial cells. In some cases, flow cytometry-based methods (e.g., fluorescence-activated cell sorting) can be used to sort cells based on the presence or absence of specific cell surface markers. Furthermore, lung cells (epithelial, mesenchymal, and endothelial) can be obtained from lung biopsies, which can be obtained via transbronchial and endobronchial biopsies or via surgical biopsies of lung tissue. In cases where non-autologous cells are used, the selection of immune type-matched cells should be considered, so that the organ or tissue will not be rejected when implanted into a subject.

Isolated cells can be rinsed in a buffered solution (e.g., phosphate buffered saline at pH 7.4) and resuspended in a cell culture medium. Standard cell culture methods can be used to culture and expand the population of cells. Once obtained, the cells can be used to seed the tissue matrix, e.g., introduced into the matrix via the arterial or venous lines (endothelial cells) or through the airway (tracheal) line (epithelial cells). For example, a tissue matrix can be seeded with at least one cell type in vitro at any appropriate cell density. For example, cell densities for seeding a matrix can be at least $1 \times 10^3$ cells/gram matrix. Cell densities can range between about $1 \times 10^5$ to about $1 \times 10$ cells/gram matrix (e.g., at least 100,000, 1,000,000, 10,000,000, 100,000,000, 1,000,000,000, or 10,000,000,000 cells/gram matrix) can be used.

In some cases, a decellularized or artificial lung tissue matrix, as provided herein, can be seeded with the cell types and cell densities described above by perfusion seeding. For example, a flow perfusion system can be used to seed the decellularized lung tissue matrix via the vascular system preserved in the tissue matrix (e.g., through the arterial line). In some cases, automated flow perfusion systems can be used under the appropriate conditions. Such perfusion seeding methods can improve seeding efficiencies and provide more uniform distribution of cells throughout the composition. Quantitative biochemical and image analysis techniques can be used to assess the distribution of seeded cells following either static or perfusion seeding methods.

In some cases, a tissue matrix can be impregnated with one or more growth factors to stimulate differentiation of the seeded regenerative cells. For example, a tissue matrix can be impregnated with growth factors appropriate for the methods and materials provided herein, for example, vascular endothelial growth factor (VEGF), TGF-β growth factors, bone morphogenetic proteins (e.g., BMP-1, BMP-4), platelet-derived growth factor (PDGF), basic fibroblast growth factor (b-FGF), e.g., FGF-10, insulin-like growth factor (IGF), epidermal growth factor (EGF), or growth differentiation factor-5 (GDF-5). See, e.g., Desai and Cardoso, Respire. Res. 3:2 (2002). These growth factors can be encapsulated to control temporal release. Different parts of the scaffold can be enhanced with different growth factors to add spatial control of growth factor stimulation.

Seeded tissue matrices can be incubated for a period of time (e.g., from several hours to about 14 days or more) post-seeding to improve fixation and penetration of the cells in the tissue matrix. The seeded tissue matrix can be maintained under conditions in which at least some of the regenerative cells can multiply and/or differentiate within and on the acellular tissue matrix. Such conditions can include, without limitation, the appropriate temperature (35-38 degree centigrade) and/or pressure (e.g., atmospheric), electrical and/or mechanical activity (e.g., ventilation via positive or negative pressure with positive end expiratory pressure from 1-20 cmH2O, mean airway pressure from 5-50 cmH2O, and peak inspiratory pressure from 5-65 cmH2O), the appropriate amounts of fluid, e.g., $O_2$ (1-100% FiO2) and/or $CO_2$ (0-10% FiCO2), an appropriate amount of humidity (10-100%), and sterile or near-sterile conditions. Such conditions can also include wet ventilation, wet to dry ventilation and dry ventilation. In some cases, nutritional supplements (e.g., nutrients and/or a carbon source such as glucose), exogenous hormones, or growth factors can be added to the seeded tissue matrix. Histology and cell staining can be performed to assay for seeded cell propagation. Any appropriate method can be performed to assay for seeded cell differentiation. In general, the methods described herein will be performed in an airway organ bioreactor apparatus, e.g., as described herein.

Thus, the methods described herein can be used to generate a transplantable bioartificial lung tissue, e.g., for transplanting into a human subject. As described herein, a transplantable tissue will preferably retain a sufficiently intact vasculature that can be connected to the patient's vascular system.

The bioartificial lung tissues described herein can be combined with packaging material to generate articles of manufacture or kits. Components and methods for producing articles of manufacture are well known. In addition to the bioartificial tissues, an article of manufacture or kit can further can include, for example, one or more anti-adhesives, sterile water, pharmaceutical carriers, buffers, and/or other reagents for promoting the development of functional lung tissue in vitro and/or following transplantation. In addition, printed instructions describing how the composition contained therein can be used can be included in such articles of manufacture. The components in an article of manufacture or kit can be packaged in a variety of suitable containers.

Methods for Using Bioartificial Lungs

This document also provides methods and materials for using bioartificial lung tissues and, in some cases, promoting lung function. In some embodiments, the methods provided herein can be used to restore some lung function in patients having diseases that impair or reduce lung capacity (e.g., cystic fibrosis, COPD, emphysema, lung cancer, asthma, pulmonary hypertension, lung trauma, or other genetic or congenital lung abnormalities, e.g., bronchogenic cyst, pulmonary agenesis and hypoplasia, polyalveolar lobe, alveolocapillary dysplasia, sequestration including arteriovenous malformation (AVM) and scimitar syndrome, pulmonary lymphangiectasis, congenital lobar emphysema (CLE), and cystic adenomatoid malformation (CAM) and other lung cysts). The methods provided herein also include those wherein the subject is identified as in need of a particular stated treatment, e.g., increased lung function, or increased or improved lung capacity.

Bioartificial lung tissues (e.g., whole organs or portions thereof) can be generated according to the methods provided herein. In some embodiments, the methods comprise transplanting a bioartificial lung tissue as provided herein to a subject (e.g., a human patient) in need thereof. In some embodiments, a bioartificial lung tissue is transplanted to the site of diseased or damaged tissue. For example, bioartificial lung tissues can be transplanted into the chest cavity of a subject in place of (or in conjunction with) a non-functioning or poorly-functioning lung; methods for performing lung transplantation are known in the art, see, e.g., Boasquevisque et al., Surgical Techniques: Lung Transplant and Lung Volume Reduction, *Proceedings of the American Thoracic Society* 6:66-78 (2009); Camargo et al., Surgical maneuvers for the management of bronchial complications in lung transplantation, *Eur J Cardiothorac Surg* 2008;

34:1206-1209 (2008); Yoshida et al., "Surgical Technique of Experimental Lung Transplantation in Rabbits," *Ann Thorac Cardiovasc Surg.* 11(1):7-11 (2005); Venuta et al., Evolving Techniques and Perspectives in Lung Transplantation, Transplantation Proceedings 37(6):2682-2683 (2005); Yang and Conte, *Transplantation Proceedings* 32(7):1521-1522 (2000); Gaissert and Patterson, Surgical Techniques of Single and Bilateral Lung Transplantation in The Transplantation and Replacement of Thoracic Organs, 2d ed. Springer Netherlands (1996).

The methods can include transplanting a bioartificial lung or portion thereof as provided herein during a surgical procedure to partially or completely remove a subject's lung and/or during a lung resection. The methods can also include harvesting a lung or a portion thereof from a live donor or cadaver and preserving or regenerating the lung in a bioreactor described herein. In some cases, the methods provided herein can be used to replace or supplement lung tissue and function in a subject, e.g., a human or animal subject.

Any appropriate method(s) can be performed to assay for lung function before or after transplantation. For example, methods can be performed to assess tissue healing, to assess functionality, and to assess cellular in-growth. In some cases, tissue portions can be collected and treated with a fixative such as, for example, neutral buffered formalin. Such tissue portions can be dehydrated, embedded in paraffin, and sectioned with a microtome for histological analysis. Sections can be stained with hematoxylin and eosin (H&E) and then mounted on glass slides for microscopic evaluation of morphology and cellularity. For example, histology and cell staining can be performed to detect seeded cell propagation. Assays can include functional evaluation of the transplanted tissue matrix or imaging techniques (e.g., computed tomography (CT), ultrasound, or magnetic resonance imaging (e.g., contrast-enhanced MRI)). Assays can further include functional tests under rest and physiologic stress (e.g., body plethysmography, lung function testing). Functionality of the matrix seeded with cells can be assayed using methods known in the art, e.g., histology, electron microscopy, and mechanical testing (e.g., of volume and compliance). Gas exchange can be measured as another functionality assay. To assay for cell proliferation, thymidine kinase activity can be measured by, for example, detecting thymidine incorporation. In some cases, blood tests can be performed to evaluate the function of the lungs based on levels of oxygen in the blood.

To facilitate functionality assays during culture, any line of the bioreactor apparatus' described herein may include sampling ports to allow for single or real-time measurements of functionality parameters (e.g., pH, glucose, lactate, Na, K, Ca, Cl, bicarb, $O_2$, $CO_2$, sat). Metabolites may also be used to monitor cell number and viability using colorimetric assays, and biochemical assays may be used to monitor cell maturation (e.g., measuring surfactant protein, etc.) For example, an increased concentration of surfactant can indicate that the culture lung possesses sufficient epithelial cells to withstand dry ventilation. In some cases, endothelial barrier function may be used as a marker of vascular maturity. Lungs can be perfused with different sizes of molecules (such as dextrans of defined sizes and albumin), and microbeads (increasing sizes from 0.2 to 5 um), as well as isolated red blood cells. Bronchoalveolar lavage fluid can then be sampled to assess leakage of these markers into the alveolar space. For example, 500-kDa dextran can be used in combination with a Bronchoalvelar lavage assay to determine the percentage of dextran retained within the vascular compartment. An increase in the percentage of dextran retained indicates an improvement in the barrier function because barrier function to dextran is dependent on viable and functional endothelium, while dextran will diffuse across a denuded vascular basement membrane (e.g., in an acellular lung) over time during constant perfusion. For example, a cadaveric lung may retain substantially all of the dextran within the vascular compartment while acellular lungs may retain a small percentage of the dextran (e.g., 10.0%±8.0%). Leakage of these markers into the alveolar space greater than a tolerated minimum (for example >10% of 4 um microbeads, or greater than 20% of 0.2 um microbeads) can be used to indicate that the lung is not sufficiently mature to withstand dry ventilation.

In some cases, molecular biology techniques such as RT-PCR can be used to quantify the expression of metabolic (e.g. surfactant protein, mucin-1) and differentiation markers (e.g. TTF-1, p63, surfactant protein C). Any appropriate RT-PCR protocol can be used. Briefly, total RNA can be collected by homogenizing a biological sample (e.g., tendon sample), performing a chloroform extraction, and extracting total RNA using a spin column (e.g., RNeasy® Mini spin column (QIAGEN, Valencia, CA)) or other nucleic acid-binding substrate. In other cases, markers associated with lung cells types and different stages of differentiation for such cell types can be detected using antibodies and standard immunoassays.

Airway Organ Bioreactor Apparatus

An exemplary airway organ bioreactor is presented in FIG. 1. Throughout the specification, a lung will be offered as an example of an airway organ. Other examples can include a portion of a lung that includes a hierarchal vasculature structure, e.g., a lobe or a segment. Exemplary bioreactors capable of supporting a harvested lung from a live donor or cadaver are presented in FIGS. 8 and 9. Any of the bioreactors described herein can be configured to permit culture of a lung in a supine position.

Referring to FIG. 1, components of the bioreactor 100 include a lung chamber 101, an incubator chamber 102, an arterial perfusion pump 103, an arterial pressure 104, an arterial line 105, a venous line 106, a tracheal line 107, a filter 108, an oxygenator 109, an egress line 112, a control module 110, a venous valve 111, an arterial flow sensor 114, a venous perfusion pump 116, a venous pressure sensor 118, a venous flow sensor 120, and a tracheal valve 122. At least the lung chamber 101 is enclosed within the incubator chamber 102 to maintain the appropriate temperature and humidity.

The bioreactor 100 permits constant pressure perfusion (with oxygenated media) through the pulmonary artery, pulmonary vein, or another appropriate passage with oxygenated media. Lung chamber 101 holds a lung (not shown). The pulmonary artery of lung is connected to the pulmonary arterial line 105, the pulmonary vein of the lung is connected to venous line 106, and the trachea of the lung is connected to the tracheal line 107. The bioreactor 100 is a neutral pressure ventilation system because sterile filter 108 equilibrates pressure in the lung chamber 101 with the pressure of incubator chamber 102, while the tracheal line 107 is also equilibrated with the pressure of the incubator because tracheal valve 122 is generally open.

Within lung chamber 101, the cell matrix is perfused antegradely with a cells and media in order to allow seeding of cells to grow in the lung matrix. The perfusion takes place through the arterial line 105 to the pulmonary artery and through the venous line to the pulmonary vein while the tracheal valve 122 remains open. This configuration permits the cells and media to reach the capillary bed from both the arterial and venous sides and permits the media to diffuse through the acellular basement membrane and exit the matrix via the trachea or across the pleura.

The arterial flow sensor 114 and the venous flow sensor 120 are sensors capable of measuring the flow rate of these lines (e.g., transonic flow probes). Flow rate sensors may be incorporated into any fluid line within any of the bioreactors described herein (e.g., any ingress or egress line, arterial line, venous line, tracheal line, or oxygen exchange line). In certain embodiments, the flow rate may also be calculated based on the diameter of the tubing and the speed of the associated pumps.

The cells and/or media flow through the arterial line 104 and the venous line 107 through the pulmonary vasculature. To recirculate the media passes through the oxygenator 109. The oxygenated media then flows to the arterial perfusion pump 103 or venous perfusion pump 116 that circulate the media through the bioreactor 100. This pump is controlled by the control module 110 that controls the speed of the perfusion pump 104 and the venous pump 116 speed based on the pressure readings from the arterial pressure sensor 104 and the venous pressure sensor 118 respectively. Arterial and venous perfusion pressures can be modified based on the size and number of cells in order to optimize cell delivery. The control module 110 is also capable of recording data (e.g., resistance readings from arterial pressure sensor 104, and venous pressure sensor 118. The media completes the circuit, returning to the arterial line 104 and/or to the venous line 106. During initial anterograde seeding, media diffuses through the lung matrix before it or as it reaches the capillary bed. To guide media through the scaffold, the tracheal valve 122 can be opened or closed to modify the pressure within the lung thereby guiding the media through the scaffold. In some cases, retrograde seeding can be used. In these cases, the cells and/or media flow through the venous line 107, and the oxygenated media flows to the venous perfusion pump 116, which circulates the media through the bioreactor 100. As with anterograde seeding, to guide media through the scaffold, the tracheal valve 122 can be opened or closed to modify the pressure within the lung thereby guiding the media through the scaffold.

After the vasculature resistance of the lung, matrix is sufficient to withstand physiological conditions (e.g., vascular resistance increases due to the reendothelialization of the lung matrix), the bioreactor 100 switches to anterograde perfusion. The vasculature resistance is measured by the arterial pressure sensor 104 over time. As the vascular system is populated, the diffusion across the vascular membrane decreases causing an increase in the pressure measured by the arterial sensor 104 (i.e., an increase in vascular resistance). In some examples, particles are perfused through the bioreactor 100 and their progress is monitored to determine the diffusion rate across the vascular membrane.

Figure 2:
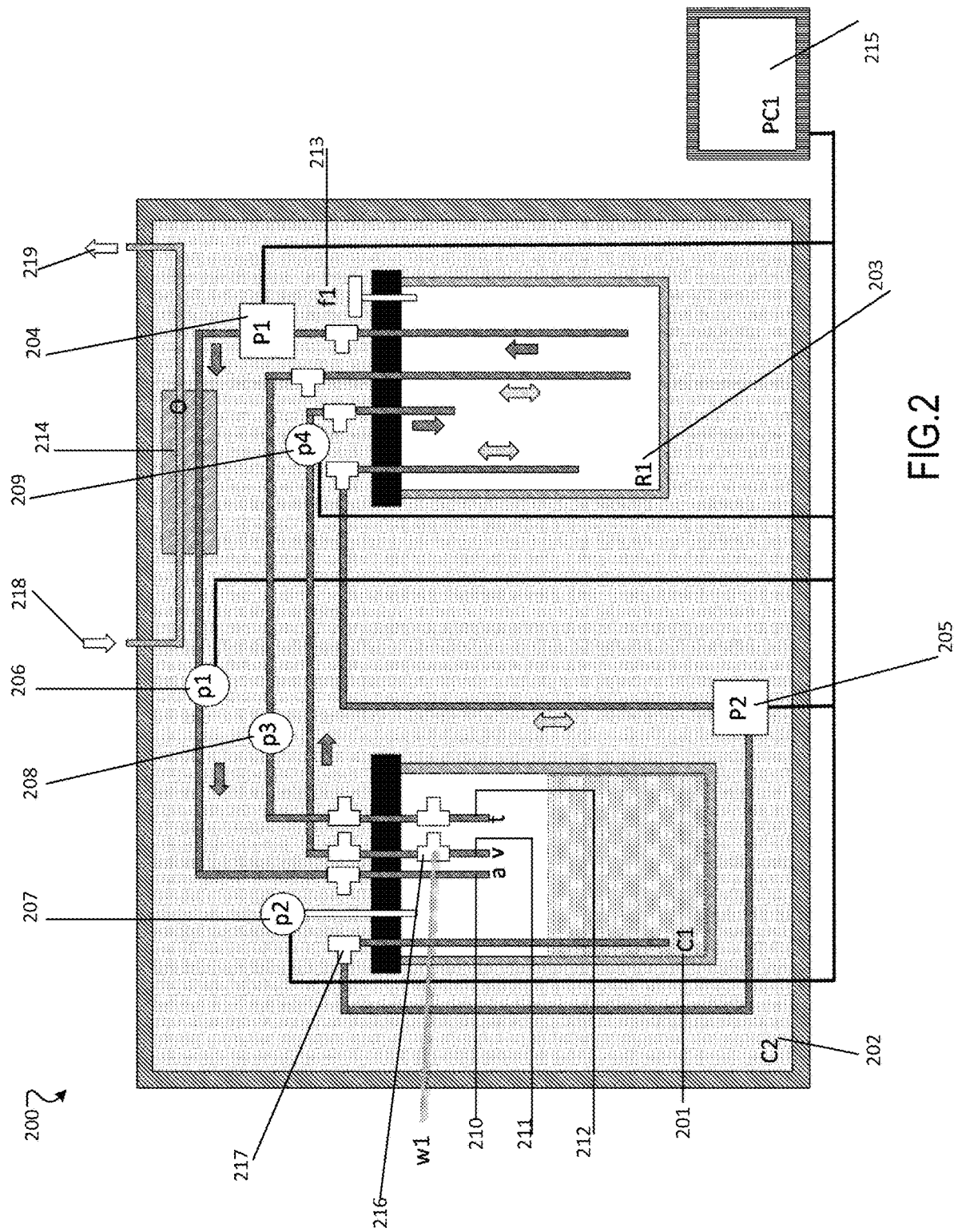
FIG. 2 is a schematic diagram of an exemplary lung bioreactor configured to provide negative pressure wet ventilation with a perfusion system.

Referring to FIG. 2, components of the bioreactor 200 include a lung chamber 201, an incubator chamber 202, a media reservoir 203, an arterial perfusion pump 204, a drainage pump 205, an arterial pressure sensor 206, a chamber pressure sensor 207, a tracheal pressure sensor 208, a venous pressure sensor 209, an arterial line 210, a venous line 211, a tracheal line 212, a filter 213, an oxygenator 214, a control module 215, and a venous valve 216, a tracheal valve 212, and an egress line 217. The lung chamber 201 is enclosed within the incubator chamber 202 to maintain the appropriate temperature and humidity.

Still referring to FIG. 2, the bioreactor 200 combines a flow perfusion system and negative pressure ventilation. A lung matrix is placed in lung chamber 202. The flow perfusion system uses the arterial line 210 connected to the pulmonary artery of the lung. The media is aspirated from the media reservoir 203 and passes through the oxygenator 214. The oxygenator 214 exchanges air, e.g., from an entrance point 218 and an exit point 219, with the environment surrounding the incubator chamber 202. After passing through the oxygenator 214, arterial pressure sensor 206 records the arterial pressure and transmits this data to the control module 215. The arterial pressure reading then regulates the roller pump that pumps media from the reservoir to the pulmonary artery. The media then circulates out of the lung chamber 201 through an egress line 217 and is pumped using the drainage pump 205 into the media reservoir 203. The drainage pump 205 is bi-directional and can be used to circulate media between the media reservoir 203 to the lung chamber 201. This recirculation also helps to maintain the correct pH in the lung chamber 201. Control module 215 controls the drainage pump 205, e.g., speed and/or direction, based on pressure readings recorded by the chamber pressure sensor 207. As the chamber pressure in lung chamber 201 fluctuates, liquid flows in and out of the tracheal line 212. Because the venous line 211 is open to the media reservoir 203, the venous pressure equilibrates to the chamber pressure thus preventing a transpulmonary pressure gradient that can cause fluid to flow from the artery into the tissue. By monitoring the chamber pressure and pumping accordingly, the media level in the lung chamber 201 can be maintained.

During negative pressure wet ventilation, fluid enters and exits the lung matrix causing the pressure in the lung chamber 201 to fluctuate. This fluctuation also expands and contracts the lung matrix. This expansion causes repetitive liquid movement in and out of the trachea and fluid shifts through the lung matrix (e.g., through the pulmonary vein and lymphatic vessels) into the lung chamber 201. These fluid shifts can vary throughout the culture period and can result in unstable culture conditions, an undesired increase in chamber pressure, media overflow, the failure of negative pressure ventilation, and the damage of the lung or lung graft. Monitoring the lung chamber 201 pressure using the chamber pressure sensor 207 allows the control module 215 to correct for these fluid shifts by appropriately adjusting the direction and duration of the drainage pump 205. For example, as the media volume in the lung chamber 201 increases, an increase in pressure is sensed by the chamber pressure sensor 207. This data is transmitted to the control module 215, which activates the perfusion pump 205 for a sufficient duration to return excess media from the lung chamber 201 to the media reservoir 203 until desired pressure is restored.

As shown in FIG. 2, the bioreactor 200 also includes the tracheal pressure sensor 208 and the venous pressure sensor 209. The tracheal pressure sensor 208 measures pressure within the airway (e.g., the trachea). The tracheal line 212 is connected to the media reservoir 203 by the tracheal valve 221 and the pressure within the tracheal line 212 equilibrates with the pressure within the media reservoir 203. To limit the airway pressure to a physiologic range, the height of the media reservoir 203 may be raised to modify the generated positive airway pressure. As the chamber pressure decreases, the tracheal pressure will also, to a lesser extent, decrease.

The bioreactor 200 can also use the venous pressure sensor 209 to actively monitor the media exchange rate between the venous line 212 and the media reservoir 203. The venous after load into the system is controlled by the level of the reservoir when valve 216 is closed, or by a resistance valve that can be attached to venous valve 216 if it is open position. For example, the venous valve 216 is generally in an open position. A low-pressure reading (e.g., <−5 mmHg) may trigger the venous valve 216 to close (e.g., automatically or by an operator) thus providing more venous backpressure to prevent post-capillary vascular collapse. If the pressure reading is high (e.g. >20 mm Hg, the venous valve 216 can open to reduce the venous afterload and minimize fluid shifts into the interstitial space and airways.

Still referring to FIG. 2, the pressure in the media chamber 203 is equilibrated with the ambient environment (e.g., the incubator chamber) through the sterile filter 213. This exchange also permits the exchange of gasses (e.g., carbon dioxide) between the incubator chamber 202 and the media reservoir 203, which helps maintain the appropriate pH values of the media in the system. The height of the media reservoir 203 may be adjusted relative to the height of the lung chamber 201. This causes a positive wet respiratory pressure and affects the tracheal airway pressure in relation to the lung. For example, the media reservoir 203 is set at 4 cm above the lung submerged in the media. This causes a positive airway pressure.

Generally, the pressure recorded by any of the sensors described herein is within physiological ranges depending on the organ cultured. For example, the arterial ranges may be a mean of 10-35 mmHg, the lung chamber 201 may be between a mean of −40 to 40 mmHg.

Figure 3:
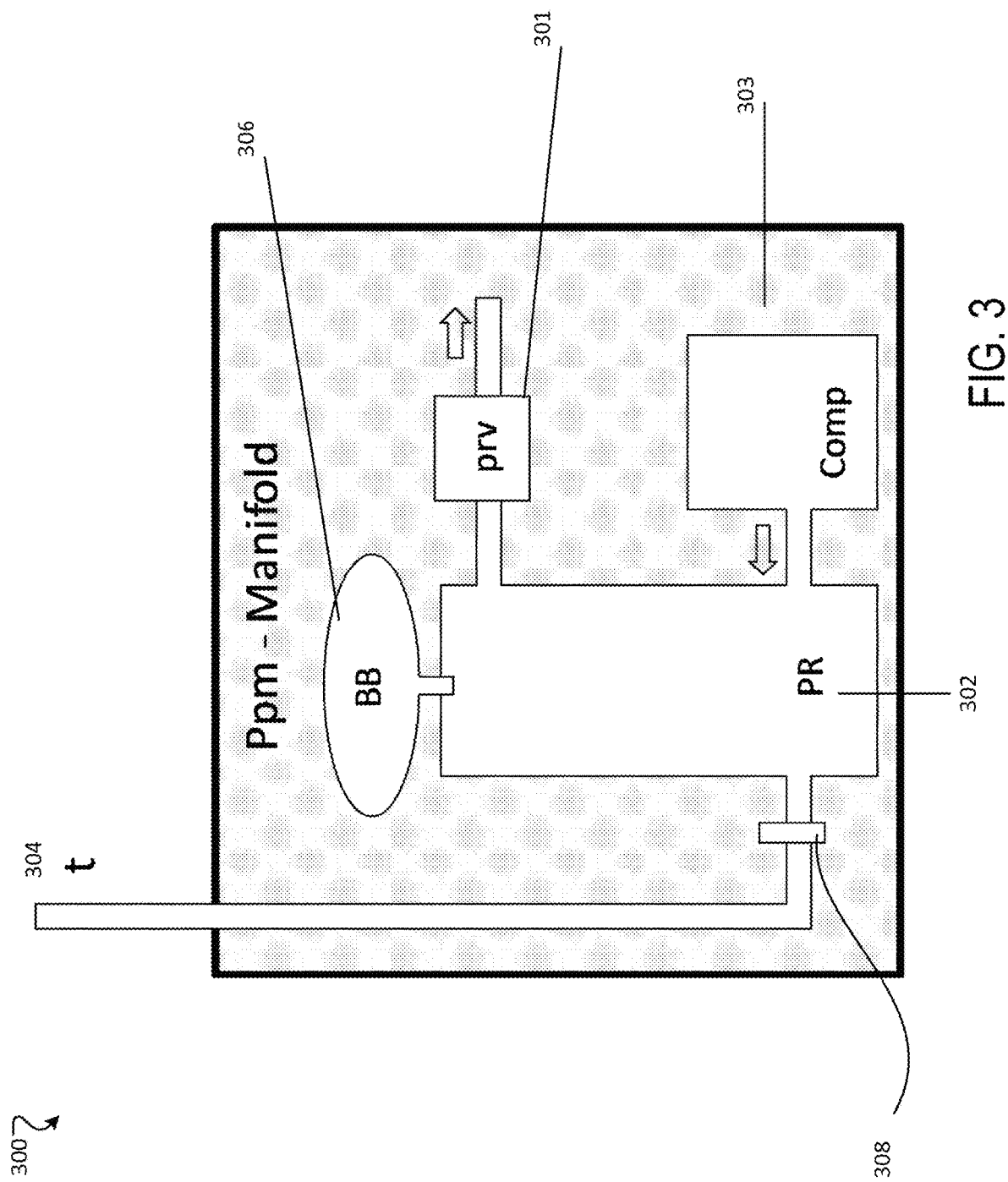
FIGS. 3-3a are schematic diagrams of an exemplary positive pressure manifold represented in FIG. 4.

Referring to FIG. 3, a positive pressure manifold 300 includes a tracheal line 304, a pressure reservoir 302, a pressure release valve 301, a compressor 303 (e.g., a pressured gas source), an inflatable breathing bag 306, and a manifold pressure sensor 308. The tracheal line 304 is connected to the airway of the lung (not shown). The compressor 303 provides positive pressure to the pressure reservoir 303, and the pressure level in the pressure reservoir 302 can be modified by the pressure release valve 301, (e.g., pressure can be reduced). In certain embodiments, positive pressure manifold 300 is a computerized system that actively regulates pressure in the pressure reservoir 302 in response to the inspiratory and expiratory related pressure variations in the airway (e.g., as recorded by the tracheal pressure sensor 408 or by the manifold pressure sensor 308). The inflatable breathing bag 306 is attached to the pressure reservoir 302 to accommodate sudden volume changes during inspiration and expiration while keeping the pressure in the chamber, trachea, and lung constant. The volume of the inflatable breathing bag 306 may vary depending on the size of the lung being cultured. For example, the volume of the inflatable bag 306 may be between 250 cc and 4000 cc, at least 250 cc, less than 4000 cc, between 300 cc and 3500 cc, between 400 cc and 3000 cc, between 500 cc and 2500 cc, between 600 cc and 2000 cc, between 700 cc and 1500 cc, and between 800 cc and 1000 cc. The material of the inflatable breathing bag 306 any flexible, air impermeable and sterilizable material (e.g., latex or rubber). The manifold pressure sensor 308 facilitates both monitoring end-expiratory pressure and enabling flow calculations in the ventilation line.

Figure 3A:
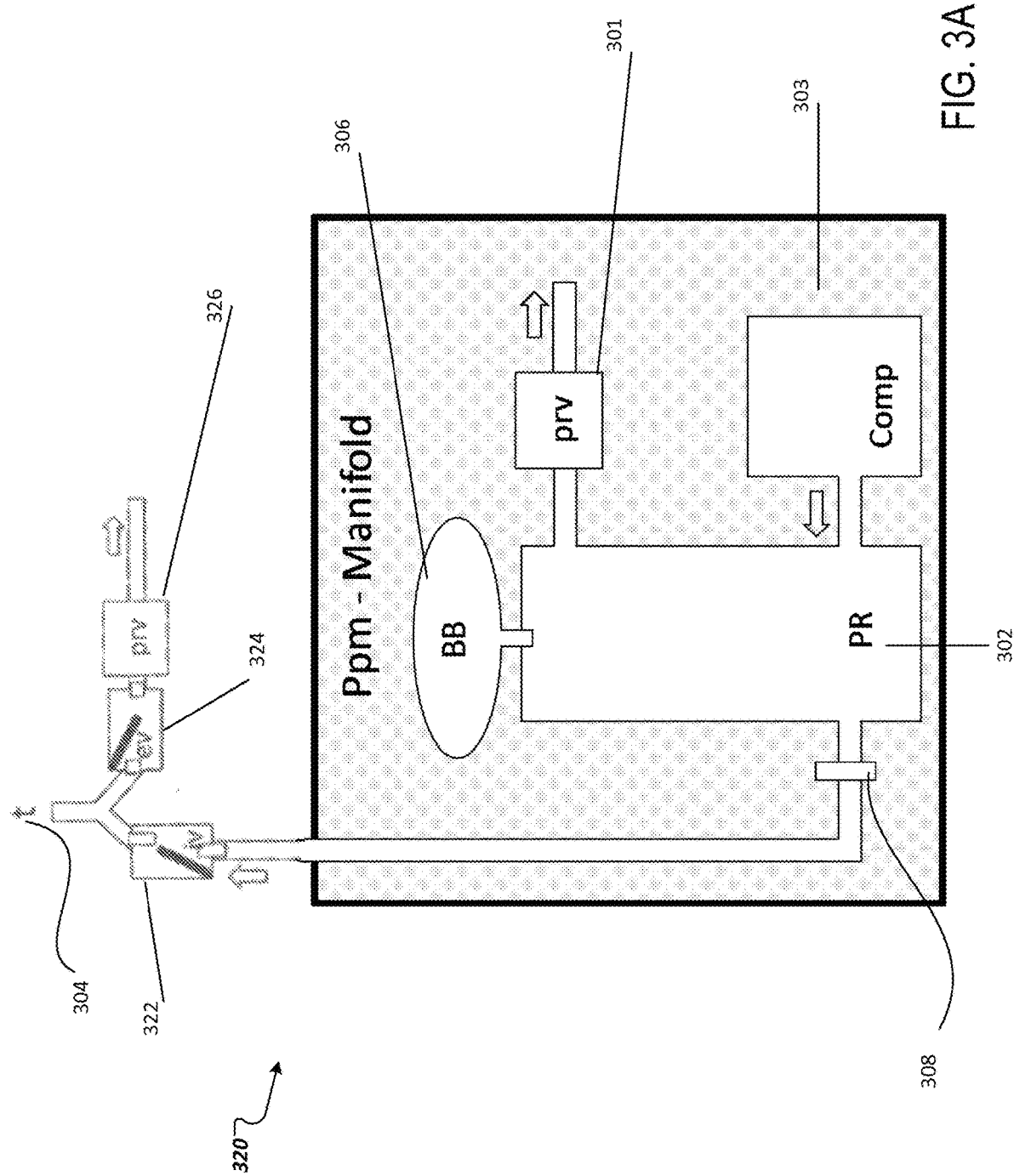

Referring to FIG. 3a, a positive pressure manifold 320 includes, as described above, the tracheal line 304, the pressure reservoir 302, the pressure release valve 301, the compressor 303 (e.g., a pressured gas source), the inflatable breathing bag 306, and the manifold pressure sensor 308. The positive pressure manifold 320 also includes an inspiratory valve 330, and expiratory valve 332 and an expiratory pressure release valve 334. The tracheal line 304 is connected to the airway of the lung (not shown). As described with reference to FIG. 3, the compressor 326 provides positive pressure to the pressure reservoir 302, and the pressure level in the pressure reservoir 302 can be modified by the pressure release valve 324, (e.g., pressure can be reduced). The tracheal line 304 is also connected to the inspiratory valve 322 and the expiratory valve 324. The inspiratory valve 322 and the expiratory valve are one-way valves that allow fluid, e.g., air, to flow in one direction and that prevent backflow. During the expiratory phase, air flows from the tracheal line through the expiratory valve 332 and the expiratory pressure valve 324 to an exhaust line (not shown). Expired fluid does not enter the pressure reservoir 301 due to the inspiratory valve 322. During the inspiratory phase, air flows from the pressure reservoir through the inspiratory valve 322 to the airway of the lung via the tracheal line 304. The expiratory pressure release valve 324 ensures that the expiratory line retains a positive pressure during an inhalation phase, thus preventing air from flowing through the expiratory line during an inhalation phase.

Figure 4:
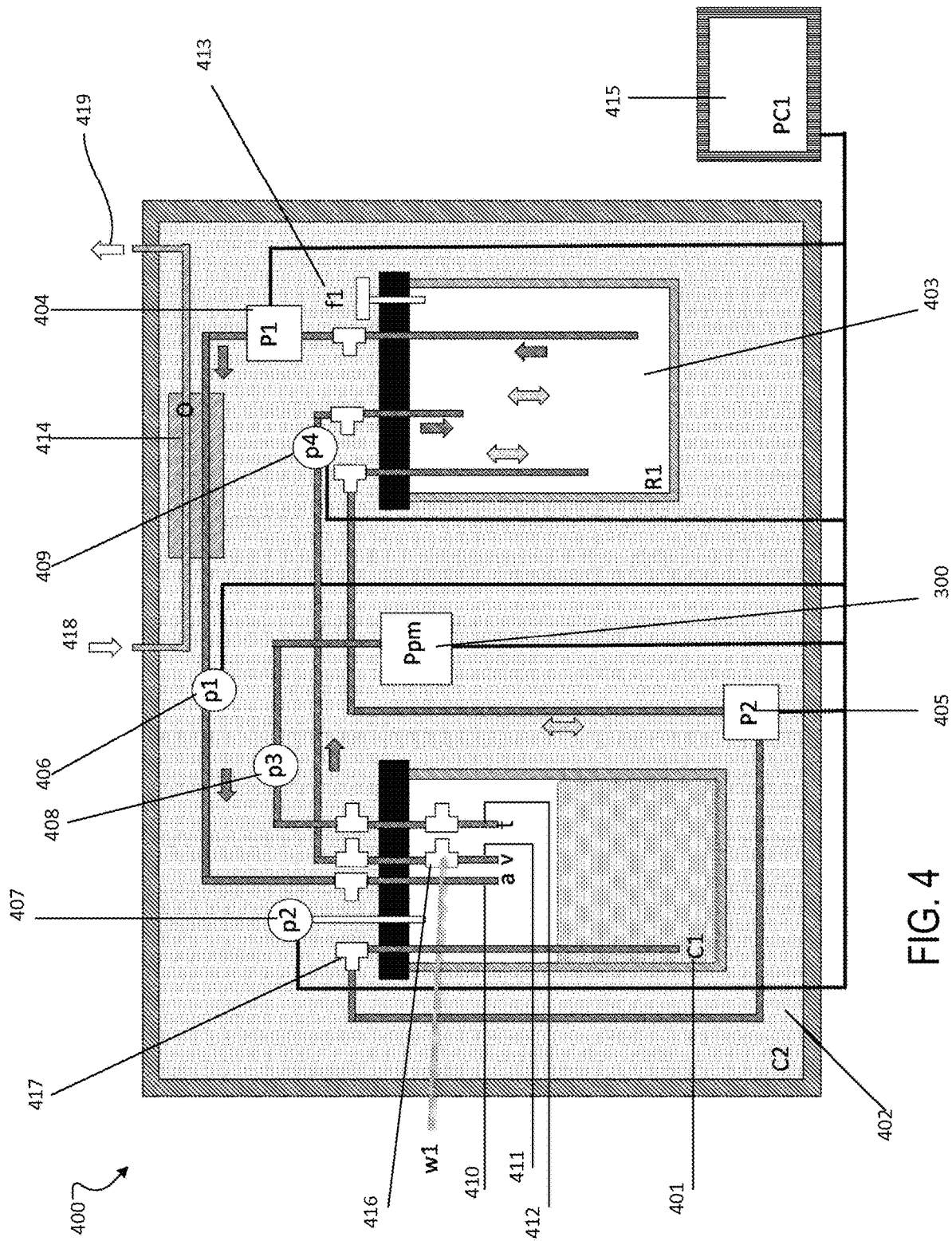
FIG. 4 is a schematic diagram of an exemplary lung bioreactor including a negative pressure dry ventilation system with a separate media reservoir and monitored venous drainage.

Referring to FIG. 4, components of bioreactor 400 include a lung chamber 401, an incubator chamber 402, a media reservoir 403, an arterial perfusion pump 404, a drainage pump 405, an arterial pressure sensor 406, a chamber pressure sensor 407, a tracheal pressure sensor 408, a venous pressure sensor 409, an arterial line 410, a venous line 411, a tracheal line 412, a sterile filter 413, an oxygenator 414, a control module 415, a venous valve 416, and the positive pressure manifold 300. The bioreactor 400 includes a negative pressure dry, e.g., using air, ventilation in addition to a perfusion system, and is generally arranged as described above with reference to the bioreactor 200 with the exception of the positive pressure module. The pressure in lung chamber 401 is variable to inflate or deflate the lung matrix.

During the inspiration phase, the pressure within the lung chamber 401 drops below the airway pressure, thereby creating negative airway pressure. This negative pressure causes fluid shifts from the vasculature into the tissue, leading to interstitial edema, and increased secretions in the airway. These fluid shifts are exacerbated by the resistance of the tracheal line 412 and attached tubing. During expiration phase, the pressure within the lung chamber 401 increases, thereby creating positive airway pressure. If the trachea is open to atmospheric pressure, or connected to a neutral pressure, proximal airways will be compressed by the chamber pressure and collapse leading to air trapping in distal airways and alveoli and damage to the lung matrix. The positive pressure manifold 300, as discussed above, minimizes pressure fluctuation during inspiration and expiration by having an appropriate size, e.g., approximately 10×the tidal volume of the lung. The control module 415 activates the compressor 303 or the pressure release valve 301, as discussed above, to maintain a constant pressure in the pressure reservoir 203, which is transmitted to the trachea through the trachea line 412 during the inspiration and expiration phases. Similar to bioreactor 200, media is refreshed between the lung chamber 401 and the media reservoir 403 by the perfusion pump 405. The combination of the arterial pressure sensor 406 and the bi-directional arterial perfusion pump 405 serves to maintain appropriate pressure and/or media fluid level in the lung chamber 401 (as discussed above).

Figure 5:
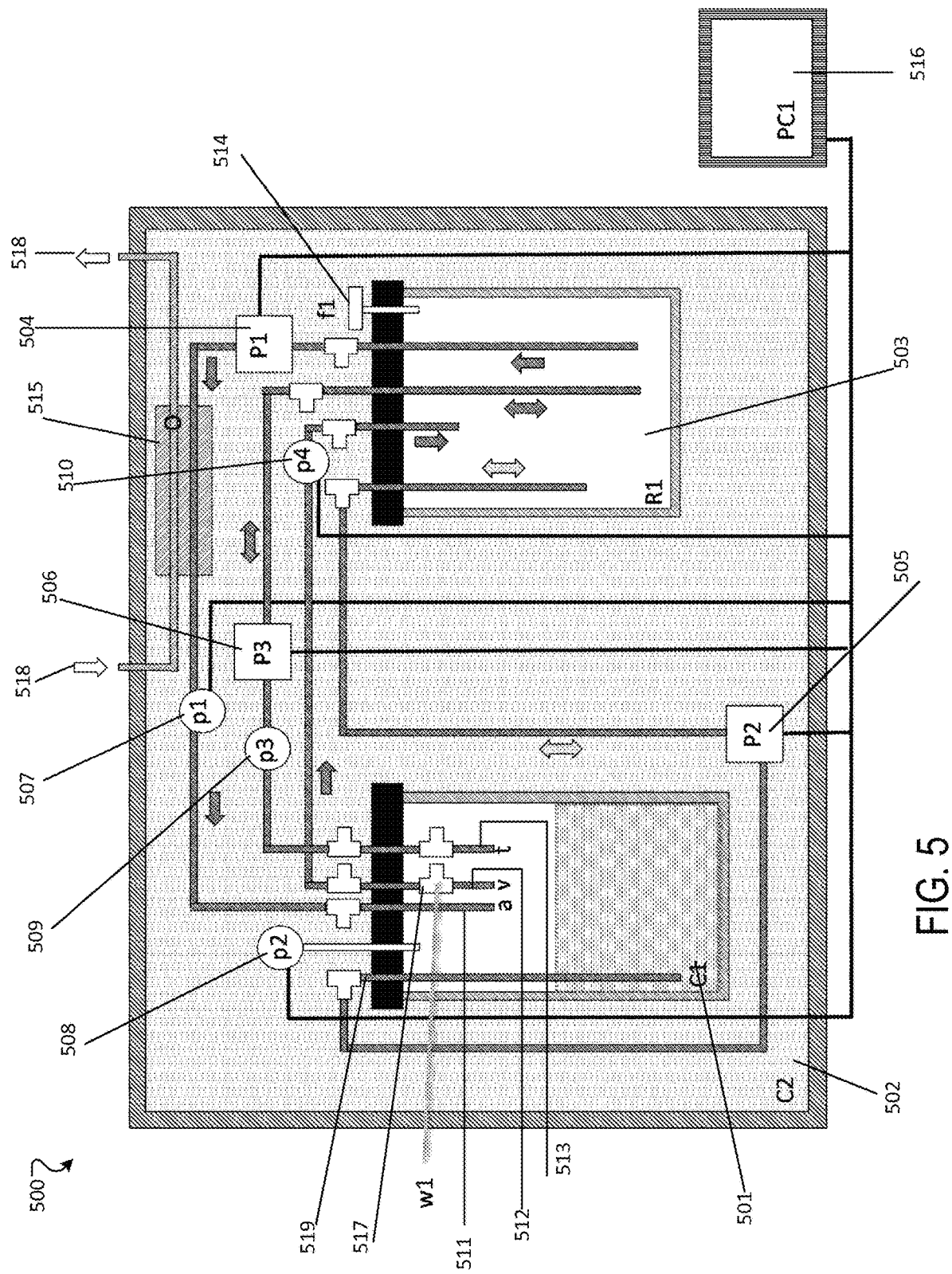
FIG. 5 is a schematic diagram of an exemplary lung bioreactor including a positive pressure wet ventilation system and perfusion system.

Referring to FIG. 5, components of a bioreactor 500 include a lung chamber 501, an incubator chamber 502, a media reservoir 503, an arterial perfusion pump 504, a drainage pump 505, a wet ventilation pump 506, an arterial pressure sensor 507, a chamber pressure sensor 508, a tracheal pressure sensor 509, a venous pressure sensor 510, an arterial line 511, a venous line 512, a tracheal line 513, a sterile filter 514, an oxygenator 515, a control module 516, and a venous valve 517. Lung chamber 501 holds a lung matrix (not shown). Similar to the bioreactors 100, 200, and 400, the pulmonary artery of lung is connected to the arterial line 511, the pulmonary vein of the lung is connected to venous line 512, and the trachea of the lung is connected to the tracheal line 513. In addition to the features of the bioreactor 200, the bioreactor 500 further includes the wet ventilation pump 506 connected to the tracheal line 513. The wet ventilation pump 506 enables positive pressure liquid ventilation. Wet ventilation pump 506 draws fresh media from the media reservoir 503 and pumps the media through the tracheal line 513 thereby inflating the lung with liquid (e.g., media). The wet ventilation pump 506 is bi-directional and aspirates liquid from the tracheal line thereby deflating the lung. Because the wet ventilation pump draws directly from the media reservoir 503, the lung matrix is continuously inflated with fresh media. The control module 516 controls the operation (e.g., duration, direction, and speed) of the wet ventilation pump 506 based on the pressure readings transmitted by the tracheal pressure sensor 509. For example, a positive inspiratory pressure of 5 to 45 cm $H_2O$ is applied during inspiration, while an expiratory pressure of 5 to −15 cm $H_2O$ is applied during expiration.

During wet ventilation and dry ventilation modes, ventilation can be pressure controlled (PC) or volume controlled (VC). In a pressure-controlled mode, the pump provides a defined inspiratory pressure and a defined expiratory pressure for a defined period (inspiratory time, expiratory time) with the possibility of positive, neutral, and negative pressure plateaus, at a defined rate. In a volume controlled ventilation mode, the pump generates a defined inspiratory pressure until a certain volume has been inspired, then holds a defined plateau, then generates an expiratory pressure until a certain defined volume is exhaled, or until a certain defined target pressure has been reached, then the pump may hold at a neutral pressure or a defined exhaled plateau pressure. Volume movements may be measured by a variety of flow meters (e.g., heat based, differential pressure-based or ultrasonic). These flow meters have to be attached to the tracheal line near the lung chamber to provide most accurate flow measurements.

As described with respect to the bioreactor 200, any fluid shift from the lung tissue to graph chamber 501 is drained automatically back to the media reservoir 503 using the bi-directional drainage pump 505. The control module 516 activates drainage pump 505 based on data gathered from the chamber pressure sensor 508.

Figure 6:
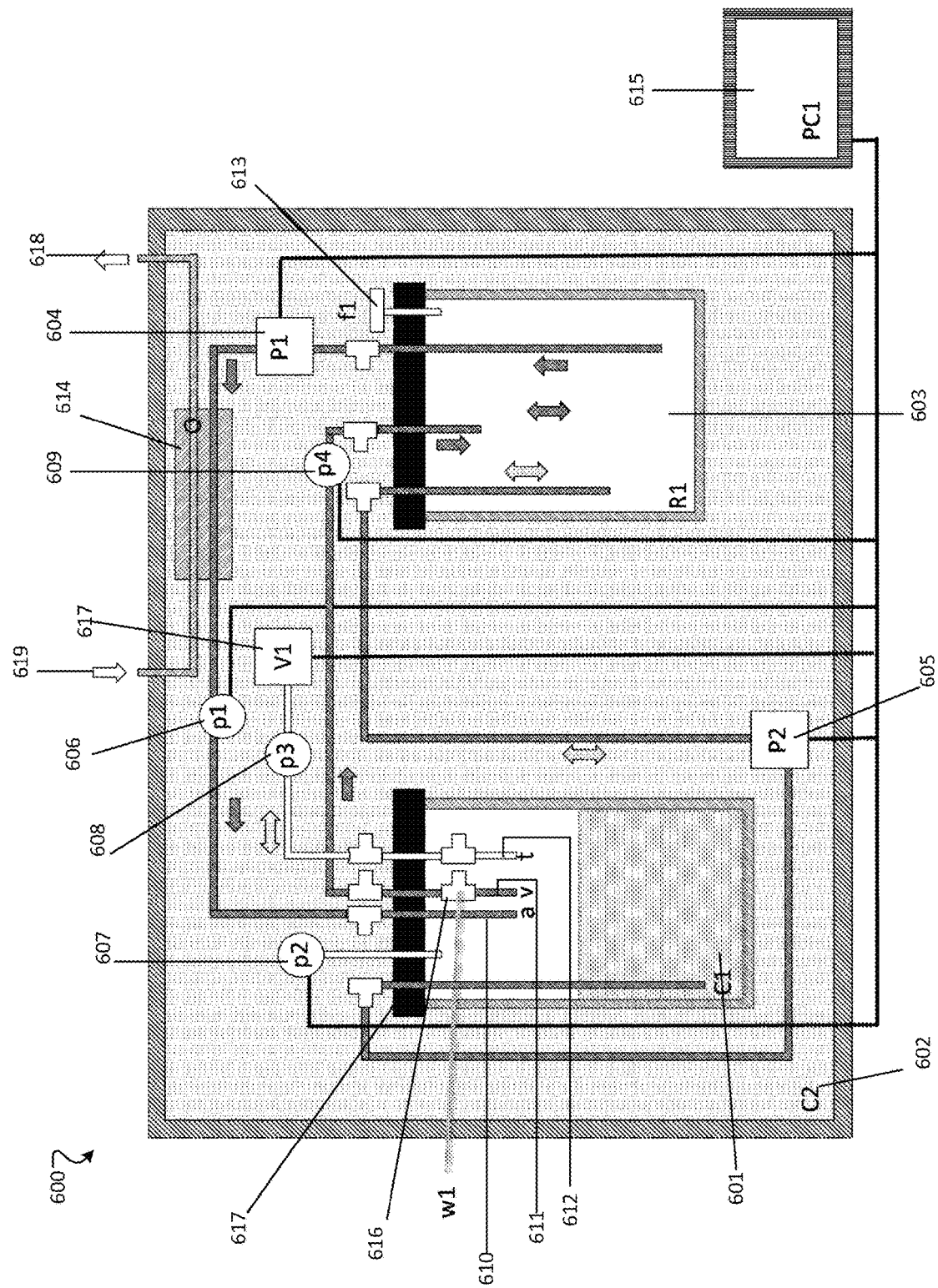
FIG. 6 is a schematic diagram of an exemplary lung bioreactor including a positive pressure dry ventilation system and perfusion system.

Referring FIG. 6, components of a bioreactor 600 include a lung chamber 601, an incubator chamber 602, a media reservoir 603, an arterial perfusion pump 604, a drainage pump 605, an arterial pressure sensor 606, a chamber pressure sensor 607, a tracheal pressure sensor 608, a venous pressure sensor 609, an arterial line 610, a venous line 611, a tracheal line 612, a sterile filter 613, an oxygenator 614, a control module 615, a valve controlling venous drainage 616, and a ventilator 617. In the bioreactor, the lung matrix is perfused with media through the arterial line, as discussed above with respect to the bioreactors 100, 200, 400 and 500.

Still referring to FIG. 6, bioreactor 600 includes the ventilator 617, which enables positive pressure dry ventilation. The ventilator 617 is bi-directional and pumps gas (e.g., air) through the tracheal line 612 into and out of the lung matrix. This gas movement causes the lung matrix to inflate and deflate in a manner similar to typical lung function. The bioreactor 600 may be used be used during late stages of organ culture and for functional testing of regenerated lung grafts and lungs. For example, the tracheal line can include at least one port for testing the ventilation dynamic between the tracheal pressure sensor 608 and the ventilator 617. The tracheal line may also include one or more ports that permit user access to the system for a bronchoscopic assessment of the lung grafts without contamination of the system. Each ingress or egress line may also contain at least one port to facilitate blood gas analysis to facilitate a real-time oxygen measurement.

Figure 7:
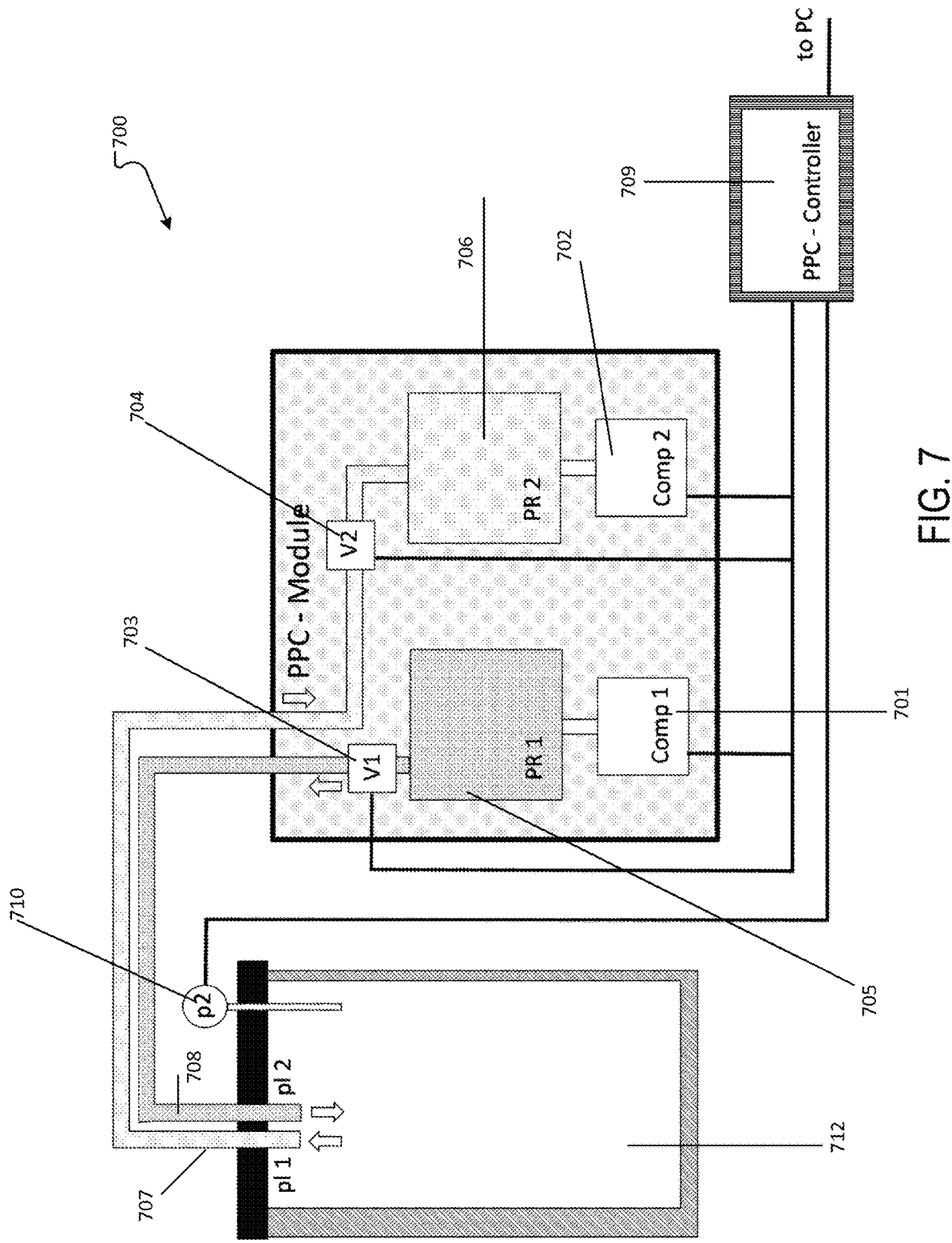
FIG. 7 is a schematic diagram of a pneumatic pressure control module connected to an organ culture chamber.

Referring to FIG. 7, pneumatic pressure control module 700 includes an inlet pressure valve 703, an inlet pressure reservoir 705, an inlet compressor 701, an inlet line 707, an outlet pressure valve 704, an outlet pressure reservoir 706, an outlet compressor 702, an outlet line, and a PPC controller 709. The inlet line 707 and the outlet line 708 are connected to the lung chamber 712 (as described above), which includes a chamber pressure sensor 710. The inlet and outlet compressors 701, 702 charge the inlet and outlet pressure reservoirs 705, 706 with gas (e.g., air). The inlet and outlet pressure valves 703, 704 (e.g., solenoid valves) and inlet and outlet compressors 701, 702 are controlled by the PPC controller 709. During the inspiration phase, outlet valve 704 opens and generates negative pressure into the graft camber 712. Once the negative target pressure is recorded by the chamber pressure sensor 710 (e.g., −20 cm$H_2O$), the outlet valve 704 closes. Chamber pressures may range from −50 to +100 cm$H_2O$ during inspiration and expiration. Once lung compliance approaches that of normal lung, chamber pressure more closely mimics the physiologic range of intrapleural pressure (e.g., −10 to +25 cm$H_2O$). After an appropriate plateau phase, an expiration phase begins in which the inlet pressure valve 703 opens and allows generation of positive pressure inside the lung chamber 712. Once the positive target pressure is recorded by the chamber pressure sensor 710 (e.g., 25 cm$H_2O$), the inlet valve 703 closes. The inlet and outlet pressure reservoirs 705, 706 are sized appropriately to enable quick adjustment of the pressure in the lung chamber 712. The inlet and outlet pressure reservoirs prevent and/or reduce vibration artifacts generated by the inlet or outlet compressors 701, 702. In some embodiments, the slope of the pressure equilibration can be adjusted by an additional resistances valve (not shown) placed in the inlet line 707 and/or outlet line 708. As discussed above, ventilation can be pressure controlled (PC) or volume controlled (VC).

Figure 8:
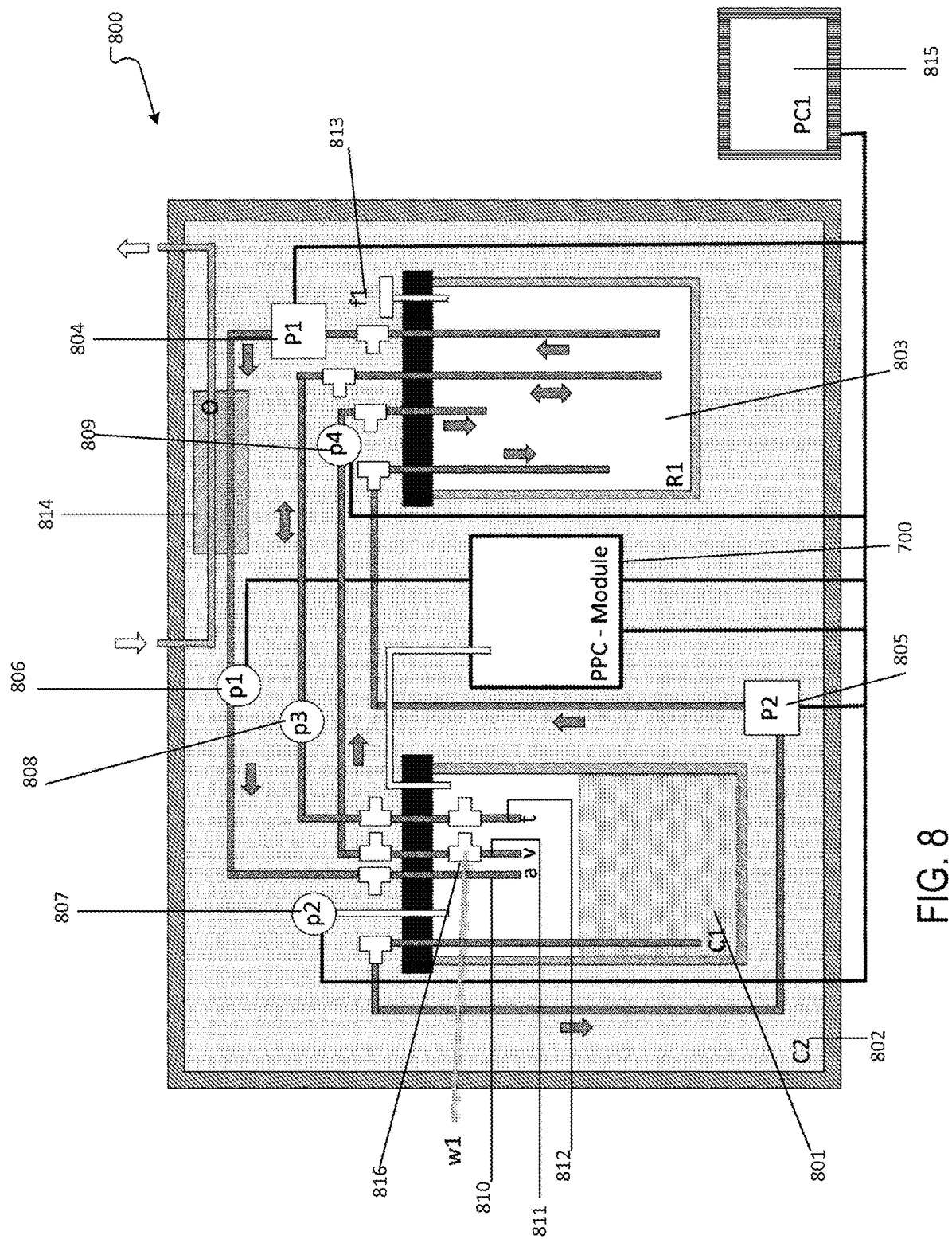
FIG. 8 is a schematic diagram of an exemplary lung bioreactor including a negative pressure wet ventilation system with a perfusion system and with a pneumatic pressure control module as shown in FIG. 7.

Referring to FIG. 8, components of the bioreactor 800 include a lung chamber 801, an incubator chamber 802, a media reservoir 803, an arterial perfusion pump 804, a drainage pump 805, an arterial pressure sensor 806, a chamber pressure sensor 807, a tracheal pressure sensor 808, a venous pressure sensor 809, an arterial line 810, a venous line 811, a tracheal line 812, a filter 813, an oxygenator 814, a control module 815, a venous valve 816, and the PPC module 700.

The bioreactor 800 is generally arranged as described with respect to the bioreactor 200 with the addition of the PPC module 700. The pressure in the lung chamber 801 is regulated by the PPC module 700 (as described above). This arrangement permits negative pressure ventilation without large fluid shifts into and out of the lung chamber 801. The drainage pump maintains a constant fluid level in the chamber 801 while the negative pressure during inspiration and the positive pressure during expiration are accomplished by the PPC module 700. By replacing the source of negative and positive ventilation with the PPC module 700, foaming of media, graph damage due to turbulence and equipment breakdown throughout the culture is prevented and/or reduced. Furthermore, the bioreactor 800 is readily adaptable to a variety of lung matrix sizes (e.g., human adult lungs, human children's lungs, or any animal (e.g., mammal lungs) because the PPC module 700 is able to achieve a variety of physiologic respiratory rates. As described above, during wet ventilation a positive airway pressure is maintained by increasing the height of the media reservoir 803 with respect to the height lung chamber 801 thus causing hydrostatic pressure through the tracheal line.

Figure 9:
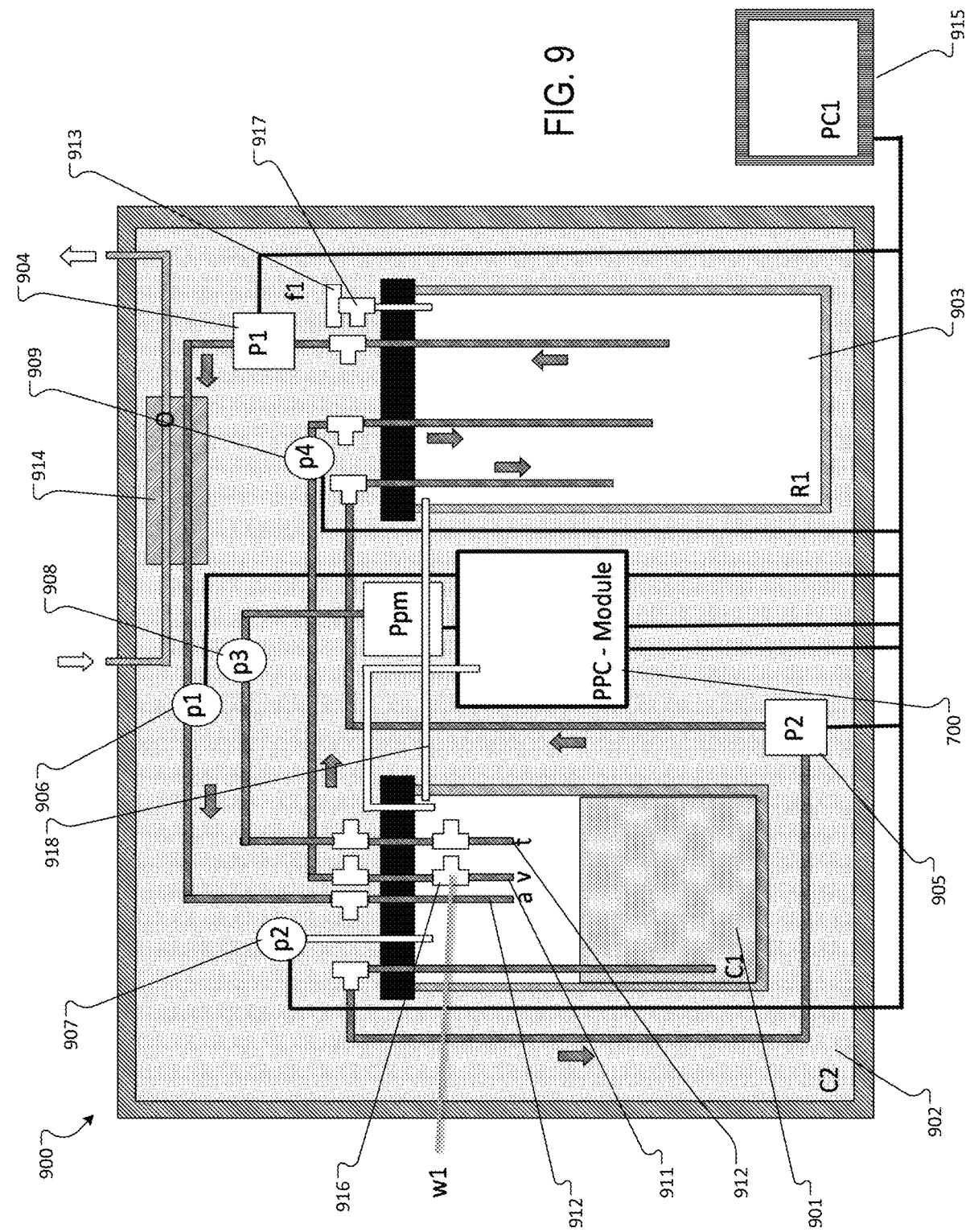
FIG. 9 is a schematic diagram of an exemplary lung bioreactor including a negative pressure dry ventilation system with a positive pressure module shown in FIG. 3 and a pneumatic pressure control module shown in FIG. 7.

Referring to FIG. 9, components of the bioreactor 900 include a lung chamber 901, an incubator chamber 902, a media reservoir 903, an arterial perfusion pump 904, a drainage pump 905, an arterial pressure sensor 906, a chamber pressure sensor 907, a tracheal pressure sensor 908, a venous pressure sensor 909, an arterial line 910, a venous line 911, a tracheal line 912, a filter 913, an oxygenator 914, a control module 915, a venous valve 916, an equilibration line 918, a filter occluder 917, the PPC module 700, and the positive pressure manifold 300. The components of the bioreactor 900 are generally arranged as described with respect to bioreactor 800, with the exception of the addition of the positive pressure manifold 300 connected to the tracheal line 911. This arrangement enables the bioreactor 900 to generate negative pressure ventilation, as described with respect to the bioreactor 800 and generate and maintain positive airway pressure (through the tracheal line 911) throughout inspiration and expiration. Bioreactor 900 is further configured to adapt to a large matrix size (e.g., human adult lungs and human children's lungs) and for long-term culture due to the addition of the equilibration line 918 and the occluder 917.

In the human body under normal conditions (e.g., room air, spontaneous ventilation) normal measurements are: net pressure from trachea/airway "$p_t$"≈0 cmH$_2$O; interpleural space pressure "$p_p$"≈−5-8 cmH$_2$O; arterial pressure "$p_a$"≈13 mmHg; venous pressure "IN," 6 mmHg (mean $p_v$ 9.5 mmHg); and interstitial pressure $p_i$≈−5 mmHg. Using the Starling equation (See Granger H J, Laine G A et al. Dynamics and control of transmicrovascular fluid exchange. In: Staub N C, Taylor A E, editors. Edema. New York: Raven Press; 1984. p. 189-228), calculations can demonstrate that a lung experiences negative interstitial and lymphatic pressures, which may facilitate lymphatic drainage. For example, using the following equation:

$$J_V = LS[(Pmv - Ppmv) - \sigma(\Pi mv - \Pi is)],$$

where LS≈0.2 mL/min/100 g/mm Hg (Kf or fluid filtration coefficient, a measure of permeability to fluid and vascular surface area); Pmv≈5 to 10 mm Hg (microvascular (capillary) hydrostatic pressure); Ppmv≈−5 to −7 mm Hg (perimicrovascular or interstitial hydro-static pressure); σ≈0.5 to 0.8 (the osmotic reflection coefficient, determining the relative contribution of the oncotic pressure gradient across the vasculature to the net driving pressure, a measure of the permeability of a specified membrane (eg, endothelial) to a particular solute (e.g., albumin), varying between 0 when the membrane is totally permeable, to 1 when it is totally impermeable); Πmv≈24 mm Hg (the oncotic pressure of the blood in the microvasculature of the lung); and Πpmv≈14 mm Hg (the oncotic pressure in the perimicrovascular interstitium), the resulting outward pressure is ≈1.5-2 mmHg and a net fluid flow of approximately 10-20 cc/min into the interstitial space. The net pressure from trachea/airway ($p_t$) and interpleural space ($p_p$) is −5 mmHg, resulting in negative interstitial and lymphatic pressures facilitating lymphatic drainage.

The net negative pressure across pulmonary parenchyma and its fluctuations during respiration as well as the stretch of pulmonary tissue combine to function as a pump that drains interstitial fluid, as discussed in, for example, Bhattacharya J et al. Lung expansion and the perialveolar interstitial pressure gradient. *J Appl Physiol* 1989; 66: 2600-5. Correspondingly, increased spontaneous ventilation leads to increased lymphatic flow as discussed in, for example, Albelda S M et al., Effects of increased ventilation on lung lymph flow in unanesthetized sheep. *J Appl Physiol* (1985). 1986 June; 60(6):2063-70.

In a standard ex vivo lung perfusion (EVLP) setup used for lung evaluation, values are set to $p_t$≈7.5 cmH2O, $p_p$ is 0 mmHg, $p_a$≈13 mmHg, $p_v$≈6 mmHg (mean $p_v$ 9.5 mmHg). Applying the equation, as discussed above, under ideal circumstances (assuming physiologic oncotic pressure of perfusate and osmotic reflection coefficient) a net fluid flow into the interstitial space is approximately 10-20 cc per minute. In this setting, the lung is isolated and thus lacks the physiologic counter-pressure normally applied by the chest wall, the fluctuations of interpleural pressure and interstitial pressure, and the resulting bidirectional transpulmonary gradient. Over time, this leads to the formation of hydrostatic interstitial pulmonary edema and ultimately alveolar edema with organ failure. This has been described as circuit induced lung injury in, for example, Erasmus M E et al., Normothermic ex vivo lung perfusion of non-heart-beating donor lungs in pigs: from pretransplant function analysis towards a 6-h machine preservation. *Transpl Int* 2006; 19: 589-593.

Referring to FIG. 9, the pressure equilibration line 918 between the lung chamber 901 and the media reservoir 903 and the occluder 917 on the filter 913 equalize pressures between the lung chamber 901 and the media reservoir 903. This ensures equal pressure across both chambers during all phases of the respiratory cycle. This modification can be applied to all bioreactors discussed herein, both small animal and large animal/human, and can be used in both positive and negative pressure ventilation modes and wet and dry ventilation modes. The introduction of this pressure equilibration, line 918 enables the creation of a bi-directional transpulmonary gradient. In other words, the lung can be compressed from the inside via the Ppm 300 (thereby creating positive airway pressure), and from the outside via the PPC Module 700 (thereby creating positive chamber pressure).

The purpose of this bidirectional transpulmonary gradient is to prevent the formation of interstitial edema over long-term isolated lung culture and to treat edema that has already formed (e.g., in previously injured lungs) by pushing the interstitial fluid into the vasculature thus improving lung function (e.g., compliance, diffusion, weight, and size). This gradient can be achieved if the venous pressure can be adjusted relative to the chamber pressure. By adjusting the height of the media reservoir 903, and thereby adjusting the height of the water column in the venous cannula and draining pulmonary venous return to media chamber 903, venous pressure 904 can be kept at a constant level higher or lower than the chamber pressure. Essentially, the equilibration between the two chambers allows constant pulmonary venous drainage during negative pressure ventilation. In contrast, if equilibration is not maintained and P, is kept constant, a negative pressure in a lung chamber 901 would result in decreased venous drainage or reversal (e.g., partial or complete) in venous flow, while a positive pressure in a lung chamber 901 would collapse pulmonary veins leading to outflow obstruction.

The invention will be further described in the following examples, which do not limit the scope of the invention described in the claims.

EXAMPLES

Example 1—Lung Regeneration Based on Acellular Lung Scaffolds and Human Derived Lung Progenitor Cells Background Lung grafts have been generated using fetal epithelial cells as discussed, for example, Ott H C et al., Regeneration and orthotopic transplantation of a bioartificial lung. *Nat Med.* 2010 August; 16(8):927-33 and Song J J et al., Enhanced in vivo function of bioartificial lungs in rats. *Ann Thorac Surg.* 2011 September; 92(3):998-1005. In order to translate this technology into clinical application, patient-derived cells should be used. These cells can be derived from IPS cells that are pre-differentiated toward such by phenotypes.

Methods:

Rat lungs were harvested en block with heart and trachea from adult Lewis rats. The donor organs were decellularized by 0.1% sodium dodecyl sulfate ("SDS") perfusion and subsequent saline washes via the pulmonary artery. The resulting lung scaffolds were then mounted in a bioreactor as described above in FIG. 2 enabling negative pressure wet ventilation. 30 million human umbilical cord endothelial cells and 100 million pre-differentiated human iPS cells (BJRiPS cells derived via reprogramming of dermal fibroblast cells) at the definitive endoderm stage were delivered via pulmonary artery and trachea respectively at the same time. Lung grafts were then mounted in a bioreactor and maintained under static organ culture for two hours to enable cell engraftment. Media perfusion was then initiated at a rate of 3 mL per minute. Wet ventilation was initiated with a pressure range from −20 to positive 10 centimeters $H_2O$ in the graft chamber and a continuous positive wet airway pressure of 8 cm $H_2O$. Culture under these conditions was maintained for a total of 10 days. Before termination of the experiment, lungs were ventilated using positive pressure ventilation with peak inspiratory pressure of 35 cm $H_2O$, a positive inspiratory pressure of 5 cm $H_2O$, and a $FiO_2$ of 100% and 21%. Blood gas samples were drawn from the venous line. Lung grafts were then harvested from the bioreactor. The right lung was used for histologic biochemical and genetic tissue analysis. The left lung was used as a lung graft and orthotopically transplanted in a rat model.

Results:

Cell engraftment of endothelial and pre-differentiated IPS cells was observed. Cell viability was confirmed by TUNEL staining and found to be greater than 75% at the end of the culture. Gas exchange was confirmed at the end of the experiment by blood gas analysis. Successful surgical transplantation of the left lung was accomplished in all of the regenerated grafts.

Example 2—Lung Preservation Through Perfusion and Negative Pressure Ventilation: Rat Lung Model Background Donor lungs are currently transported in a cold ischemic state. Efforts have been made to preserve lungs ex vivo during normal thermic perfusion and ventilation. Current state-of-the-art equipment does not allow the maintenance of donor organs with good viability beyond 6 to 48 hours. Tissue edema and mechanical damage lead to tissue damage and graft failure during this period. All currently available systems use positive pressure dry ventilation, which leads to mechanical damage of the lung graft in the absence of a protective chest wall. We designed a negative pressure wet and dry ventilation bioreactor and examined the capability to maintain viable lung tissue over a prolonged period (>7 days).

Methods:

Lungs were harvested en bloc with heart and trachea from 3 months old SD400 rats after anesthesia with isoflurane and systemic injection of 3000 units of heparin followed by flush via pulmonary artery with 10 ml of PBS cooled down to 4 degrees Celsius. Trachea, pulmonary artery (PA) and left atrium (LA) were flushed in a sterile fashion. The lungs were placed in 500 ml organ chamber (the main chamber) and cultured in an incubator at 37 degrees Celsius. A bioreactor as described in FIG. 4 was used for this experiment.

Tracheal line was connected to the positive pressure manifold system, which provided continuous positive airway pressure (CPAP) with 5% $CO_2$ balanced with Oxygen or ambient air. PA line was connected to a perfusion line, which was also connected to the reservoir filled with perfusate. Perfusate was composed of 500 ml RPMI, 1640 Glutamax, 500 mg albumin, 50 ml Fetal Bovine Serum, 5 ml antibiotic/antimycotic solution (10,000 units penicillin, 10 mg streptomycin, 25 ug amphotericin B per mL). The main chamber and the reservoir were connected with a retuning tube, too so that perfusate could be circulated between the two chambers. Perfusate was changed at least every other day. Both perfusion and returning flows were regulated by a peristaltic pump (Ismatec, Cole-Parmer). The perfusion line pressure was monitored close to the PA line. The main chamber and the reservoir were connected by a ventilation tube with a peristaltic pump (P-230, Harvard Apparatus) which could create positive and negative pressure in the main chamber by moving in and out air and fluid for negative pressure lung ventilation.

After 6 or 7 days of lung culture by PEEP/CPAP, and perfusion with or without negative pressure lung ventilation, lungs were fixed, paraffin-embedded, and sectioned. H&E staining and TUNEL staining were performed.

Result:

Stable isolated lung culture was maintained with the setting as follows; 15 cm $H_2O$ PEEP with 5% $CO_2$ and balanced Air, perfusion rate 1-3 ml/min, negative pressure ventilation at the main chamber pressure from +10 mm Hg down to −20 mm Hg, respiratory rate 2 to 4 depending on how fast the target negative pressure was achieved. The measured perfusion line pressure was from 8.4 up to 30 mm Hg.

Regarding histology, several areas of normal-appearing lung tissue were seen after seven days of culture. Tunnel staining confirmed preserved cell viability.

Example 3—Recellularization and Culture of Human Lung Scaffolds

The left lung from a pediatric donor, aged 4 years, was removed and the right lung successfully cannulated and fully decellularized. Following decellularization, the upper and lower right lobe were separated and utilized for recellularization and culture.

For cell seeding and culture, both the main artery and vein of the lobe were isolated and cannulated, with the vascular cannula designed to allow for passive drainage of perfusate. The main airway was intubated and connected through the lid of the bioreactor chamber. This also system allows for constant flow or pressure controlled perfusion of media.
Methods A total of 500×106 Pulmonary Alveolar Epithelial Cells (PAEpiCs, ScienCell) were delivered to the airway by slow syringe, followed by 2-hours of static incubation at 37° C. Perfusion with a volume of 1.5 L Pulmonary Alveolar Cell Growth Media was initiated at a rate of 60 ml/min, generating a pressure of −8-10 mmHg. Perfusion and culture were maintained for 4 days before the tissue was harvested for analysis. No contamination was observed during culture.
Result Histologic analysis of several areas across the lung tissue demonstrated heterogeneous cell retention but included several areas of robust recellularization. The patchy nature of the cell distribution is likely due to variations in the cell delivery. Recellularized areas of the lung showed a high level of cell attachment and elongation along the natural architecture of the lung scaffold. Further analysis of cell viability by TUNEL assay indicated a very low level of apoptosis occurred over the 4 days of culture.

Example 4—Cadaveric Porcine Lungs

This example describes a validation experiment in which a set of cadaveric porcine were connected to a bioreactor and the functions of the bioreactor were tested.
Methods A set of cadaveric porcine lungs was obtained for testing. The pulmonary artery and trachea were cannulated, the organ placed inside the organ chamber, and the cannula connected to their corresponding inputs (the perfusion line and ventilation line respectively). Perfusion with phosphate buffered saline with heparin was initiated prior to attempting to ventilate the organ. The constant flow and constant pressure modes of perfusion both were implemented.
Results Once successful perfusion was achieved, pressurization modes of the organ chamber were tested. Both pressurization modes were successful in ventilating the organ. However pressurization by pressure targets (+20 mmHg to −150 mmHg) resulted in a greater visible change in organ volume. Ventilation was carried out over an 18-hour period (overnight) to confirm consistency in bioreactor functions. The bioreactor parameters used for the first test on cadaveric lungs are summarized in Table 3.

This experiment did not include a ventilation bag connected to the PPM manifold. This resulted in larger negative gauge pressures needed in the organ chamber to ventilate the organ as the limited gas volume within the ventilation line and organ expanded. The addition of a sufficiently large ventilation bag should alleviate this expansion, allowing gas to flow freely into and out of the lungs in response to organ chamber pressure changes rather than expanding and contracting.

TABLE 3

Summary of bioreactor settings used for test on cadaveric porcine lungs

| Parameter | Value or Mode |
|---|---|
| Temperature (C.) | 25 (bench top) |
| Ventilation Type | Dry |
| PEEP | 20 mbar |
| Ventilation Gas | Carbogen |
| Pressurization Mode | Pressure Targets |
| Organ Chamber Pressure Targets | +20 mmHg and −150 mmHg |
| Pressure Reservoir Range: Vacuum | −250 mmHg to −500 mmHg |
| Pressure Reservoir Range: Compressor | 1900 mmHg to 2200 mmHg |
| Perfusion Mode | Constant Pressure |
| Perfusion Pressure Target | +70 mmHg relative to atm. |
| Perfusate Solution | 1× PBS + heparin |
| Perfusate Volume | 4 L |
| Total Ventilation Time | 18 h |

Example 5— Preservation of Porcine Lungs (Short Term 24 Hours)

Figure 10A:
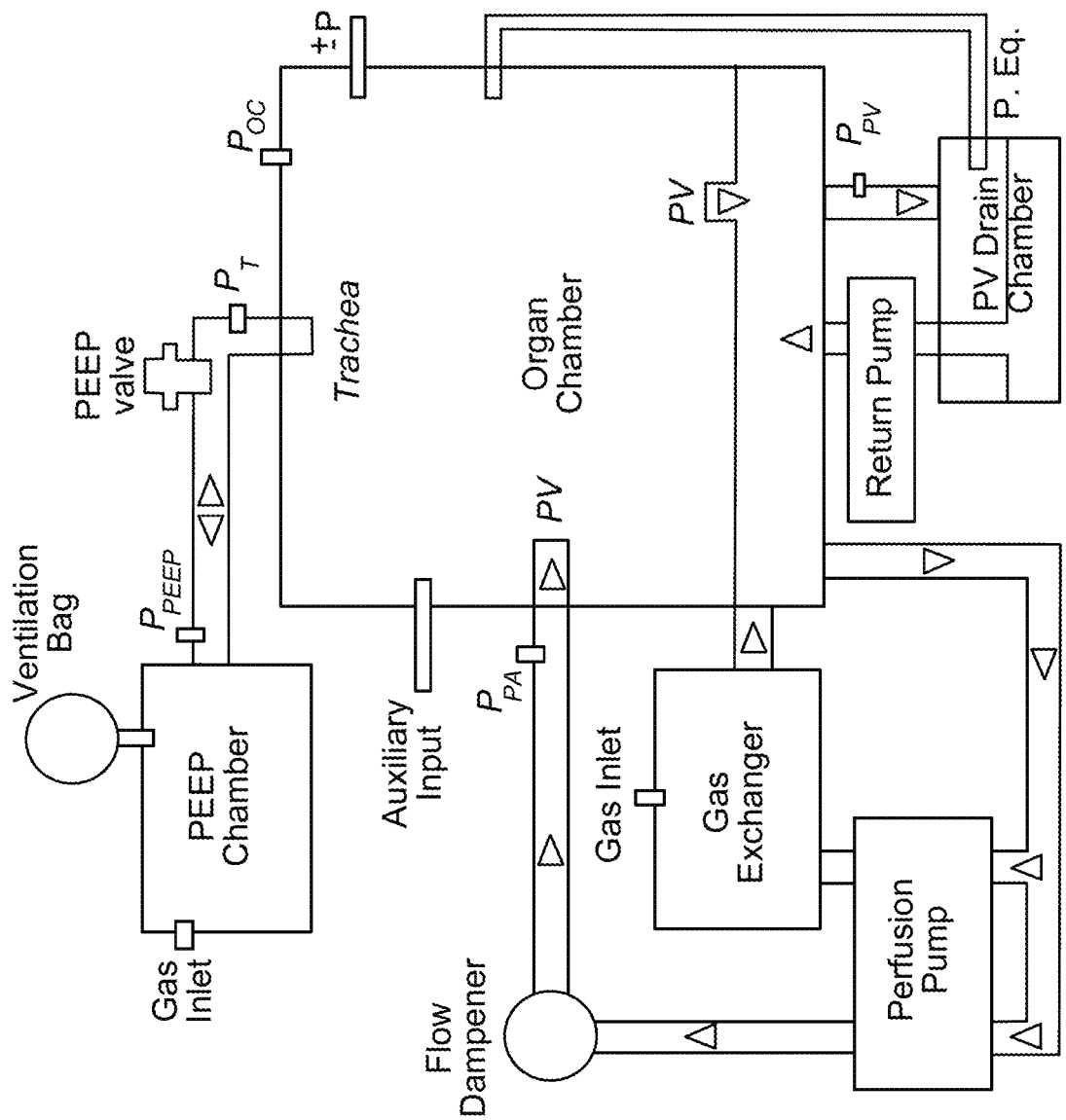
FIG. 10A is a schematic diagram of a clinical an exemplary lung bioreactor.
Figure 10D:
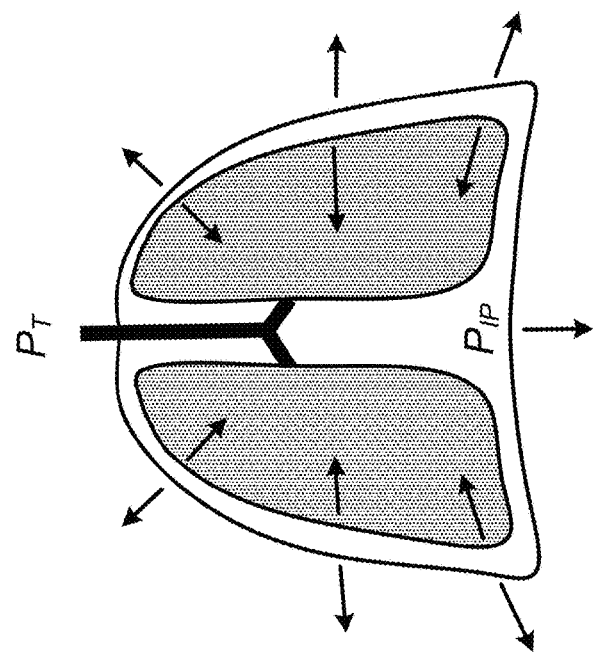
FIG. 10D is a schematic diagram of forces acting on a lung in vivo.
Figure 10B:
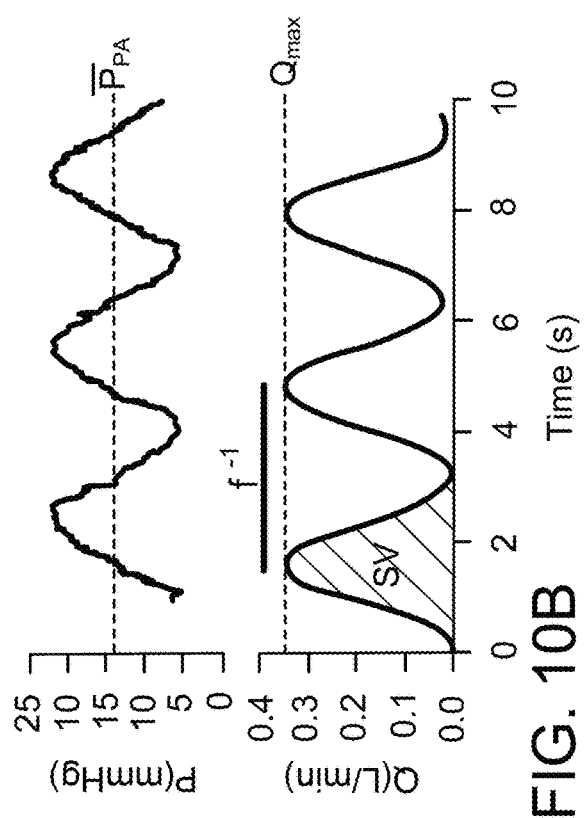
FIG. 10B-C are graphs of physiological data associated with lung culture including example ventilation volume (top) and pressure (bottom) traces from isolated lung culture. The discontinuity in top plot represents volume exiting PEEP valve; VT represents tidal volume; RR represents respiratory rate; PT represents trachea pressure; POC represents organ chamber pressure; I represents inspiratory time; E represents expiratory time.
Figure 10C:
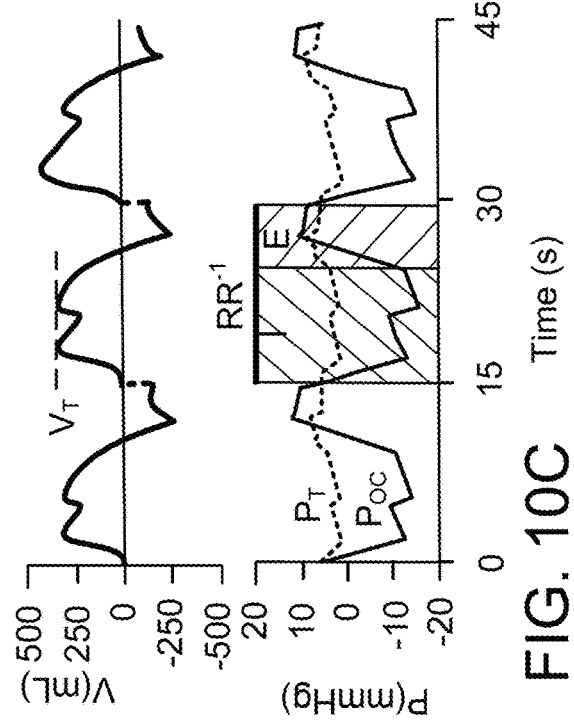

This example describes a validation experiment in which isolated porcine lungs were connected to a bioreactor to validate the bioreactor functions via short-term isolated lung culture. Organ chamber pressure (FIG. 10A, $P_{OC}$), PA pressure (PPA), PV pressure ($P_{PV}$), PEEP chamber pressure ($P_{PEEP}$) and trachea pressure ($P_T$) are monitored throughout culture. Control of perfusion parameters, ventilation parameters, and logging of bioreactor events are achieved via a National Instruments compact data acquisition (cDAQ) system in combination with a custom developed LabVIEW program (National Instruments, Woburn, MA).

Negative-pressure ventilation in the system is pressure-controlled and governed by four parameters: the respiratory rate (RR), the inhalation to exhalation (I:E) ratio, the lower organ chamber pressure target ($P_{OC\text{-}Lower}$), and the upper organ chamber pressure target (POC-Upper). The RR determines the length of each breath while the I:E ratio defines the time division of each breath into an inhalation or exhalation state. $P_{OC\text{-}Lower}$ and $P_{OC\text{-}Upper}$ represent the air pressures that the organ chamber is maintained at during inhalation and exhalation respectively. The difference between $P_{OC\text{-}Lower}$ and $P_{OC\text{-}Upper}$ determines the size of the breath or the range of pressures the exterior of the lung is exposed to. The location of these targets relative to the PEEP chamber pressure, therefore, influences $P_{Transmural}$ during ventilation. For these experiments, $P_{OC\text{-}Upper}$ was set close to the PEEP chamber pressure and $P_{OC\text{-}Lower}$ was set 10-15 mmHg below this, relying on the lung's elastic recoil for an adequate exhalation so as not to collapse recruited airways. These parameters were adjusted during culture to maintain inflation and reduce the buildup of any visible edema according to Table 4. Adjustments were made about as frequent as media sampling, between 3-7 times per 24-hour period.

TABLE 4

Table of Culture Parameter Adjustments

| Observation | Adjustment |
|---|---|
| PPA too high or too low | Decrease or increase PA flow rate |
| Perfusate not draining from PV cannula | Adjust PV cannula |
| Significant atelectasis | Increase I:E or breath size (distance between POC-Upper and POC-Lower) |
| Little visible motion during ventilation | Increase breath size or make breaths longer (reduce RR) |

TABLE 4-continued

Table of Culture Parameter Adjustments

| Observation | Adjustment |
| --- | --- |
| Lung deflates before POC-Upper is reached | Decrease POC-Upper or increase I:E |
| Over-inflation | Decrease breath size, decrease I:E, make breaths shorter (increase RR), or increase POC-Lower (bring closer to 0) |
| Under-inflation | Increase breath size, increase I:E, make breaths longer (decrease RR), or decrease POC-Lower |

Methods

Donor lungs were unpacked using sterile technique and placed in a laminar flow hood. Using custom connectors (e.g., various hose barb fittings, Cole-Parmer, Vernon Hills, IL), the trachea (T), pulmonary artery (PA), and left atrial cuff (PV) were cannulated. The lung was then placed into the organ chamber (Instron TERM, Norwood, MA) for culture and the PA, PV, and trachea cannulas were attached to their respective connections. The clinical-scale bioreactor (FIG. 10A) includes airtight organ chamber that houses the lung graft, acts as a fluid reservoir, and provides connections for physiologic perfusion and ventilation. The organ chamber and accessory chambers are placed inside an incubator at 37° C. to maintain the temperature for the duration of the isolated lung culture. An important feature of this setup is the ability to maintain sterile organ culture in a completely sealed system over prolonged periods of time (potentially weeks), enabling media exchange, sampling, and organ interventions.

Initial validation of bioreactor functions was carried out using slaughterhouse porcine lungs (n=8) with warm ischemia time>1 h and cold ischemia time>24 h. For each set of lungs tested, the PA, PV, and trachea were cannulated, a tissue biopsy was taken as control, and the organ was weighed before being connected within the organ chamber. Perfusion of culture media was then initiated (the perfusion line was primed with 2 L media prior to connecting the PA), the lungs were recruited, PEEP was established, and negative pressure ventilation was initiated with incubator air (21% O2, 5% CO2). Culture media contained DMEM supplemented with 1× GlutaMAX, 1×MEM Amino Acids (Cat. #s 12800-017, 35050-061, and 11130-051, Life Technologies, Carlsbad, CA), 1% v/v antibiotics/antimycotics, and 110 nM hydrocortisone (Cat. #s A5955 and H6909 Sigma-Aldrich, St. Louis, MO), either with 10% w/v BSA (Cat. #A2153, Sigma) as colloid or without colloid. Culture was maintained for 24 hours during which perfusate was periodically sampled at the PA and PV. Culture media was exchanged twice per 24 hour period by removing 1-2 L of PV effluent from the PV drain chamber replenishing with an equal or greater volume of fresh media to the organ chamber. Perfusion and ventilation pressures were continuously monitored throughout culture. After isolated lung culture, the lungs were removed from the chamber, weighed, and tissue samples were taken for histology.

Perfusate Analysis

Perfusate (culture media) samples were drawn from upstream of the PA and downstream of the PV. Perfusate composition was analyzed during the culture period using an i-STAT 1 Analyzer (Abbott Point of Care Inc., Princeton, NJ) with CG8+ cartridges (Abbott) to measure pH, $PO_2$, $PCO_2$, and glucose. Perfusate lactate content was not measured in short-term ILC experiments. Changes in media components are expressed as the difference between the PA and PV measurements. Thus negative values indicate a reduction and positive values indicate an increase.

Histology & Immunofluorescence

Tissue samples were fixed overnight in 10% formalin under a vacuum before being transferred to 70% ethanol, embedded in paraffin, sectioned at 5 μm for staining. Hematoxylin and eosin (H&E) staining was used to evaluate general morphology. A terminal deoxynucleotidyl transferase dUTP nick end-labeling assay (Promega DeadEnd Fluorometric TUNEL System, Promega Corporation, Madison, WI) was used to evaluate apoptosis. Quantification of apoptosis was carried out by calculating the percentage of TUNEL positive cells per 20× field (approximately 0.3419 $mm^2$) for six random fields per tissue sample. Two or more tissue samples from each lung tested were used for quantification. CellProfiler [19, 20] was used to determine the number of TUNEL positive cells per image.

Primary labeling of tissue sections was performed by first deparaffinizing and rehydrating tissue sections before performing antigen retrieval in a citric acid solution (Antigen Unmasking Solution, Citric Acid Based, Cat. #H-3300, Vector Laboratories Inc., Burlingame, CA) in a pressure cooker, washing sections in PBS, blocking with 5% donkey serum (Cat. #5-30-100ML, EMD Millipore, Darmstadt, Germany) in PBS for 30 minutes, and incubating slides overnight (18 hours) with the primary antibody. Primary antibodies for VE-cadherin (Cat. #sc-9989, Santa Cruz Biotechnology, Dallas, TX), E-cadherin (Cat. #610181, BD Biosciences, San Jose, CA), ZO-1 (Cat. #61-7300, Life Technologies, Grand Island, NY), and pro-SPB (Cat. #AB3430, EMD Millipore) were used. Secondary labeling of primary antibodies was performed by first washing tissue sections in 0.1% Tween in PBS before incubating for 30 minutes with the corresponding secondary antibody, washing again with 0.1% Tween in PBS, and mounting slides with a DAPI-containing mounting media (DAPI Fluoromount-G, Cat. #0100-20, SouthernBiotech, Birmingham, AL).

Calculation of Physical Parameters

Transmural pressure ($P_{TM}$) was calculated as $P_{TM}=P_T-P_{OC}$ and is a measure indicative of the mechanical stress applied to the lung to facilitate ventilation. A positive $P_{TM}$ corresponds to inhalation, and negative $P_{TM}$ corresponds to exhalation. Percent change in organ weight was calculated as $\Delta W_{Organ}=(W_{Final}-W_{Initial})\,W_{Initial}*100$. Glucose and lactate mass consumption rates (Δ glucose and Δ lactate) were calculated as the change in concentration from the PA to the PV multiplied by the perfusion flow rate. Pulmonary vascular resistance (PVR) was calculated as $PVR=(P_{PA}-P_{PV})/Q$ where Q is the perfusion flow rate. All data are presented as the mean±standard deviation or as a boxplot unless otherwise noted.

Results

The short-term (24 h) ILC conditions are outlined in Table 5 for 10% BSA in DMEM (BSA, n=5) and DMEM-only (DMEM, n=3) perfusate groups. Lungs in both groups had cold ischemia times>24 hours prior to culture. PA pressures of both groups were maintained between 20-40 mmHg relative to organ chamber pressure during perfusion and ventilation. PEEP, respiratory rate, transmural pressures, and I:E ratio were adjusted during culture to maintain inflation and reduce the buildup of any visible edema but were similar across groups.

Figure 11A:
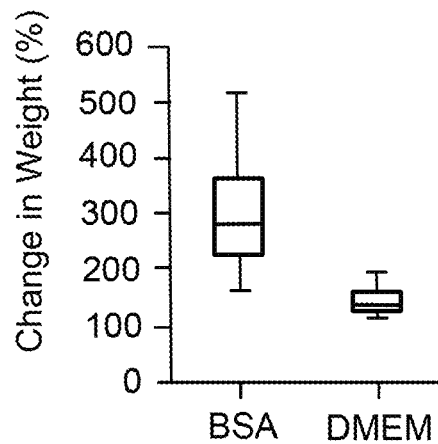
FIG. 11A is a graph of physiological data representing a change in organ weight after short-term (24 h) Isolated Lung Culture (ILC) of porcine lungs.
Figure 11B:
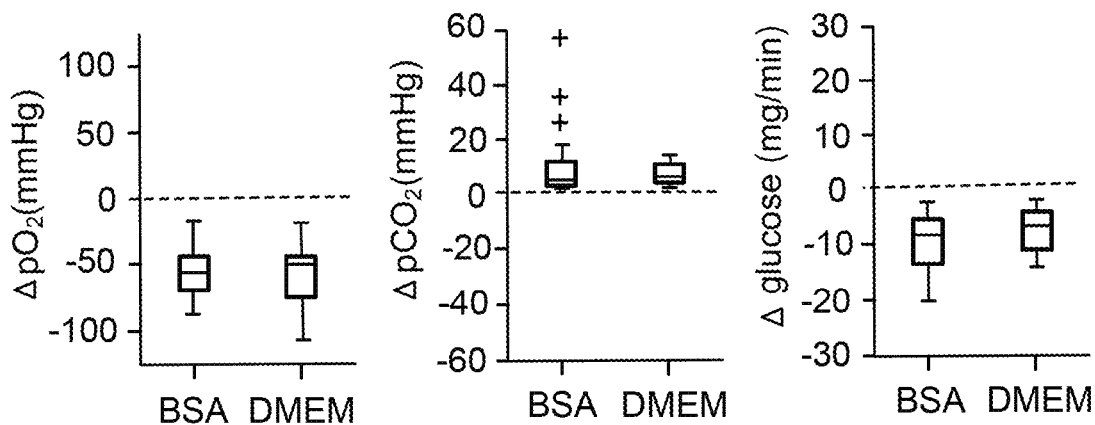
FIG. 11B are graphs of physiological data representing changes in dissolved $O_2$, dissolved $CO_2$, and glucose content of the culture media from the PA to the PV during short-term ILC of porcine lungs. Data shown covers three independent short-term ILCs per condition. Media was sampled 5-7 times per 24-hour period for each set of lungs cultured.

Lungs cultured for 24 hours in 10% BSA exhibited a greater percent change in organ weight than lungs cultured in DMEM only (FIG. 11a). For the BSA group, the mean $pO_2$ values at the PA and PV were 131.7±6.5 mmHg and 79.2±8.1 mmHg respectively. For the DMEM group the mean $pO_2$ values at the PA and PV were 156.1±6.8 mmHg and 101.5±2.5 mmHg respectively. Simultaneous perfusate sampling at the PA and PV over the culture period allowed for realization of the changes in dissolved gas and glucose content of the media as it is perfused. Media from both groups revealed a comparable consumption of dissolved $O_2$ and glucose with a corresponding production of dissolved $CO_2$ (FIG. 11b). These observations are consistent over the entire 24-hour culture period.

Figure 11E:
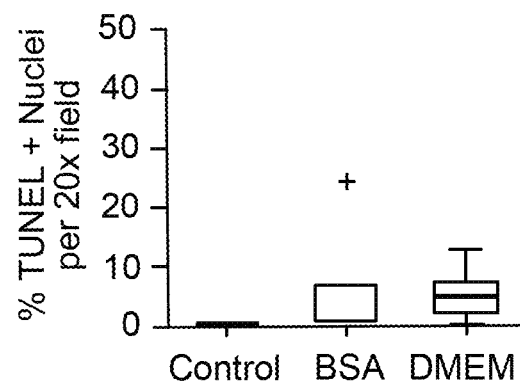
FIG. 11E is a graph of physiological data representing a quantification of TUNEL positive cells in porcine lung tissue after short-term ILC.

Histological analysis (FIG. 11c-d) of tissue samples taken after short-term ILC revealed maintenance of native lung architecture (FIG. 11c). A TUNEL assay (FIG. 11d-e) showed a small increase in the percentage of apoptotic cells that was not statistically significant (ANOVA, p=0.6851).

TABLE 5

Table of short-term ILC conditions

| Short-term ILC Culture condition | 10% BSA | | DMEM only | | Pooled | |
|---|---|---|---|---|---|---|
| | Mean | SD | Mean | SD | Mean | SD |
| Mean PA flow rate (mL/min) | 84.70 | ±34.32 | 58.94 | ±17.48 | 77.34 | ±31.53 |
| Mean PA pressure (mmHg) | 31.82 | ±11.56 | 24.20 | ±2.86 | 29.64 | ±10.21 |
| PEEP (mmHg) | 7.82 | ±2.40 | 7.52 | ±0.52 | 7.70 | ±1.84 |
| Respiratory rate (breaths/min) | 3.17 | ±0.38 | 3.00 | ±0.00 | 3.12 | ±0.32 |
| Max Transmural Pressure (mmHg) | 9.54 | ±6.03 | 15.09 | ±2.49 | 11.39 | ±5.59 |
| Min Transmural Pressure (mmHg) | −8.05 | ±2.02 | −9.07 | ±6.58 | −8.39 | ±3.38 |
| Δ Transmural Pressure (mmHg) | 17.58 | ±4.32 | 24.16 | ±4.09 | 19.77 | ±5.11 |
| I:E | 1.14 | ±0.56 | 1.88 | ±0.06 | 1.35 | ±0.58 |

Example 6—Preservation of Porcine Lungs (Long Term 72 Hours)

This example describes a validation experiment in which isolated porcine lungs were connected to a bioreactor to validate the bioreactor functions via long-term isolated lung culture. Organ chamber pressure (FIG. 10A, $P_{OC}$), PA pressure ($P_{PA}$), PV pressure ($P_{PV}$), PEEP chamber pressure ($P_{PEEP}$) and trachea pressure ($P_T$) are monitored throughout culture. Control of perfusion parameters, ventilation parameters, and logging of bioreactor events are achieved via a National Instruments compact data acquisition (cDAQ) system in combination with a custom developed LabVIEW program (National Instruments, Woburn, MA).

Negative-pressure ventilation in the bioreactors is pressure-controlled and governed by four parameters: the respiratory rate (RR), the inhalation to exhalation (I:E) ratio, the lower organ chamber pressure target ($P_{OC-Lower}$), and the upper organ chamber pressure target ($P_{OC-Upper}$). The RR determines the length of each breath while the I:E ratio defines the time division of each breath into an inhalation or exhalation state. $P_{OC-Lower}$ and $P_{OC-Upper}$ represent the air pressures that the organ chamber is maintained at during inhalation and exhalation respectively. The difference between $P_{OC-Lower}$ and $P_{OC-Upper}$ determines the size of the breath or the range of pressures the exterior of the lung is exposed to. The location of these targets relative to the PEEP chamber pressure, therefore, influences $P_{Transmural}$ during ventilation. For these experiments, $P_{OC-Upper}$ was set close to the PEEP chamber pressure and POC-Lower was set 10-15 mmHg below this, relying on the lung's elastic recoil for an adequate exhalation so as not to collapse recruited airways. These parameters were adjusted during culture to maintain inflation and reduce the buildup of any visible edema according to Table 6. Adjustments were made about as frequent as media sampling, between 3-7 times per 24-hour period.

TABLE 6

Table of Culture Parameter Adjustments

| Observation | Adjustment |
|---|---|
| PPA too high or too low | Decrease or increase PA flow rate |
| Perfusate not draining from PV cannula | Adjust PV cannula |
| Significant atelectasis | Increase I:E or breath size (distance between POC-Upper and POC-Lower) |
| Little visible motion during ventilation | Increase breath size or make breaths longer (reduce RR) |
| Lung deflates before POC-Upper is reached | Decrease POC-Upper or increase I:E |
| Over-inflation | Decrease breath size, decrease I:E, make breaths shorter (increase RR), or increase POC-Lower (bring closer to 0) |

Methods

Porcine lungs (n=4) with <1 h cold ischemia time were used for the establishment of long-term ILC. Organs were prepared for culture and mounted within the organ chamber using the procedure described above with the exception that non-colloid culture media was used. Culture was maintained for at least 72 hours during which the perfusate was periodically sampled at the PA and PV. Culture media was also changed at the same intervals described for short-term ILC an additional media was added if the organ chamber reservoir appeared low (<1 L). Perfusion and ventilation pressures were continuously monitored throughout culture. Functional testing for oxygen exchange was carried out by ventilating with 100% $O_2$ ($FiO_2$=1.0) for 10 minutes and observing the change in partial pressure of $O_2$ in the perfusate as measured at the PV outlet, where $\Delta PV\ pO_2$=PV $pO_2$ post-test−PV $pO_2$ pre-test. This method of functional testing was chosen over comparing $pO_2$ at the PA vs. PV because the system perfuses media in a closed loop and does not deoxygenate the perfusate upstream of the PA. A comparison of PV $pO_2$ values at $FiO_2$=0.21 and 1.0 reveals the ability of the ventilating lung to oxygenate the perfusate in the context of our bioreactor system. The hollow fiber gas exchanger fed with incubator air remained in the perfusion during functional testing. After ILC, the lungs were removed from the chamber, weighed, and tissue samples were taken for histology.

Perfusate Analysis

Perfusate (culture media) samples were drawn from upstream of the PA and downstream of the PV. Perfusate composition was analyzed during the culture period using an i-STAT 1 Analyzer (Abbott Point of Care Inc., Princeton, NJ) with CG8+ cartridges (Abbott) to measure pH, $PO_2$, $PCO_2$, and glucose. CG4+ cartridges were used to measure lactate content in the long-term ILC experiments. Changes in media components are expressed as the difference between the PA and PV measurements, thus negative values indicate a reduction and positive values indicate an increase.

Histology & Immunofluorescence

Tissue samples were fixed overnight in 10% formalin under a vacuum before being transferred to 70% ethanol, embedded in paraffin, sectioned at 5 μm for staining. Hematoxylin and eosin (H&E) staining was used to evaluate general morphology. A terminal deoxynucleotidyl transferase dUTP nick end-labeling assay (Promega DeadEnd Fluorometric TUNEL System, Promega Corporation, Madison, WI) was used to evaluate apoptosis. Quantification of apoptosis was carried out by calculating the percentage of TUNEL positive cells per 20× field (approximately 0.3419 mm$^2$) for six random fields per tissue sample. Two or more tissue samples from each lung tested were used for quantification. CellProfiler [19, 20] was used to determine the number of TUNEL positive cells per image.

Primary labeling of tissue sections was performed by first deparaffinizing and rehydrating tissue sections before performing antigen retrieval in a citric acid solution (Antigen Unmasking Solution, Citric Acid Based, Cat. #H-3300, Vector Laboratories Inc., Burlingame, CA) in a pressure cooker, washing sections in PBS, blocking with 5% donkey serum (Cat. #S-30-100ML, EMD Millipore, Darmstadt, Germany) in PBS for 30 minutes, and incubating slides overnight (18 hours) with the primary antibody. Primary antibodies for VE-cadherin (Cat. #sc-9989, Santa Cruz Biotechnology, Dallas, TX), E-cadherin (Cat. #610181, BD Biosciences, San Jose, CA), ZO-1 (Cat. #61-7300, Life Technologies, Grand Island, NY), and pro-SPB (Cat. #AB3430, EMD Millipore) were used. Secondary labeling of primary antibodies was performed by first washing tissue sections in 0.1% Tween in PBS before incubating for 30 minutes with the corresponding secondary antibody, washing again with 0.1% Tween in PBS, and mounting slides with a DAPI-containing mounting media (DAPI Fluoromount-G, Cat. #0100-20, SouthernBiotech, Birmingham, AL).

Calculation of Physical Parameters

Transmural pressure ($P_{TM}$) was calculated as $P_{TM}=P_T-P_{OC}$ and is a measure indicative of the mechanical stress applied to the lung to facilitate ventilation. A positive $P_{TM}$ corresponds to inhalation, and negative $P_{TM}$ corresponds to exhalation. Percent change in organ weight was calculated as $\Delta W_{Organ}=(W_{Final}-W_{Initial})/W_{Initial}*100$. Glucose and lactate mass consumption rates (Δ glucose and Δ lactate) were calculated as the change in concentration from the PA to the PV multiplied by the perfusion flow rate. Pulmonary vascular resistance (PVR) was calculated as $PVR=(P_{PA}-P_{PV})/Q$ where Q is the perfusion flow rate. All data are presented as the mean±standard deviation or as a boxplot unless otherwise noted.

Results

The long-term (72 h) ILC conditions and results are outlined in Table 7. Lungs had a cold ischemia time of approximately 1 hour prior to culture. PA pressure during long-term ILC was maintained at or below 20 mmHg relative to organ chamber pressure during perfusion and ventilation. PEEP, respiratory rate, transmural pressures, and I:E ratio were adjusted during culture to maintain inflation and reduce the buildup of any visible edema.

Figure 12A:
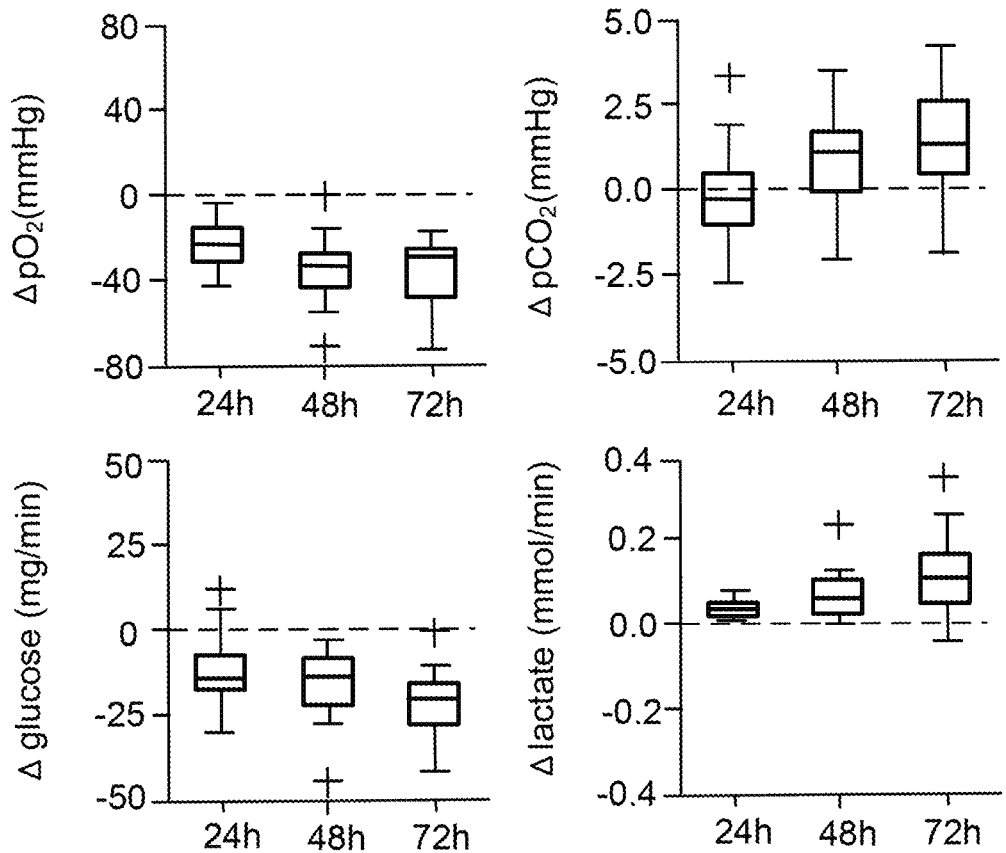
FIG. 12A are graphs of physiological data representing changes in dissolved $O_2$, dissolved CO2, glucose, and lactate content of the culture media from the PA to the PV during long-term (72 h) ILC of porcine lungs. Data shown covers four independent long-term ILCs per condition. Media was sampled 3-5 times per 24-hour period for each set of lungs cultured.
Figure 12B:
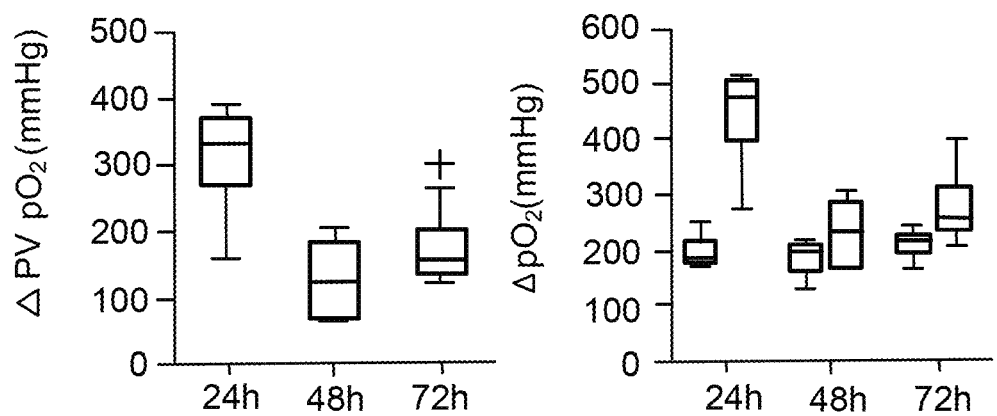
FIG. 12B are graphs of physiological data representing oxygen exchange function of porcine lungs under long-term ILC (left). PA (orange) and PV (green) pO2 values post-functional test (right).
Figure 12C:
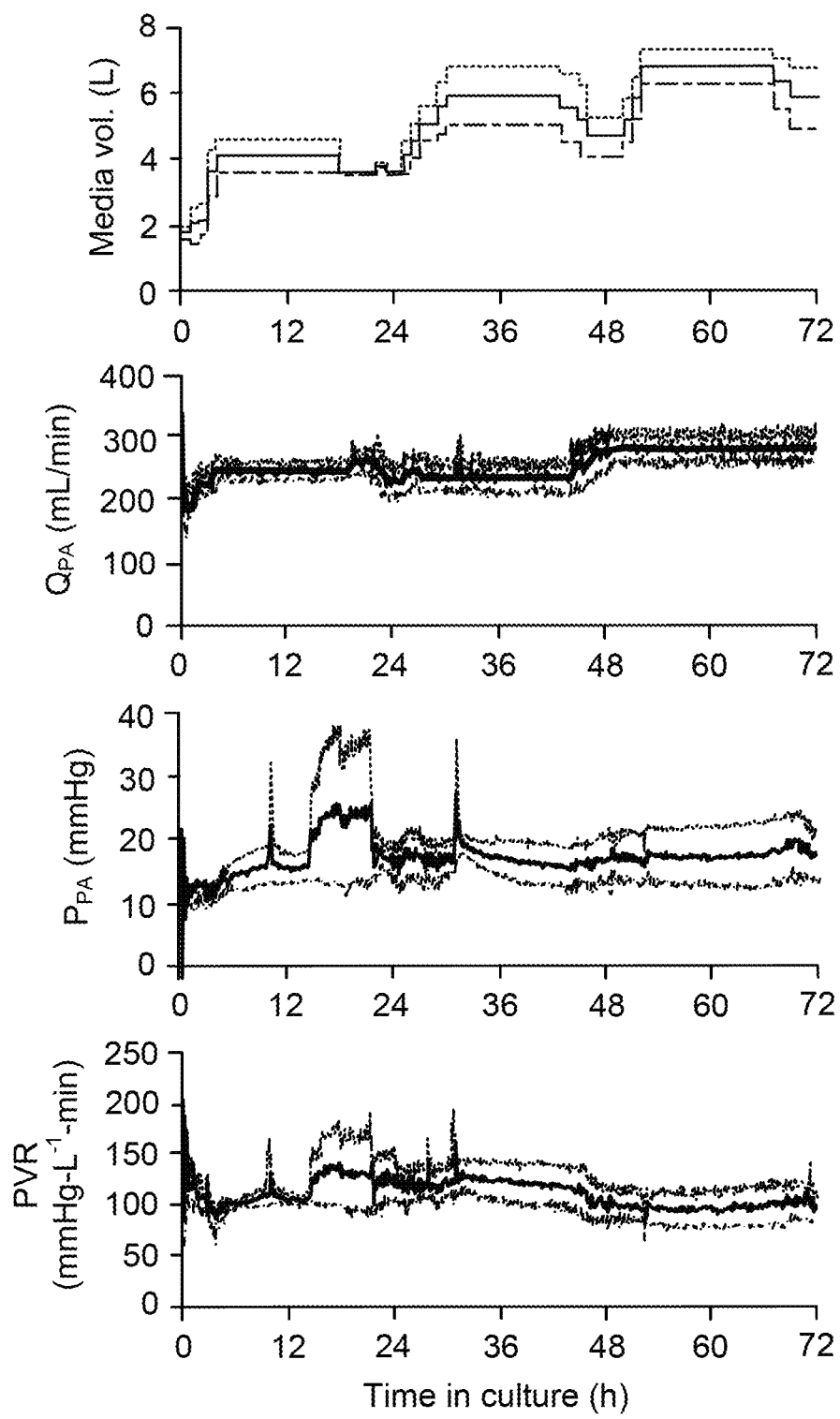
FIG. 12C are graphs of physiological data representing perfusion dynamics of porcine lungs cultured under long-term ILC. Total media volume in bioreactor system (top). Pulmonary artery flow rate (QPA, 2nd from top). Pulmonary artery pressure (PPA, 2nd from bottom). Pulmonary vascular resistance (PVR, bottom). Black lines indicate means. Gray lines indicate mean±SEM.

Lungs under long-term ILC exhibited consumption of $O_2$ and glucose with corresponding production of $CO_2$ (FIG. 12a), albeit to a lesser degree than the lungs tested under short-term ILC (FIG. 11b, note y-axis scale). A corresponding production of lactate was also observed in lungs under long-term ILC (FIG. 12a). Functional testing of lungs under long-term ILC revealed maintenance of oxygen exchanging capability for the entire 72 h (3-day) duration of culture (FIG. 12b, left). Post-functional test PA and PV pO$_2$ values (FIG. 12b, right) reveal a greater pO$_2$ at the PV than the PA and an overall increase in perfusate pO$_2$ compared to when equilibrated with FiO$_2$=0.21 (mean PA pO$_2$ on FiO$_2$ of 0.21=144.0±9.78 mmHg). Total media volume increased with culture time as fresh media was added to when the organ chamber reservoir appeared low (<1 L). A consistent mean PA flow rate (QPA) produced a stable PPA and PVR of lungs under long-term ILC for the duration of the culture period (FIG. 12b).

Figure 12D:
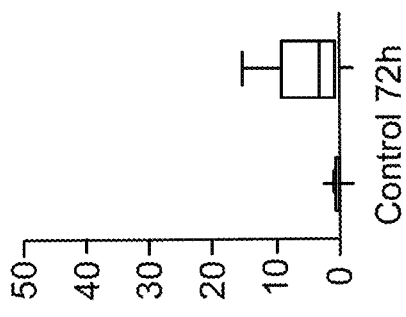
FIG. 12D shows an exemplary TUNEL image of porcine lung tissue after long-term ILC (left). Quantification of TUNEL positive cells (right).
Figure 12D:
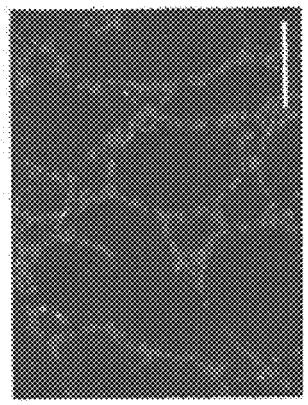
Figure 12E:
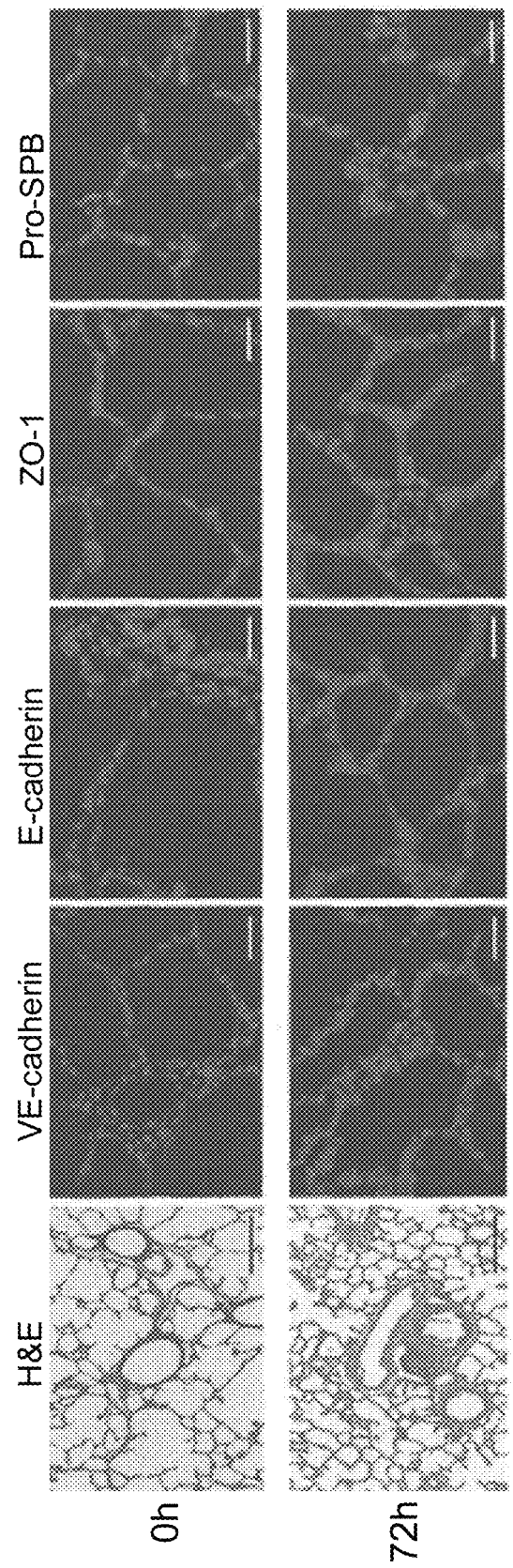
FIG. 12E show images of histological and immunofluorescent analysis of porcine lung tissue before (0 h) and after (72 h) long-term ILC. Hematoxylin and eosin staining (H&E, scale bar, 250 µm). VE-cadherin, E-cadherin, ZO-1, and pro-SPB (red, nuclei in blue, scale bar 50 µm).

A TUNEL assay revealed a small increase in apoptosis in tissue samples taken after the full 72 h culture period compared to the control tissue that was not statistically significant (FIG. 12d, p=0.0692). H&E staining (FIG. 12e) revealed maintenance of lung architecture after long-term ILC. Lung tissue collected after long-term ILC (FIG. 12e, 72h) also retained expression and appearance of VE-cadherin, E-cadherin, ZO-1, and pro-SPB compared to tissue biopsied prior to culture (FIG. 12e, 0 h).

TABLE 7

Table of long-term ILC conditions

| Long-term ILC | DMEM-only | |
|---|---|---|
| Culture condition | Mean | SD |
| Mean PA pressure (mmHg) | 17.30 | ±5.16 |
| PEEP (mmHg) | 6.70 | ±0.62 |
| Respiratory rate (breaths/min) | 4.50 | ±0.55 |
| Max Transmural Pressure (mmHg) | 16.81 | ±1.27 |
| Min Transmural Pressure (mmHg) | −0.50 | ±1.69 |
| Δ Transmural Pressure (mmHg) | 17.30 | ±0.77 |
| I:E | 1.98 | ±0.53 |

Example 7—Preservation of Single Human Lung (Long Term 72 Hours)

This example describes a validation experiment in which an isolated human lung was connected to a bioreactor to validate the bioreactor functions via long-term isolated lung culture. Organ chamber pressure (FIG. 10A, $P_{OC}$), PA pressure ($P_{PA}$), PV pressure ($P_{PV}$), PEEP chamber pressure ($P_{PEEP}$) and trachea pressure ($P_T$) are monitored throughout culture. Control of perfusion parameters, ventilation parameters, and logging of bioreactor events are achieved via a National Instruments compact data acquisition (cDAQ) system in combination with a custom developed LabVIEW program (National Instruments, Woburn, MA).

Negative-pressure ventilation in our system is pressure-controlled and governed by four parameters: the respiratory rate (RR), the inhalation to exhalation (I:E) ratio, the lower organ chamber pressure target ($P_{OC-Lower}$), and the upper organ chamber pressure target ($P_{OC-Upper}$). The RR determines the length of each breath while the I:E ratio defines the time division of each breath into an inhalation or exhalation state. $P_{OC-Lower}$ and $P_{OC-Upper}$ represent the air pressures that the organ chamber is maintained at during inhalation and exhalation respectively. The difference between $P_{OC-Lower}$ and $P_{OC-Upper}$ determines the size of the breath—or the range of pressures the exterior of the lung is exposed to. The location of these targets relative to the PEEP chamber pressure, therefore, influences $P_{Transmural}$ during ventilation. For these experiments, $P_{OC-Upper}$ was set close to the PEEP chamber pressure and $P_{OC-Lower}$ was set 10-15 mmHg below this, relying on the lung's elastic recoil for an adequate exhalation so as not to collapse recruited airways. These parameters were adjusted during culture to maintain inflation and reduce the buildup of any visible edema according to Table 8. Adjustments were made about as frequent as media sampling, between 3-7 times per 24-hour period.

TABLE 8

Table of Culture Parameter Adjustments

| Observation | Adjustment |
|---|---|
| PPA too high or too low | Decrease or increase PA flow rate |
| Perfusate not draining from PV cannula | Adjust PV cannula |
| Significant atelectasis | Increase I:E or breath size (distance between POC-Upper and POC-Lower) |
| Little visible motion during ventilation | Increase breath size or make breaths longer (reduce RR) |
| Lung deflates before POC-Upper is reached | Decrease POC-Upper or increase I:E |
| Over-inflation | Decrease breath size, decrease I:E, make breaths shorter (increase RR), or increase POC-Lower (bring closer to 0) |
| Under-inflation | Increase breath size, increase I:E, make breaths longer (decrease RR), or decrease POC-Lower |

Methods

In coordination with the New England Organ Bank (NEOB), a donated human lung that was not found suitable for transplantation was procured from a heart-beating donor in standard surgical fashion. The pre-donation chest x-ray showed a small amount of basilar atelectasis and the arterial oxygen tension was 116 mmHg on 100% FiO2 indicating compromised gas exchange. The lung was delivered in a sterile container on ice and mounted on a bioreactor immediately after arrival. The right lung was isolated, and the PA, PVs, and trachea were cannulated before being set up as described above for long-term ILC of 72 hours. Cold ischemia time from harvest to reperfusion was 5.5 hours.

Perfusate Analysis

Perfusate (culture media) samples were drawn from upstream of the PA and downstream of the PV. Perfusate composition was analyzed during the culture period using an i-STAT 1 Analyzer (Abbott Point of Care Inc., Princeton, NJ) with CG8+ cartridges (Abbott) to measure pH, $PO_2$, $PCO_2$, and glucose. CG4+ cartridges were used to measure lactate content in the long-term ILC experiments. Changes in media components are expressed as the difference between the PA and PV measurements. Thus negative values indicate a reduction and positive values indicate an increase.

Histology & Immunofluorescence

Tissue samples were fixed overnight in 10% formalin under a vacuum before being transferred to 70% ethanol, embedded in paraffin, sectioned at 5 µm for staining. Hematoxylin and eosin (H&E) staining was used to evaluate general morphology. A terminal deoxynucleotidyl transferase dUTP nick end-labeling assay (Promega DeadEnd Fluorometric TUNEL System, Promega Corporation, Madison, WI) was used to evaluate apoptosis. Quantification of apoptosis was carried out by calculating the percentage of TUNEL positive cells per 20× field (approximately 0.3419 mm$^2$) for six random fields per tissue sample. Two or more tissue samples from each lung tested were used for quantification. CellProfiler was used to determine the number of TUNEL positive cells per image.

Primary labeling of tissue sections was performed by first deparaffinizing and rehydrating tissue sections before performing antigen retrieval in a citric acid solution (Antigen Unmasking Solution, Citric Acid Based, Cat. #H-3300, Vector Laboratories Inc., Burlingame, CA) in a pressure cooker, washing sections in PBS, blocking with 5% donkey serum (Cat. #S-30-100ML, EMD Millipore, Darmstadt, Germany) in PBS for 30 minutes, and incubating slides overnight (18 hours) with the primary antibody. Primary antibodies for VE-cadherin (Cat. #sc-9989, Santa Cruz Biotechnology, Dallas, TX), E-cadherin (Cat. #610181, BD Biosciences, San Jose, CA), ZO-1 (Cat. #61-7300, Life Technologies, Grand Island, NY), and pro-SPB (Cat. #AB3430, EMD Millipore) were used. Secondary labeling of primary antibodies was performed by first washing tissue sections in 0.1% Tween in PBS before incubating for 30 minutes with the corresponding secondary antibody, washing again with 0.1% Tween in PBS, and mounting slides with a DAPI-containing mounting media (DAPI Fluoromount-G, Cat. #0100-20, SouthernBiotech, Birmingham, AL).

Calculation of Physical Parameters

Transmural pressure ($P_{TM}$) was calculated as $P_{TM}=P_T-P_{OC}$ and is a measure indicative of the mechanical stress applied to the lung to facilitate ventilation. A positive $P_{TM}$ corresponds to inhalation, and negative $P_{TM}$ corresponds to exhalation. Percent change in organ weight was calculated as $\Delta W_{Organ}=(W_{Final}-W_{Initial})/W_{Initial}*100$. Glucose and lactate mass consumption rates ($\Delta$ glucose and $\Delta$ lactate) were calculated as the change in concentration from the PA to the PV multiplied by the perfusion flow rate. Pulmonary vascular resistance (PVR) was calculated as $PVR=(P_{PA}-P_{PV})/Q$ where Q is the perfusion flow rate. All data are presented as the mean±standard deviation or as a boxplot unless otherwise noted.

Results

Figure 13A:
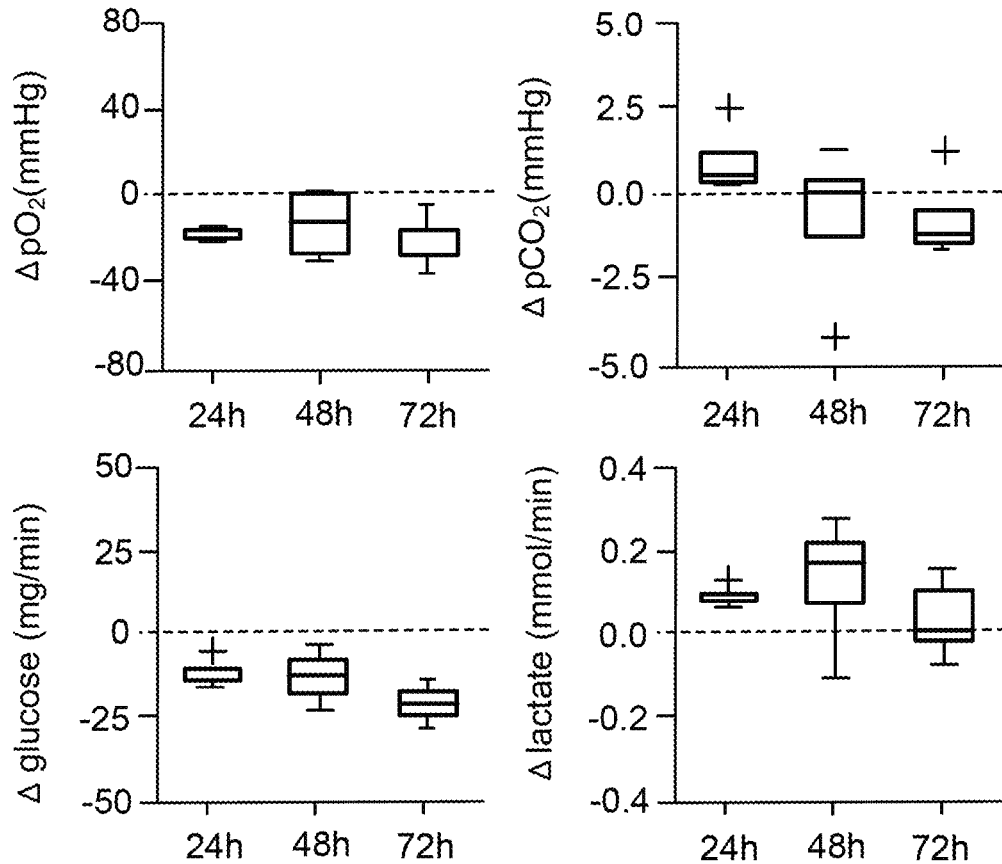
FIG. 13A are graphs of physiological data representing changes in dissolved O2, dissolved CO2, glucose, and lactate content of the culture media from the PA to the PV during long-term (72 h) ILC of a single human lung. Media was sampled 4 times per 24-hour period.
Figure 13B:
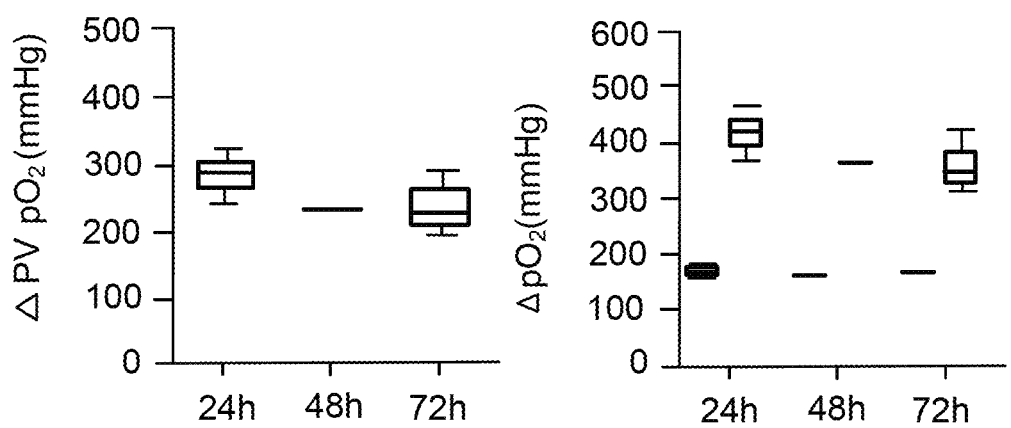
FIG. 13B are graphs of physiological data representing oxygen exchange function of a human lung under long-term ILC (left). PA (orange) and PV (green) pO2 values post-functional test (right).
Figure 13C:
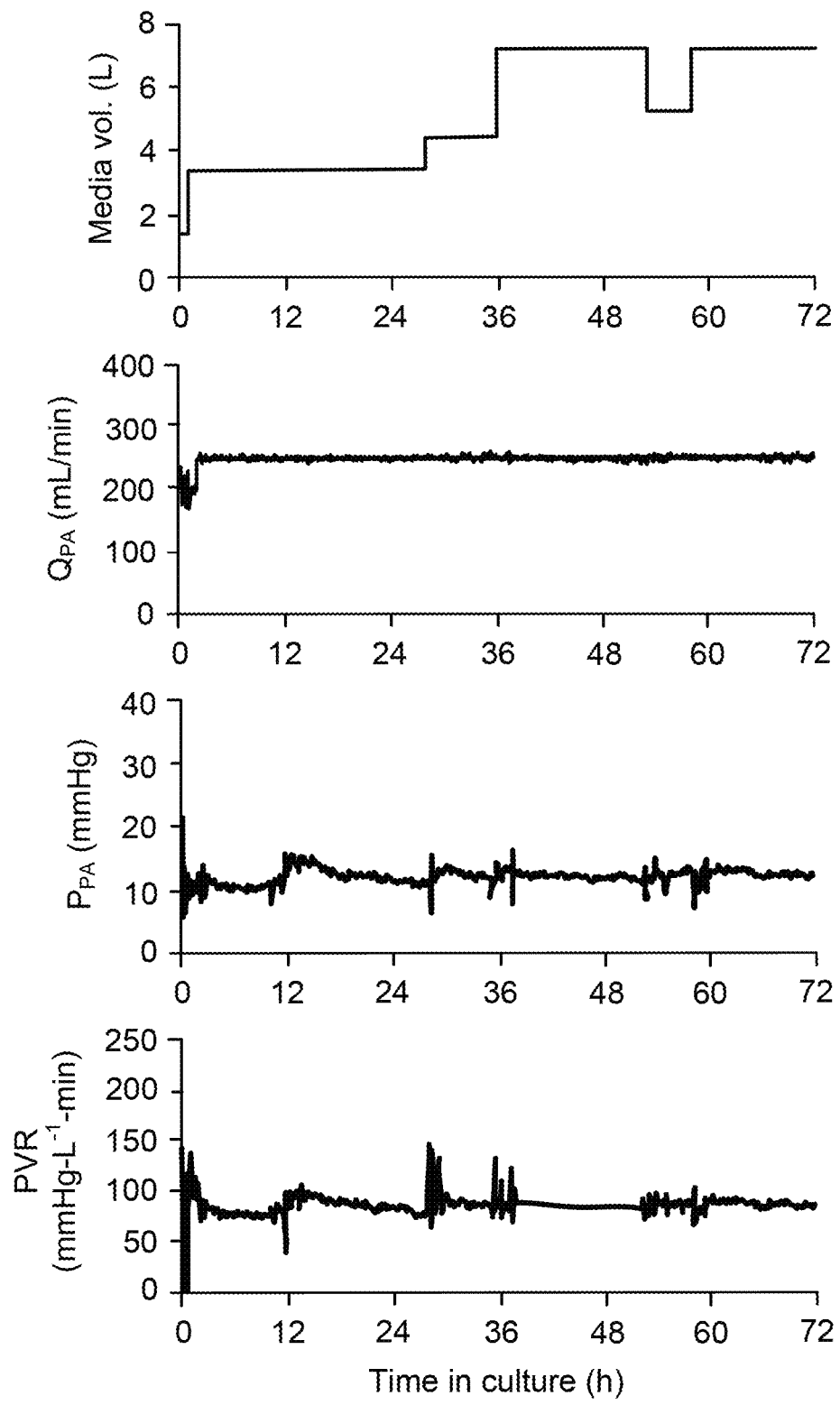
FIG. 13C are graphs of physiological data representing perfusion dynamics of a human lung cultured under long-term ILC. Total media volume in bioreactor system (top). Pulmonary artery flow rate (QPA, 2nd from top). Pulmonary artery pressure (PPA, 2nd from bottom). Pulmonary vascular resistance (PVR, bottom). Black lines indicate means. Gray lines indicate mean±SEM.

The first human lung cultured behaved similarly to the porcine lung sets previously tested. During culture, the mean PA pressure was 12.10 mmHg and PEEP was set at 8.38 mmHg. The respiratory rate was kept at 5 breaths per minute with I:E=1.2 and $P_{TM}$ ranging from 12.91 to −4.47 mmHg ($\Delta P_{TM}$=17.38 mmHg). Consumption of oxygen and glucose were present alongside production of lactate on comparable scales (FIG. 13a). Unlike the porcine lungs, a trend towards the removal of $CO_2$ from the media was observed (FIG. 13a). Oxygen exchange function was also sustained throughout the duration of culture (FIG. 13b, left). Post-functional test PA and PV $pO_2$ values (FIG. 13b, right) reveal a markedly greater $pO_2$ at the PV than the PA compared to the porcine lungs tested and an overall increase in perfusate $pO_2$ compared to when equilibrated with $FiO_2$=0.21 (mean PA $pO_2$ on $FiO_2$ of 0.21=145.1 mmHg). Fresh media was added to the bioreactor system when the reservoir appeared low (<1 L) resulting in an increase in total media volume with culture time (FIG. 13c, top). Again, a consistent mean $Q_{PA}$ produced a stable $P_{PA}$ and PVR of the human lung under long-term ILC for the duration of the culture period (FIG. 13c).

Figure 13D:
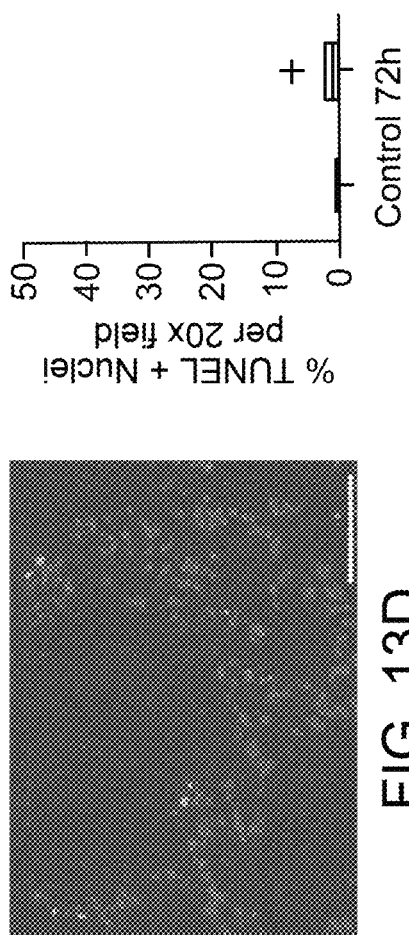
FIG. 13D shows an exemplary TUNEL image of human lung tissue after long-term ILC (left). Quantification of TUNEL positive cells (right).
Figure 13E:
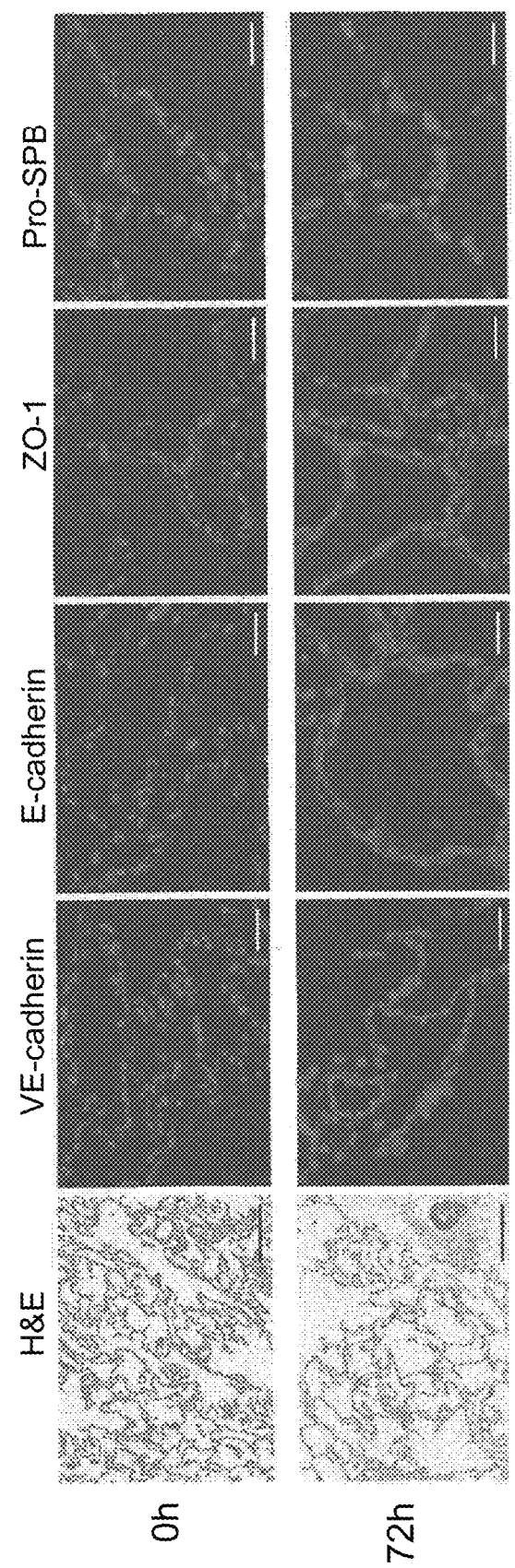
FIG. 13E shows images of histological and immunofluorescent analysis of porcine lung tissue before (0 h) and after (72 h) long-term ILC. Hematoxylin and eosin staining (H&E, scale bar, 250 µm). VE-cadherin, E-cadherin, ZO-1, and pro-SPB (red, nuclei blue, scale bar 50 µm).

A small, non-statistically significant increase in apoptosis was also observed (FIG. 13d, p=0.1352). Histological analysis revealed the maintenance of native lung structure (FIG. 13e, H&E). Human lung under long-term ILC also retained expression and appearance of VE-cadherin, E-cadherin, ZO-1, and pro-SPB (FIG. 13e).

Example 8—Preservation of Rat Lungs

This example describes a validation experiment in which freshly isolated rat lungs were connected to a bioreactor to test the functions of the bioreactor.

Methods

Figure 14A:
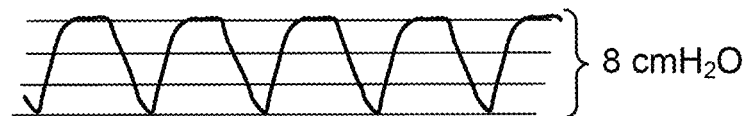
FIGS. 14A-14C are graphs of physiological data associated with rat lung preservation under physiothermal conditions, perfused with 0.6 ml/min KHB in addition to 5% Dextran. 14A; a chart tracing showing that the primary chamber pressure was adjusted 0--8 cm $H_2O$, and respiratory rate was 20/min. 14B is a bar graph showing the time course of PA perfusion pressure, demonstrating maintenance of perfusion pressure over time. 14C is a bar graph showing that the dynamic compliance (Cdyn) also decreased over time. In this experiment, the isolated lung developed edema over 4 hours of perfusion. Cdyn was defined as tidal volume (ml) divided by the peak primary chamber negative pressure value (cmH2O).

Rat lungs were preserved under physiothermal conditions using negative ventilation. The primary chamber pressure was adjusted from 0 to −8 cm $H_2O$, and respiratory rate was 20/min, as shown in FIG. 14A.

Results

Figure 14B:
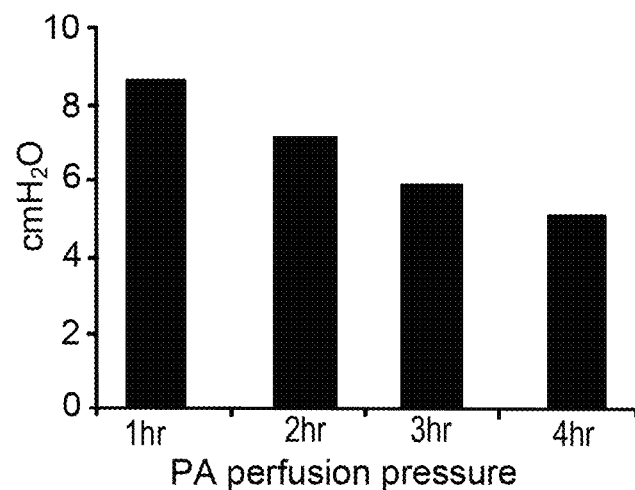
Figure 14C:
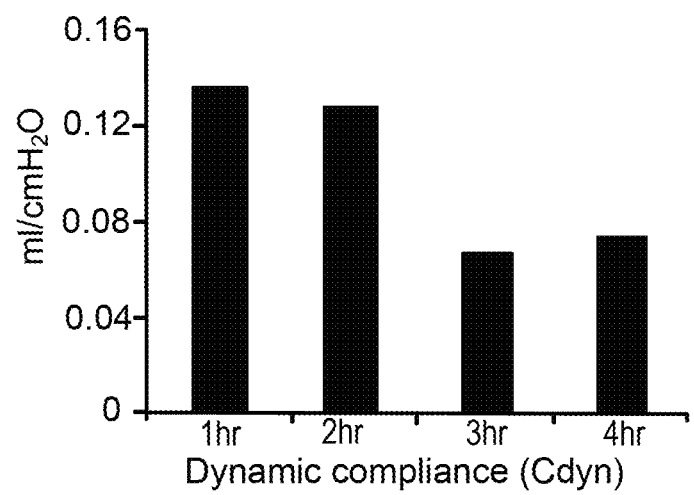

In the first experiment, the KBH with 5% dextran added (0.6 ml/min) perfusate, (as shown in FIGS. 14B-C) resulted in a decrease in the perfusion pressure and dynamic compliance (Cdyn) within 4 hours and the lung was became fully edematous. Cdyn is a functional parameter of lung quality. In addition, the perfusion pressure and the dynamic compliance (Cdyn) also decreased within 6 hours when KHB without dextran (0.6 ml/min) was used.

The physiological data (as shown in FIGS. 15A-C) related to an isolated lung that was perfused with 0.6 ml/min KHB in addition to 5% Dextran was collected. As shown in FIG. 15A, the primary chamber pressure was adjusted 0--8 cm $H_2O$, and the respiratory rate was 20/min. Referring to FIG. 15B, the time course of PA perfusion pressure is shown. The pressure decreased gradually, and, as shown in FIG. 15B, the dynamic compliance (Cdyn) also decreased. In this experiment, the isolated lung was fully edematous after 4 hours of perfusion. Cdyn was defined as tidal volume (ml) divided by the peak primary chamber negative pressure value (cmH2O). Referring to FIG. 15C, there is no evidence that the isolated lung was destroyed or harmed by the preservation. FIG. 15C is an image showing the results of staining a lung specimen after perfusion with hematoxylin and eosin. Left panel, control, 100×. Right panel, sample after 6 hours of perfusion, 100×. This image shows maintenance of normal lung architecture and cellular integrity after 6 h of perfusion and ventilation of a cadaveric lung in the bioreactor.

Example 9—Isolation of Primary Lung Epithelium from Human Donors

This example describes protocols to isolate and expand primary human lung epithelium. The first, an adaptation of the neotnatal rat tissue digest protocol (Protocol A) and the second, a protocol adapted from the literature (Karp, P. H. et al., Protocol B).

Methods:

Protocol A—Based on Rat Neonatal Lung/Kidney Digestions. Timing=~3 Hrs
1. Prepare digestion media: 1 mg/ml dispase (Stem Cell Technologies) with 1 mg/ml collagenase
2. Distribute (a) peripheral lung tissue, ~1.5" cubed, or (b) main airway (branched bronchioles) to 50 ml falcon tube
3. Add 20 ml digestion media to each tube
4. Using small sharp scissors, rapidly cut lung into small minced pieces
5. Incubate minced lungs in digestion buffer for 90 min @ 37° C.
6. Remove samples from 37° C. and allow tissue to briefly settle
7. Pipette fluid from samples and pass through a 100 μm filter
8. Spin down filtrate—300×g, 5 min
9. Re-suspend in red cell lysis buffer and incubate for 5-10 min @ RT
10. Add equivalent volume of αMEM to wash
11. Spin down—300×g, 5 min
12. Count and plate cells direct to culture flasks.

Protocol B—Based on Methods Mol Biol. 2002; 188:115-37. Timing=~24 hrs
1. Prepare Dissociation solution: Pronase (Roche/Boehringer Mannheim, cat. no. 165921) and deoxyribonuclease 1 (Sigma, cat. no. DN-25). For 100 mL, dissolve 140 mg pronase and 10 mg DNase in 100 mL αMEM.
2. Distribute (a) peripheral lung tissue, ~1.5" cubed, or (b) main airway (branched bronchioles) to 50 ml falcon tube
3. Add 20 ml digestion media to each tube
4. Using small sharp scissors, rapidly cut lung into small minced pieces.
5. Incubate minced lungs in digestion buffer for 24 hrs at 4° C. Occasionally invert tubes during dissociation to agitate and break apart cell clumps. Trachea and bronchus tissue require a minimum of 40 h to a maximum 96 h.
6. To end dissociation, add αMEM with 10% FBS to the dissociation solution. Invert the tube(s) several times to agitate the cell suspension. Re-suspend the cell pellet in airway specific and plate on uncoated tissue culture dishes. Incubate the suspension for a minimum of 1 h or longer to allow fibroblasts to attach to. Airway epithelial cells will not attach to the plastic surface without collagen pre-treatment.
7. Collect the non-attached cell suspension from the incubation dish, transfer to coated dishes.

Following digestion of human donor lung by Protocol A and Protocol B, cells were plated onto cultured flasks per-coated with either (1) 0.1% Gelatin or (2) 0.1 mg/ml Collagen IV. Cells were then grown in (1) DMEM, (2) SAGM, (3) AEpiCM, or (4) BEGM.

Results:

Assessing cell attachment and morphology at 24 hours of cultures indicated that Protocol B in combination with collagen IV coating of plates resulted in more epithelial-like colonies. Continuing these cultures for 7 days demonstrated the expansion capacity of these respective cultures. Cells cultured in DMEM were rapidly overgrown by a fibroblast-like population, and these cultures were discarded.

At this point the cells were passaged and re-plated, to further assess expansion capacity. An aliquot of cells from each condition were also seeded into human lung matrix slices to assess for biocompatibility. Addition of Calcein AM dye after 4 days of cell-matrix culture indicted a high level of viability and cell survival in culture and an observed interaction between the cells and the matrix.

The phenotype of the cultured cells was also investigated by immunofluorescent staining on day 11 of culture, following one passage. A heterogeneous phenotype representing subsets of Type 1 alveolar cells (T1a), Clara Cells (CCSP), airway epithelium (CK5), basal cells (p63), Type II alveolar cells (E-Cad), and mesenchymal cells (vimentin).

OTHER EMBODIMENTS

A number of embodiments of the invention have been described. Nevertheless, it will be understood that various modifications may be made without departing from the spirit and scope of the invention.

What is claimed is:

1. A method of preserving, repairing, and/or modifying a lung organ comprising:
   providing an organ chamber configured to connect to an arterial line, to a venous line, and to a tracheal line;
   providing a bi-directional egress pump that is coupled to the organ chamber;

providing a wet-matured lung, or a harvested lung, comprising an airway and substantial vasculature;

connecting the airway to the tracheal line;

connecting the wet-matured lung or the harvested lung to an arterial line and a venous line;

perfusing media over the vasculature of the wet-matured lung or the harvested lung through at least the arterial line or the venous line;

providing the wet-matured lung or the harvested lung with dry ventilation for a time sufficient to produce or maintain a functional lung organ; and minimizing tracheal pressure fluctuation by utilizing the bi-directional egress pump that is provided for correcting fluid shifts through the wet-matured lung or the harvested lung.

2. The method of claim 1 in which minimizing tracheal pressure fluctuation includes:

connecting the tracheal line to a media reservoir, in which the tracheal line includes a ventilator and a tracheal pressure sensor each connected to a controller;

inflating the wet-matured lung or the harvested lung with gas using the ventilator; and deflating the wet-matured lung or the harvested lung using the ventilator, wherein the controller causes the ventilator to inflate or to deflate the wet-matured lung or the harvested lung to minimize the tracheal pressure fluctuation sensed by the tracheal pressure sensor.

3. The method of claim 1, wherein minimizing any tracheal pressure fluctuation includes:

providing a positive pressure manifold connected to the tracheal line and to a controller, wherein the positive pressure manifold includes:

a pressure reservoir;

a gas source connected to the pressure reservoir; and a pressure release valve, and providing a tracheal pressure sensor connected to the tracheal line and to the controller, wherein the controller controls a compressor or the pressure release valve in response to data transmitted from the tracheal pressure sensor.

4. The method of claim 3, wherein the pressure reservoir is appropriately sized to minimize pressure fluctuation during inspiration and expiration.

5. The method of claim 1, wherein the organ chamber further comprises a pneumatic pressure control module connected to the organ chamber, wherein the pneumatic pressure control module:

generates negative pressure in the organ chamber during an inspiration phase;

maintains the organ chamber pressure for a plateau phase; and generates positive pressure in the organ chamber during an expiration phase.

6. The method of claim 1, wherein:

minimizing tracheal pressure fluctuation includes:

providing a positive pressure manifold connected to the tracheal line and to a controller, wherein the positive pressure manifold includes:

a pressure reservoir;

a gas source connected to the pressure reservoir; and a pressure release valve, and providing a tracheal pressure sensor connected to the tracheal line and to the controller, wherein the controller controls a compressor or the pressure release valve in response to data transmitted from the tracheal pressure sensor; and the organ chamber comprises a pneumatic pressure control module connected to the organ chamber, wherein the pneumatic pressure control module:

generates negative pressure in the organ chamber during an inspiration phase;

maintains the organ chamber pressure for a plateau phase; and generates positive pressure in the organ chamber during an expiration phase.

7. The method of claim 1, wherein providing the wet-matured lung comprises:

providing a lung tissue matrix including the airway and the substantial vasculature;

connecting the lung tissue matrix to the arterial line and to the venous line;

seeding the lung tissue matrix with cells over at least one of the following: the arterial line, the venous line, or the tracheal line;

providing the lung tissue matrix with wet ventilation for a time sufficient for a first desired degree of organ maturation to occur to produce a wet-matured organ; and optionally maintaining a substantially constant fluid level in the organ chamber during wet ventilation.

8. The method of claim 3, wherein the positive pressure manifold further comprises an inflatable breathing bag attached to the pressure reservoir, the inflatable breathing bag configured to accommodate sudden volume changes during inspiration and expiration while keeping the pressure in the organ chamber, trachea, and lung constant.

9. The method of claim 3, wherein the positive pressure manifold further comprises:

an inspiratory valve and an expiratory valve connected to the tracheal line, wherein the inspiratory valve and the expiratory valve are one-way valves configured to allow fluid to flow in one direction and prevent backflow; and an expiratory pressure release valve connected to the expiratory valve.

10. The method of claim 9, wherein:

during an expiratory phase, air flows from the tracheal line through the expiratory valve and the expiratory pressure release valve to an exhaust line; and during an inspiratory phase, air flows from the pressure reservoir through the inspiratory valve to the airway of the lung via the tracheal line, and the expiratory pressure release valve ensures that the expiratory line retains a positive pressure during the inspiratory phase.

11. A method of preserving, repairing, and/or modifying a lung organ comprising:

providing an organ chamber configured to connect to an arterial line, to a venous line, and to a tracheal line;

providing a wet-matured lung, or a harvested lung, comprising an airway and substantial vasculature;

connecting the airway to the tracheal line;

connecting the wet-matured lung or the harvested lung to an arterial line and a venous line;

perfusing media over the vasculature of the wet-matured lung or the harvested lung through at least the arterial line or the venous line;

providing the wet-matured lung or the harvested lung with dry ventilation for a time sufficient to produce or maintain a functional lung organ; and minimizing tracheal pressure fluctuation by utilizing a positive pressure manifold sized to minimize tracheal pressure fluctuation by having a size larger than a tidal volume of the wet-matured lung or the harvested lung.

12. The method of claim 11 in which minimizing tracheal pressure fluctuation includes:
connecting the tracheal line to a media reservoir, in which the tracheal line includes a ventilator and a tracheal pressure sensor each connected to a controller;
inflating the wet-matured lung or the harvested lung with gas using the ventilator; and
deflating the wet-matured lung or the harvested lung using the ventilator, wherein the controller causes the ventilator to inflate or to deflate the wet-matured lung or the harvested lung to minimize the tracheal pressure fluctuation sensed by the tracheal pressure sensor.

13. The method of claim 11, wherein minimizing any tracheal pressure fluctuation includes:
providing the positive pressure manifold connected to the tracheal line and to a controller, wherein the positive pressure manifold includes:
a pressure reservoir;
a gas source connected to the pressure reservoir; and
a pressure release valve, and
providing a tracheal pressure sensor connected to the tracheal line and to the controller,
wherein the controller controls a compressor or the pressure release valve in response to data transmitted from the tracheal pressure sensor.

14. The method of claim 13, wherein the pressure reservoir is appropriately sized to minimize pressure fluctuation during inspiration and expiration.

15. The method of claim 11, wherein the organ chamber further comprises a pneumatic pressure control module connected to the organ chamber, wherein the pneumatic pressure control module:
generates negative pressure in the organ chamber during an inspiration phase;
maintains the organ chamber pressure for a plateau phase; and
generates positive pressure in the organ chamber during an expiration phase.

16. The method of claim 11, wherein:
minimizing tracheal pressure fluctuation includes:
providing the positive pressure manifold connected to the tracheal line and to a controller, wherein the positive pressure manifold includes:
a pressure reservoir;
a gas source connected to the pressure reservoir; and
a pressure release valve, and
providing a tracheal pressure sensor connected to the tracheal line and to the controller,
wherein the controller controls a compressor or the pressure release valve in response to data transmitted from the tracheal pressure sensor; and
the organ chamber comprises a pneumatic pressure control module connected to the organ chamber, wherein the pneumatic pressure control module:
generates negative pressure in the organ chamber during an inspiration phase;
maintains the organ chamber pressure for a plateau phase; and
generates positive pressure in the organ chamber during an expiration phase.

17. The method of claim 11, wherein providing the wet-matured lung comprises:
providing a lung tissue matrix including the airway and the substantial vasculature;
connecting the lung tissue matrix to the arterial line and to the venous line;
seeding the lung tissue matrix with cells over at least one of the following: the arterial line, the venous line, or the tracheal line;
providing the lung tissue matrix with wet ventilation for a time sufficient for a first desired degree of organ maturation to occur to produce a wet-matured organ; and
optionally maintaining a substantially constant fluid level in the organ chamber during wet ventilation.

18. The method of claim 13, wherein the positive pressure manifold further comprises an inflatable breathing bag attached to the pressure reservoir, the inflatable breathing bag configured to accommodate sudden volume changes during inspiration and expiration while keeping the pressure in the organ chamber, trachea, and lung constant.

19. The method of claim 13, wherein the positive pressure manifold further comprises:
an inspiratory valve and an expiratory valve connected to the tracheal line, wherein the inspiratory valve and the expiratory valve are one-way valves configured to allow fluid to flow in one direction and prevent backflow; and
an expiratory pressure release valve connected to the expiratory valve.

20. The method of claim 19, wherein:
during an expiratory phase, air flows from the tracheal line through the expiratory valve and the expiratory pressure release valve to an exhaust line; and
during an inspiratory phase, air flows from the pressure reservoir through the inspiratory valve to the airway of the lung via the tracheal line, and the expiratory pressure release valve ensures that the expiratory line retains a positive pressure during the inspiratory phase.

* * * * *